(12) United States Patent
Koskelainen et al.

(10) Patent No.: US 9,249,127 B2
(45) Date of Patent: Feb. 2, 2016

(54) ALPHA2 ADRENOCEPTOR AGONISTS

(71) Applicant: Orion Corporation, Espoo (FI)

(72) Inventors: Tuula Koskelainen, Lohja (FI); Tero Linnanen, Tuusula (FI); Anna Minkkilä, Turku (FI); Mikko Mäkelä, Espoo (FI); Antti Pohjakallio, Espoo (FI)

(73) Assignee: ORION CORPORATION, Espoo (FI)

( * ) Notice: Subject to any disclaimer, the term of this patent is extended or adjusted under 35 U.S.C. 154(b) by 0 days.

(21) Appl. No.: 14/389,466

(22) PCT Filed: Mar. 28, 2013

(86) PCT No.: PCT/FI2013/000013
§ 371 (c)(1),
(2) Date: Sep. 30, 2014

(87) PCT Pub. No.: WO2013/150173
PCT Pub. Date: Oct. 10, 2013

(65) Prior Publication Data
US 2015/0065550 A1 Mar. 5, 2015

Related U.S. Application Data

(60) Provisional application No. 61/619,109, filed on Apr. 2, 2012.

(51) Int. Cl.
*A61K 31/4178* (2006.01)
*C07D 233/04* (2006.01)
*C07D 409/04* (2006.01)
*C07D 405/04* (2006.01)
*C07D 405/14* (2006.01)

(52) U.S. Cl.
CPC .......... *C07D 409/04* (2013.01); *A61K 31/4178* (2013.01); *C07D 233/04* (2013.01); *C07D 405/04* (2013.01); *C07D 405/14* (2013.01)

(58) Field of Classification Search
CPC .......................... A61K 31/4178; C07D 233/04
See application file for complete search history.

(56) References Cited

U.S. PATENT DOCUMENTS 3,438,995 A  4/1969  Faust et al.

FOREIGN PATENT DOCUMENTS

WO  WO 2007/085556 A1  8/2007
WO  WO 2008/009141 A1  1/2008

OTHER PUBLICATIONS

Kneppert, S.M. et al.; "A-61603, A Potent α1-Adrenergic Receptor Agonist, Selective for the α1A Receptor Subtype" *Journal of Pharmacology and Experimental Therapeutics*; vol. 274, No. 1; pp. 97-103; 1995.

Melloni, P. et al.; "Synthesis of new fenmetazole analogues with potential mixed α2-adrenergic antagonistic activity and noradrenaline-uptake inhibitingproperties" *European Journal of Medicinal Chemistry*; vol. 26, No. 2; pp. 207-213; 1991.
Zhang, X. et al.; "Medetomidine Analogs as α2-Adrenergic Ligands 3. Synthesis and Biological Evaluation of a New Series of Medetomidine Analogs and Their Potential Binding Interactions with α2-Adrenoceptors Involving a 'Methyl Pocket'" *Journal of Medicinal Chemistry*; vol. 40, pp. 3014-3024; 1997.
Brede, M. et al.; "$α_2$-Adrenergic Receptor Subtypes—Novel Functions Uncovered in Gene-Targeted Mouse Models": Biology of the Cell, vol. 96; pp. 343-348; 2004.
Bunnett, J. F. et al.; "Homocyclic Ring Closures via Benzyne Intermediates. A New Synthesis of 1-Substituted Benzocyclobutenes"; Bunnett and Skoroz; vol. 27, pp. 3836-3843; Nov. 1962.
Bylund, D.B. et al.; "Pharmacological Characteristics of $α_2$-Adrenergic Receptors: Comparison of Pharmacologically Defined Subtypes with Subtypes Identified by Molecular Cloning"; Molecular Pharmacology, vol. 42; pp. 1-5; Apr. 1992.
Crassous, P. et al.; "Interest of $α_2$-Adrenergic Agonists and Antagonists in Clinical Practice: Background, Facts and Perspectives"; Current Topics in Medicinal Chemistry, vol. 7; pp. 187-194; 2007.
Di, L. et al.; "High Throughput Microsomal Stability Assay for Insoluble Compounds"; International Journal of Pharmaceutics, vol. 317; pp. 54-60; 2006.
Gentili, F. et al.; "Agonists and Antagonists Targeting the Different $α_2$-Adrenoceptor Subtypes"; Current Topics in Medicinal Chemistry, vol. 7; pp. 163-186; 2007.
Gentili, F. et al.; "Imidazoline Binding Sites (IBS) Profile Modulation: Key Role of the Bridge in Determining $I_1$-IBS or $I_2$-IBS Selectivity within a Series of 2-Phenoxymethylimidazoline Analogues": J. Med. Chem., vol. 46; pp. 2169-2176; 2003.
Ishibashi, H. et al.; "Lewis-acid Promoted Aromatic Cyclization of α-Chlorosulfides: Synthesis of Ethyl Isothiochroman-1-carboxylate and Related Compounds"; J. Heterocyclic Chem., vol. 22; pp. 1527-1529; 1985.
Ishihara, M. et al.; "Facile Preparation of 2-Imidazolines from Aldehydes with *tert*-Butyl Hypochlorite"; Synthesis, No. 13; pp. 1939-1942; 2007.
Knölker, H. et al.; "Transition Metal Complexes in Organic Synthesis. Part 58:[1] First Enantioselective Total Synthesis of the Potent Neuronal Celi Protecting Substance Carquinostatin A from (R)-Propene Oxide": Tetrahedron Letters, vol. 41; pp. 1171-1174; 2000.
Larghi, E. L. et al.; "The Oxa-Pictet-Spengler Cyclization: Synthesis of Isochromans and Related Pyran-Type Heterocycles": Synthesis, No. 2; pp. 0187-0220; 2006.
Lehtimäki, J. et al.; "In Vitro and In Vivo Profiling of Fadolmidina, a Novel Potent $α_2$-Adrenoceptor Agonist with Local Mode of Action"; European Journal of Pharmacology, vol. 599; pp. 65-71; 2008.
Mangas-Sánchez, J. et al.; "Straightforward Synthesis of Enantiopure 2,3-Dihydrobenzofurans by a Sequential Stereoselective Biotransformation and Chemical Intramolecular Cyclization"; Organic Letters, vol. 12, No. 15; pp. 3498-3501; 2010.
Westfall, T. C. et al.; "Adrenergic Agonists and Antagonists"; The Pharmacological Basis of Therapeutics, 12th Ed.; Chapter 12; 2001.

*Primary Examiner* — Samantha Shterengarts
(74) *Attorney, Agent, or Firm* — Finnegan, Henderson, Farabow, Garrett & Dunner, LLP

(57) ABSTRACT

Compounds of formula (I), wherein X and $R_1$-$R_6$, are as defined in the claims, exhibit alpha2 agonistic activity and thus are useful as alpha2 agonists, especially as alpha2A agonists. Methods of use of said compounds are also provided.

12 Claims, No Drawings

ALPHA2 ADRENOCEPTOR AGONISTS

This is a national stage application under §371 of International Patent Application No. PCT/FI2013/000013, filed Mar. 28, 2013, which claims the benefit of U.S. Provisional Patent Application No. 61/619,109, filed Apr. 2, 2012, all of which are incorporated herein by reference.

TECHNICAL FIELD

The present invention relates to pharmacologically active isochroman and isothiochroman derivatives, or pharmaceutically acceptable salts and esters thereof, as well as to pharmaceutical compositions comprising them and to their use as alpha2 adrenoceptor agonists, especially as alpha2A agonists.

BACKGROUND OF THE INVENTION

The alpha2-adrenoreceptors ($\alpha_2$) are G protein-coupled cell membrane receptors widely distributed in humans and they are sub-classified into three subtypes in human; alpha2A, alpha2B and alpha2C (Bylund et al, *Mol. Pharmacol.*, 1992, 42, 1-5). Alpha2 adrenoreceptors have a multiplicity of biological functions and compounds effecting to these receptors are attractive targets on various diseases (Goodman & Gilman's The Pharmacological Basis of Therapeutics, $12^{th}$ edition, 2011, chapter 12; Brede et al *Biol. Cell* 2004, 96, 343-348). Indeed, many alpha2 active compounds have been prepared (Gentili et al, *Curr. Top Med. Chem.*, 2007, 7, 163-186) and tested in clinical settings (Crassous et al, *Curr. Top Med. Chem.*, 2007, 7, 187-194). For example, partial alpha2A agonist clonidine is used as a blood-pressure lowering agent and non-alpha2 subtype nonselective full agonist dexmedetomidine is used as a sedative in the intensive care units.

U.S. Pat. No. 3,438,995 discloses some isochroman and isothiochroman derivatives and suggests them to be useful as rubber accelerators, anti-oxidants, corrosion inhibitors, central nervous system (CNS) depressants and anti-inflammatories. WO 2007/085558 discloses a variety of imidazole derivatives useful as TAAR ligands for the treatment of variety of disorders, including various CNS disorders.

SUMMARY OF THE INVENTION

An object of the present invention is to provide novel compounds exhibiting agonistic activities on adrenenergic alpha-receptors, especially on alpha2A receptor. These compounds can be used for treatment of disorders, conditions or diseases like delirium (for example hyperactive delirium), insomnia, ADHD, benzodiazepine (or alcohol or opioid or tobacco) withdrawal, premature ejaculation, hypertension, tachycardia, restless leg syndrome, muscular spasticity, hot flashes, anxiety, post traumatic stress disorder, pain, chronic pelvic pain syndrome, and breakthrough cancer pain, and other possible diseases treatable with adrenergic alpha2 agonists, especially with alpha2A agonists. Accordingly, the present invention provides further compounds to be used as cooperative sedative or analgesic agent in the treatment of mammals. Furthermore, pharmaceutical compositions comprising the present compounds are provided.

The compounds of the present invention are orally active, brain penetrating, selective alpha2A agonists. They have an improved alpha2A activity and/or alpha2A agonistig selectivity against other alpha receptors and/or enhanced potency, as well as improved metabolism in liver hepatocytes in vitro, all together giving moderate in vivo duration of action. Apart from the foregoing pharmacological effects, the compounds of the present invention have less side-effects due to diminutive CYP interactions.

The foregoing as well as other features and advantages of the present teachings will be more fully understood from the following description and claims.

DETAILED DESCRIPTION OF THE INVENTION

The present invention relates to novel isochroman and isothiochroman derivatives having the general formula I,

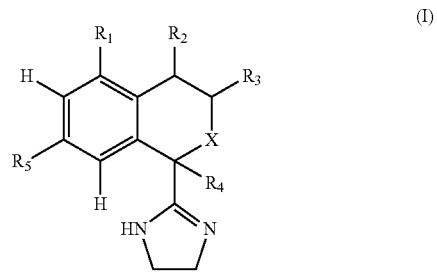

wherein
X is O or S;
$R_1$ is hydroxy, halogen, ($C_1$-$C_6$)alkyl, halo($C_1$-$C_6$)alkyl, ($C_2$-$C_6$)alkenyl, ($C_2$-$C_6$)alkynyl, cyclo($C_3$-$C_6$)alkyl, ($C_1$-$C_6$) alkoxy, halo($C_1$-$C_6$)alkoxy, hydroxy($C_1$-$C_6$)alkyl, cyano, ($C_1$-$C_6$)alkoxy($C_1$-$C_6$)alkyl, ($C_1$-$C_6$)alkoxy($C_1$-$C_6$)alkoxy ($C_1$-$C_6$)alkyl, hydroxy($C_1$-$C_6$)alkoxy, hydroxy($C_1$-$C_6$) alkoxy($C_1$-$C_6$)alkyl, hydroxy($C_2$-$C_6$)alkenyl, ($C_2$-$C_6$)alkenyloxy($C_2$-$C_6$)alkenyl, halo($C_1$-$C_6$)alkoxy($C_1$-$C_6$)alkyl, halo($C_1$-$C_6$)alkoxy-halo($C_1$-$C_6$)alkyl, ($C_1$-$C_6$)alkoxy-halo ($C_1$-$C_6$)alkoxy, carboxy, ($C_1$-$C_6$)alkyl-(C=O)—, ($C_1$-$C_6$) alkoxy-(C=O)—, ($C_1$-$C_6$)alkyl-(C=O)—O—, halo($C_1$-$C_6$)alkyl-(C=O)—, halo($C_1$-$C_6$)alkoxy-(C=O)—, ($R_6$)$_2$N—, ($R_6$)$_2$N—($C_1$-$C_6$)alkyl, ($R_6$)$_2$N—(C=O)—, $R_6$—(C=O)—N($R_6$)—(C=O)—, $R_6$—(O=S=O)—N ($R_6$)—(C=O)—, $R_6$—(C=O)—N($R_6$)—(O=S=O)—, $R_6$—(O=S=O)—N($R_6$)—(O=S=O)=, ($R_6$)$_2$N—N—, ($R_6$)N=N—, ($R_6$)$_2$N—O—, ($R_6$)O—N($R_6$)—, ($C_1$-$C_6$) alkyl-S—, ($C_2$-$C_6$)alkeny-S—($C_2$-$C_6$)alkenyl, hydroxy ($C_1$-$C_6$)alkyl-S—, hydroxy($C_1$-$C_6$)alkyl-S—($C_1$-$C_6$) alkyl, ($C_1$-$C_6$)alkoxy($C_1$-$C_6$)alkyl-S—($C_1$-$C_6$)alkyl; halo ($C_1$-$C_6$)alkyl-S—, halo($C_1$-$C_6$)alkyl-S—($C_1$-$C_6$)alkyl, halo($C_1$-$C_6$)alkyl-S-halo($C_1$-$C_6$)alkyl, $R_6$—(O=S)—, ($R_6$)$_2$N—(O=S)—, $R_6$—(O=S=O)—, ($R_6$)$_2$N—(O=S=O)—, phenyl, phenyl-O—, heteroaryl, heteroaryl-O—, phenyl-N($R_6$)—, heteroaryl-N($R_6$)—, or heteroaryl($C_1$-$C_6$)alkyl;
$R_2$ is H, hydroxy, oxo, fluoro, ($C_1$-$C_6$)alkyl, halo($C_1$-$C_6$) alkyl, ($C_2$-$C_6$)alkenyl, ($C_2$-$C_6$)alkynyl, cyclo($C_3$-$C_6$)alkyl; ($C_1$-$C_6$)alkoxy, halo($C_1$-$C_6$)alkoxy, hydroxy($C_1$-$C_6$)alkyl, cyano; ($C_1$-$C_6$)alkoxy($C_1$-$C_6$)alkyl, ($C_1$-$C_6$)alkoxy($C_1$-$C_6$)alkoxy($C_1$-$C_6$)alkyl, hydroxy($C_1$-$C_6$)alkoxy, hydroxy ($C_1$-$C_6$)alkoxy($C_1$-$C_6$)alkyl; hydroxy($C_2$-$C_6$)alkenyl, ($C_2$-$C_6$)alkenyloxy($C_2$-$C_6$)alkenyl, halo($C_1$-$C_6$)alkoxy($C_1$-$C_6$) alkyl, halo($C_1$-$C_6$)alkoxy-halo($C_1$-$C_6$)alkyl, ($C_1$-$C_6$) alkoxy-halo($C_1$-$C_6$)alkoxy, carboxy, ($C_1$-$C_6$)alkyl-(C=O)—, ($C_1$-$C_6$)alkoxy-(C=O)—, ($C_1$-$C_6$)alkyl-(C=O)—O—, halo($C_1$-$C_6$)alkyl-(C=O)—, halo($C_1$-$C_6$) alkoxy-(C=O)—, ($R_6$)$_2$N—, ($R_6$)$_2$N—($C_1$-$C_6$)alkyl, ($R_6$)$_2$N—(C=O)—, $R_6$—(C=O)—N($R_6$)—(C=O)—, $R_6$—(O=S=O)—N($R_6$)—(C=O)—, $R_6$—(C=O)—N ($R_6$)—(O=S=O)—, $R_6$—(O=S=O)—N($R_6$)—

(O=S=O)—, $(R_6)_2$N—N—, $(R_6)$N=N—, $(R_6)_2$N—O—, $(R_6)$O=N—, $(C_1-C_6)$alkyl-S—, $(C_2-C_6)$alkeny-S—$(C_2-C_6)$alkenyl, hydroxy$(C_1-C_6)$alkyl-S—, hydroxy$(C_1-C_6)$alkyl-S—$(C_1-C_6)$alkyl, $(C_1-C_6)$alkoxy$(C_1-C_6)$alkyl-S—$(C_1-C_6)$alkyl, halo$(C_1-C_6)$alkyl-S—, halo$(C_1-C_6)$alkyl-S—$(C_1-C_6)$alkyl, halo$(C_1-C_6)$alkyl-S-halo$(C_1-C_6)$alkyl, $R_6$—(O=S)—, $(R_6)_2$N—(O=S)—, $R_6$—(O=S=O)—, $(R_6)$N—(O=S=O)—, phenyl, phenyl-O—, heteroaryl, heteroaryl-O—, phenyl-N$(R_6)$—, heteroaryl-N$(R_6)$—, or heteroaryl$(C_1-C_6)$alkyl;

$R_3$ is H, $(C_1-C_6)$alkyl, halo$(C_1-C_6)$alkyl, $(C_1-C_6)$alkoxy, halo$(C_1-C_6)$alkoxy, hydroxy$(C_1-C_6)$alkyl, $(C_1-C_6)$alkoxy$(C_1-C_6)$alkyl, or cyclo$(C_3-C_6)$alkyl;

$R_4$ is H, hydroxy, halogen, $(C_1-C_2)$alkyl, or halo$(C_1-C_2)$alkyl;

$R_5$ is H, hydroxy, halogen, $(C_1-C_6)$alkyl, halo$(C_1-C_2)$alkyl, cyclo$(C_3-C_6)$alkyl, $(C_1-C_6)$alkoxy, halo$(C_1-C_6)$alkoxy, hydroxy$(C_1-C_6)$alkyl, phenyl, or heteroaryl; and $R_6$ is, independently at each occurrence, H, $(C_1-C_6)$alkyl, $(C_1-C_6)$alkoxy$(C_1-C_6)$alkyl hydroxy$(C_1-C_6)$alkyl, halo$(C_1-C_6)$alkyl, or $R_6$ and $R_6$ form, together with the atoms they are attached to, a condensed 4, 5, 6, or 7 membered saturated or unsaturated carbocyclic ring or a condensed 4, 5, 6, or 7 membered saturated or unsaturated heterocyclic ring containing 1 or 2 heteroatom(s) selected from N, O and S, wherein said carbocyclic or heterocyclic ring is unsubstituted or substituted with 1 or 2 substituent(s) each independently being hydroxy, oxo, halogen, $(C_1-C_6)$alkyl, hydroxy$(C_1-C_6)$alkyl, or halo$(C_1-C_6)$alkyl-;

or $R_1$ and $R_2$ form, together with the carbon ring atoms to which they are attached, a condensed 4, 5, 6, or 7 membered-saturated or unsaturated carbocyclic ring or a condensed 4, 5, 6, or 7 membered saturated or unsaturated heterocyclic ring containing 1 or 2 heteroatom(s) selected from N, O and S, wherein said carbocyclic or heterocyclic ring is unsubstituted or substituted with 1 or 2 substituent(s) each independently being hydroxy, oxo, halogen, $(C_1-C_6)$alkyl, $(C_1-C_6)$alkoxy$(C_1-C_6)$alkyl, hydroxy$(C_1-C_6)$alkyl, or halo$(C_1-C_6)$alkyl;

or $R_2$ and $R_3$ form, together with the carbon ring atoms to which they are attached, a condensed 4, 5, 6, or 7 membered saturated or unsaturated carbocyclic ring or a condensed 4, 5, 6, or 7 membered saturated or unsaturated heterocyclic ring containing 1 or 2 heteroatom(s) selected from N, O and S, wherein said carbocyclic or heterocyclic ring is unsubstituted or substituted with 1 or 2 substituent(s) each independently being hydroxy, oxo, halogen, $(C_1-C_6)$alkyl, $(C_1-C_6)$alkoxy$(C_1-C_6)$alkyl, hydroxy$(C_1-C_6)$alkyl, or halo$(C_1-C_6)$alkyl;

or a pharmaceutically acceptable salt or ester thereof.

In a possible subgroup of the compounds of formula I, $R_1$ is hydroxy, halogen, $(C_1-C_6)$alkyl, halo$(C_1-C_6)$alkyl, $(C_2-C_6)$alkenyl, $(C_2-C_6)$alkynyl, cyclo$(C_3-C_6)$alkyl, $(C_1-C_6)$alkoxy, halo$(C_1-C_6)$alkoxy, hydroxy$(C_1-C_6)$alkyl, cyano, $(C_1-C_2)$alkoxy$(C_1-C_2)$alkyl, hydroxy$(C_1-C_2)$alkoxy, halo$(C_1-C_2)$alkoxy$(C_1-C_2)$alkyl, halo$(C_1-C_2)$alkoxy-halo$(C_1-C_2)$alkyl, $(C_1-C_2)$alkoxy-halo$(C_1-C_2)$alkoxy, carboxy, $(C_1-C_3)$alkyl-(C=O)—, $(C_1-C_3)$alkoxy-(C=O)—, halo$(C_1-C_3)$alkyl-(C=O)—, halo$(C_1-C_3)$alkoxy-(C=O)—, $(R_6)_2$N—$(C_1-C_2)$alkyl, $(R_6)_2$N—(C=O)—, $(C_1-C_6)$alkyl-S—, $R_6$—(O=S)—, $R_6$—(O=S=O)—, $(R_6)_2$N—(O=S=O)—, phenyl, phenyl-O—, heteroaryl, heteroaryl-O—, or heteroaryl$(C_1-C_2)$alkyl;

$R_2$ is H, hydroxy, oxo, fluoro, $(C_1-C_6)$alkyl, cyclo$(C_3-C_6)$alkyl, $(C_1-C_6)$alkoxy, halo$(C_1-C_6)$alkoxy, or cyano;

$R_3$ is H, $(C_1-C_6)$alkyl, halo$(C_1-C_6)$alkyl, $(C_1-C_6)$alkoxy, hydroxy$(C_1-C_6)$alkyl, $(C_1-C_6)$alkoxy$(C_1-C_6)$alkyl, or cyclo$(C_3-C_6)$alkyl;

$R_4$ is H, fluoro, $(C_1-C_2)$alkyl, or halo$(C_1-C_2)$alkyl;

$R_5$ is H, hydroxy, halogen, $(C_1-C_6)$alkyl, halo$(C_1-C_2)$alkyl, cyclo$(C_3-C_6)$alkyl, $(C_1-C_6)$alkoxy, halo$(C_1-C_6)$alkoxy, phenyl, or heteroaryl; and $R_6$ is, independently at each occurrence, H, $(C_1-C_3)$alkyl, or $R_6$ and $R_6$ form, together with the atoms they are attached to, a condensed 5, 6 or 7 membered saturated or unsaturated carbocyclic ring or a condensed 5, 6 or 7 membered saturated or unsaturated heterocyclic ring containing 1 or 2 heteroatom(s) selected from N, O and S, wherein said carbocyclic or heterocyclic ring is unsubstituted or substituted with 1 or 2 substituent(s) each independently being hydroxy, oxo, halogen, $(C_1-C_2)$alkyl, or halo$(C_1-C_2)$alkyl-;

or $R_1$ and $R_2$ form, together with the carbon ring atoms to which they are attached, a condensed 5, 6 or 7 membered saturated or unsaturated carbocyclic ring or a condensed 5, 6 or 7 membered saturated or unsaturated heterocyclic ring containing 1 or 2 heteroatom(s) selected from N, O and S, wherein said carbocyclic or heterocyclic ring is unsubstituted or substituted with 1 or 2 substituent(s) each independently being hydroxy, oxo, halogen, $(C_1-C_2)$alkyl, $(C_1-C_2)$alkoxy, hydroxy$(C_1-C_2)$alkyl, or halo$(C_1-C_2)$alkyl.

In a further possible subgroup of the compounds of formula I, $R_1$ is hydroxy, halogen, $(C_1-C_6)$alkyl, halo$(C_1-C_6)$alkyl, $(C_2-C_6)$alkenyl, $(C_2-C_6)$alkynyl, cyclo$(C_3-C_6)$alkyl, $(C_1-C_6)$alkoxy, halo$(C_1-C_6)$alkoxy, hydroxy$(C_1-C_6)$alkyl, cyano, $(R_6)_2$N—(C=O)—, $(C_1-C_6)$alkyl-S—, or heteroaryl; and/or $R_2$ is H or $(C_1-C_6)$alkyl; and/or $R_3$ is H, $(C_1-C_6)$alkyl, halo$(C_1-C_6)$alkyl, or $(C_1-C_6)$alkoxy$(C_1-C_6)$alkyl; and/or $R_4$ is H or $(C_1-C_2)$alkyl; and/or $R_5$ is H, hydroxy, halogen, $(C_1-C_6)$alkyl, or $(C_1-C_6)$alkoxy; and/or $R_6$ is H; and/or $R_1$ and $R_2$ form, together with the carbon ring atoms to which they are attached, a condensed 6 or 7 membered saturated or unsaturated carbocyclic ring; for example $R_1$ is hydroxy, halogen, $(C_1-C_3)$alkyl, halo$(C_1-C_3)$alkyl, $(C_1-C_3)$alkoxy, halo$(C_1-C_3)$alkoxy, or hydroxy$(C_1-C_3)$alkyl; and/or $R_2$ is H or $(C_1-C_2)$alkyl; and/or $R_3$ is H, $(C_1-C_3)$alkyl or halo$(C_1-C_3)$alkyl; and/or $R_4$ is H or methyl; and/or $R_5$ is H, halogen or $(C_1-C_2)$alkyl; and/or $R_1$ and $R_2$ form, together with the carbon ring atoms to which they are attached, a condensed 6 or 7 membered saturated or unsaturated carbocyclic ring; for example $R_1$ is hydroxy, halogen, $(C_1-C_3)$alkyl, halo$(C_1-C_3)$alkyl, $(C_1-C_3)$alkoxy, halo$(C_1-C_3)$alkoxy, or hydroxy$(C_1-C_3)$alkyl; and/or $R_2$ is H or $(C_1-C_2)$alkyl; and/or $R_3$ is H, $(C_1-C_3)$alkyl or halo$(C_1-C_3)$alkyl; and/or $R_4$ is H or methyl; and/or $R_5$ is H, halogen or $(C_1-C_2)$alkyl; such as $R_1$ is halogen, $(C_1-C_2)$alkyl, halo$(C_1-C_2)$alkyl, $(C_1-C_2)$alkoxy, or halo$(C_1-C_2)$alkoxy; and/or $R_2$ is H; and/or $R_3$ is H or $(C_1-C_2)$alkyl; and/or $R_4$ is H; and/or $R_5$ is H.

In further possible subgroup of the compounds of formula I, X is O.

In yet another possible subgroup of the compounds of formula I, the compound is 2-(5-methylisochroman-1-yl)-4,5-dihydro-1H-imidazole, 2-(5-bromoisochroman-1-yl)-4,5-dihydro-1H-imidazole, 2-(1,5-dimethylisochroman-1-yl)-4,5-dihydro-1H-imidazole, 2-(5-chloroisochroman-1-yl)-4,5-dihydro-1H-imidazole, 1-(4,5-dihydro-1H-imidazol-2-yl)isochroman-5-carbonitrile, 2-(5-allylisochroman-1-yl)-4,5-dihydro-1H-imidazole, 2-(5-vinylisochroman-1-yl)-4,5-dihydro-1H-imidazole, 2-(5-ethylisochroman-1-yl)-4,5-dihydro-1H-imidazole, 2-(5-ethylisochroman-1-yl)-4,5-dihydro-1H-imidazole hydrochloride, 2-(5-ethylisochroman-1-yl)-4,5-dihydro-1H-imidazole sulfate, 2-(5-ethylisochroman-1-yl)-4,5-dihydro-1H-imidazole fumarate, 1-(4,5-dihydro-1H-imidazol-2-yl)isochroman-5-ol, (1-(4,5-dihydro-1H-imidazol-2-yl)isochroman-5-yl)methanol, 2-(5-bromo-1-methylisochroman-1-yl)-4,5-dihydro-1H-imidazole, 2-((3R)-5-chloro-3-ethylisochroman-1-yl)-4,5-dihydro-1H-imidazole, slower eluting isomer of 1-(1-(4,5-dihydro-1H-imidazol-2-yl)-1-methylisochroman-5-yl)-2,2-dimethylpropan-1-ol, faster eluting isomer of 1-(1-(4,5-dihydro-1H-imidazol-2-yl)-1-methylisochroman-5-yl)-2,2-dimethylpropan-1-ol, 2-(5-ethynylisochroman-1-yl)-4,5-dihydro-1H-imidazole, 2-((3R)-3-ethyl-5-(trifluoromethyl)isochroman-1-yl)-4,5-dihydro-1H-imidazole, 2-(5-methoxyisochroman-1-yl)-4,5-dihydro-1H-imidazole, 2-(5-methoxyisochroman-1-yl)-4,5-dihydro-1H-imidazole hydrochloride, 2-(5-methoxyisochroman-1-yl)-4,5-dihydro-1H-imidazole sulfate, 2-(5-methoxyisochroman-1-yl)-4,5-dihydro-1H-imidazole hemifumarate, 2-(5-iodoisochroman-1-yl)-4,5-dihydro-1H-imidazole, 2-((3R)-3-methyl-5-(trifluoromethyl)isochroman-1-yl)-4,5-dihydro-1H-imidazole, 2-(5-bromo-4-methylisochroman-1-yl)-4,5-dihydro-1H-imidazole, faster eluting isomer of 2-(1,5-dimethylisochroman-1-yl)-4,5-dihydro-1H-imidazole, slower eluting isomer of 2-(1,5-dimethylisochroman-1-yl)-4,5-dihydro-1H-imidazole, 2-((3R)-1,3,5-trimethylisochroman-1-yl)-4,5-dihydro-1H-imidazole, 2-(5-cyclopropylisochroman-1-yl)-4,5-dihydro-1H-imidazole, 2-(3,5-dimethylisochroman-1-yl)-4,5-dihydro-1H-imidazole, 2-(5-chloro-3-methylisochroman-1-yl)-4,5-dihydro-1H-imidazole, 2-(3-ethyl-5-methylisochroman-1-yl)-4,5-dihydro-1H-imidazole, 2-(5-chloro-1,3-dimethylisochroman-1-yl)-4,5-dihydro-1H-imidazole, 2-(5-bromo-3-methylisochroman-1-yl)-4,5-dihydro-1H-imidazole, 2-(1,3,5-trimethylisochroman-1-yl)-4,5-dihydro-1H-imidazole, 2-(5-bromo-1,3-dimethylisochroman-1-yl)-4,5-dihydro-1H-imidazole, 2-((3R)-5-bromo-3-methylisochroman-1-yl)-4,5-dihydro-1H-imidazole, 2-((3R)-5-chloro-3-methylisochroman-1-yl)-4,5-dihydro-1H-imidazole, 2-((3S)-5-chloro-3-methylisochroman-1-yl)-4,5-dihydro-1H-imidazole, 2-((3S)-5-bromo-3-methylisochroman-1-yl)-4,5-dihydro-1H-imidazole, 2-((3R)-3,5-dimethylisochroman-1-yl)-4,5-dihydro-1H-imidazole, 2-((3S)-3,5-dimethylisochroman-1-yl)-4,5-dihydro-1H-imidazole, 2-(5-methoxy-3-methylisochroman-1-yl)-4,5-dihydro-1H-imidazole, 2-(5-ethyl-3-methylisochroman-1-yl)-4,5-dihydro-1H-imidazole, 2-(5-bromo-3-propylisochroman-1-yl)-4,5-dihydro-1H-imidazole, 2-(5-isopropylisochroman-1-yl)-4,5-dihydro-1H-imidazole, 2-(5-fluoroisochroman-1-yl)-4,5-dihydro-1H-imidazole, 2-(5-bromo-3-ethylisochroman-1-yl)-4,5-dihydro-1H-imidazole, 2-((3R)-5-methoxy-3-methylisochroman-1-yl)-4,5-dihydro-1H-imidazole, 2-((3R)-5-ethyl-3-methylisochroman-1-yl)-4,5-dihydro-1H-imidazole, 2-((3R)-5-ethyl-3-methylisochroman-1-yl)-4,5-dihydro-1H-imidazole hydrochloride, 2-((3R)-5-ethyl-3-methylisochroman-1-yl)-4,5-dihydro-1H-imidazole hemifumarate, 2-(3-ethyl-5-methoxyisochroman-1-yl)-4,5-dihydro-1H-imidazole, 2-((3R)-3,5-diethylisochroman-1-yl)-4,5-dihydro-1H-imidazole, 2-((3R)-3-ethyl-5-methylisochroman-1-yl)-4,5-dihydro-1H-imidazole, 2-((3R)-3-ethyl-5-methylisochroman-1-yl)-4,5-dihydro-1H-imidazole hydrochloride, 2-((3R)-3-ethyl-5-methylisochroman-1-yl)-4,5-dihydro-1H-imidazole sulfate, 2-((3R)-3-ethyl-5-methylisochroman-1-yl)-4,5-dihydro-1H-imidazole hemifumarate, 2-((3R)-3-methyl-5-(trifluoromethoxy)isochroman-1-yl)-4,5-dihydro-1H-imidazole, 2-((3R)-5-fluoro-3-methylisochroman-1-yl)-4,5-dihydro-1H-imidazole, 2-(5-ethoxyisochroman-1-yl)-4,5-dihydro-1H-imidazole, 2-(5-methyl-3-(2,2,2-trifluoroethyl)isochroman-1-yl)-4,5-dihydro-1H-imidazole, 2-((3S)-5-methoxy-3-methylisochroman-1-yl)-4,5-dihydro-1H-imidazole, 2-(5-(furan-3-yl)isochroman-1-yl)-4,5-dihydro-1H-imidazole, 2-(5-(prop-1-yn-1-yl)isochroman-1-yl)-4,5-dihydro-1H-imidazole, 1-(4,5-dihydro-1H-imidazol-2-yl)isochroman-5-carboxamide, 2-(3,7,8,9,10,10a-hexahydro-1H-cyclohepta[de]isochromen-3-yl)-4,5-dihydro-1H-imidazole, slower eluting isomer of 1-(1-(4,5-dihydro-1H-imidazol-2-yl)isochroman-5-yl)ethanol, 2-(5,7-dimethylisochroman-1-yl)-4,5-dihydro-1H-imidazole, 2-(7-bromo-5-methylisochroman-1-yl)-4,5-dihydro-1H-imidazole, 2-(7-methoxy-5-methylisochroman-1-yl)-4,5-dihydro-1H-imidazole, 2-(3,5-dimethylisothiochroman-1-yl)-4,5-dihydro-1H-imidazole, 2-(5-bromo-3-methylisothiochroman-1-yl)-4,5-dihydro-1H-imidazole, 2-(5-methylisothiochroman-1-yl)-4,5-dihydro-1H-imidazole, 2-(5-bromoisothiochroman-1-yl)-4,5-dihydro-1H-imidazole, 2-(5-bromo-1-methylisothiochroman-1-yl)-4,5-dihydro-1H-imidazole, 2-(5,7-dibromo-3-ethylisochroman-1-yl)-4,5-dihydro-1H-imidazole hydrochloride, enantiomer of 2-5-bromo-3-(2,2,2-trifluoroethyl)isochroman-1-yl)-4,5-dihydro-1H-imidazole hydrochloride, 2-(5-methoxy-1-methylisochroman-1-yl)-4,5-dihydro-1H-imidazole, 2-(5-methoxyisothiochroman-1-yl)-4,5-dihydro-1H-imidazole, 2-((3R)-5-methoxy-1,3-dimethylisochroman-1-yl)-4,5-dihydro-1H-imidazole, 2-(5-(2,2,2-trifluoroethyl)isochroman-1-yl)-4,5-dihydro-1H-imidazole, 2-((3R)-5-ethyl-1,3-dimethylisochroman-1-yl)-4,5-dihydro-1H-imidazole, 2-(5-methyl-3-(methoxymethyl)isochroman-1-yl)-4,5-dihydro-1H-imidazole, 1-(4,5-dihydro-1H-imidazol-2-yl)-5-methylisochroman-7-ol hydrobromide, 1-(4,5-dihydro-1H-imidazol-2-yl)-3-ethylisochroman-5-ol hydrochloride, enantiomer-2 of 2-(5-methoxy-3-(2,2,2-trifluoroethyl)methylisochroman-1-yl)-4,5-dihydro-1H-imidazole, 2-(1,5-dimethylisothiochroman-1-yl)-4,5-dihydro-1H-imidazole, 2-(5-(trifluoromethoxy)isochroman-1-yl)-4,5-dihydro-1H-imidazole hydrochloride, enantiomer-1 of 2-(3-ethylisochroman-1-yl)-4,5-dihydro-1H-imidazole hydrochloride, 2-(3-(2-fluoroethyl)-5-methylisochroman-1-yl)-4,5-dihydro-1H-imidazole hydrochloride, enantiomer of 2-(5-methoxyisochroman-1-yl)-4,5-dihydro-1H-imidazole, enantiomer-2 of 2-5-bromo-3-(2,2,2-trifluoroethyl)isochroman-1-yl)-4,5-dihydro-1H-imidazole hydrochloride, 2-(3-(2,2-difluoroethyl)-5-methylisochroman-1-yl)-4,5-dihydro-1H-imidazole hydrochloride; 2-(7-methoxy-3,5-dimethylisochroman-1-yl)-4,5-dihydro-1H-imidazole, enantiomer-2 of 2-((3)-5-methyl-3-(2,2,2-trifluoroethyl)isochroman-1-yl)-4,5-dihydro-1H-imidazole hydrochloride, 2-(5-(methylthio)isochroman-1-yl)-4,5-dihydro-1H-imidazole, enantiomer-2 of 2-((3)-5-bromo-3-propylisochroman-1-yl)-4,5-dihydro-1H-imidazole hydrochloride, enantiomer-2 of 2-((3R)-3-(2,2-difluoroethyl)-5-methylisochroman-1-yl)-4,5-dihydro-1H-imidazole hydrochloride; 2-(5-(difluoromethoxy)isochroman-1-yl)-4,5-dihydro-1H-imidazole hydrochloride, 2-((3R)-3-ethyl-5-methoxyisochroman-1-yl)-4,5-dihydro-1H-imidazole, enantiomer-1 of 2-(5-chloroisochroman-1-yl)-4,5-dihydro-1H-imidazole hydrochloride, 2-((3R)-5-(difluoromethoxy)-3-methylisochroman-1-yl)-4,5-dihydro-1H-imidazole hydrochloride, enantiomer of 2-(5-bromo-3-ethylisochroman-1-yl)-4,5-dihydro-1H-imidazole, enantiomer-1 of 2-(5-chloroisochroman-1-yl)-4,5-dihydro-1H-imidazole hydrochloride, enantiomer-2 of 2-(3-ethylisochroman-1-yl)-4,5-dihydro-1H-imidazole, enantiomer-2 of 2-(5-methoxyoisochroman-1-yl)-4,5-dihydro-1H-imidazole hydrochloride, 2-(1-methyl-1,3-dihydrobenzo[de]isochromen-1-yl)-4,5-dihydro-1H-imidazole, 2-(5-(difluoromethyl)isochroman-1-yl)-4,5-dihydro-1H-imidazole hydrochloride, enantiomer-2 of 2-(5-chloroisochroman-1-yl)-4,5-dihydro-1H-imidazole hydrochloride, enantiomer-2 of 2-(5-bromoisochroman-1-yl)-4,5-dihydro-1H-imidazole hydrochloride, 2-(1,3-dihydrobenzo[de]isochromen-1-yl)-4,5-dihydro-1H-imidazole hydrochloride, enantiomer of 2-(1-methyl-1,3-dihydrobenzo[de]isochromen-1-yl)-4,5-dihydro-1H-imidazole, 2-(3-methyl-1,3-dihydrobenzo[de]isochromen-1-yl)-4,5-dihydro-1H-imidazole hydrochloride, 2-(3-ethyl-1,3-dihydrobenzo[de]isochromen-1-yl)-4,5-dihydro-1H-imidazole hydrochloride, or enantiomer of 2-(5-bromo-1-methylisochroman-1-yl)-4,5-dihydro-1H-imidazole.

The terms employed herein have the meanings indicated below. The term "at least one" employed in the meanings below refers to one or several, such as one. For example, the term "at least one halogen" refers to one or several halogens, for example three, two or one halogens, such as three halogens.

The term "hydroxy", as employed herein as such or as part of another group, refers to a —OH group.

The term "halo" or "halogen", as employed herein as such or as part of another group, refers to fluorine, chlorine, bromine, or iodide.

The term "$(C_1-C_6)$alkyl", "$(C_1-C_4)$alkyl", "$(C_1-C_3)$alkyl", and "$(C_1-C_2)$alkyl", as employed herein as such or as part of another group, refers to a saturated straight or branched carbon chain having 1 to 6, 1 to 4, 1 to 3, and 1 to 2 carbon atom(s), respectively. Representative examples of $(C_1-C_6)$alkyl, $(C_1-C_4)$alkyl, $(C_1-C_3)$alkyl, and $(C_1-C_2)$alkyl include, but are not limited to, methyl, ethyl, n-propyl, iso-propyl, n-butyl, iso-butyl, sec-butyl, tert-butyl, n-pentyl, iso-pentyl, and n-hexyl.

The term "$(C_2-C_6)$alkenyl" and "$(C_2-C_3)$alkenyl", as employed herein as such or as part of another group, refers to a straight or branched carbon chain having 2 to 6 and 2 to 3 carbon atom(s), respectively, and containing at least one carbon-carbon double bond. Representative examples of $(C_2-C_6)$alkenyl and $(C_2-C_3)$alkenyl include, but are not limited to ethenyl and prop-2-en-1-yl.

The term "$(C_2-C_6)$alkynyl", as employed herein as such or as part of another group, refers to a straight or branched carbon chain having 2, 3, 4, 5, or 6 carbon atom(s) and containing at least one carbon-carbon triple bond. Representative examples of $(C_2-C_6)$alkynyl include, but are not limited to ethynyl, prop-1-yn-1-yl and prop-2-ynyl.

The term "cyclo$(C_3-C_6)$alkyl" as employed herein as such or as part of another group, refers to a saturated hydrocarbon group having cyclic moiety and containing 3, 4, 5, or 6 carbon atom(s). Representative examples of cyclo$(C_3-C_6)$alkyl include, but are not limited to cyclopropyl, cyclobutyl, cyclopentyl, and cyclohexyl.

The term "$(C_1-C_6)$alkoxy" and "$(C_1-C_4)$alkoxy", as employed herein as such or as part of another group, refers to an $(C_1-C_6)$alkyl or an $(C_1-C_4)$alkyl group, respectively, as defined herein, appended to the parent molecular moiety through an oxygen atom. Representative examples of $(C_1-C_6)$alkoxy and $(C_1-C_4)$alkoxy include, but are not limited to, methoxy, ethoxy, n-propoxy, n-butoxy, iso-butoxy, sec-butoxy, tert-butoxy, 2,2-dimethylpropoxy, 3-methylbutoxy, and n-hexoxy.

The term "halo$(C_1-C_6)$alkyl", as employed herein as such or as part of another group, refers to at least one halogen, as defined herein, appended to the parent molecular moiety through an $(C_1-C_6)$alkyl group, as defined herein. When there are several halogens, the halogens can be attached to the same or different carbon atom and the halogens can be identical or different. Representative examples of halo$(C_1-C_6)$alkyl include, but are not limited to, fluoromethyl, difluoromethyl, trifluoromethyl, 2-fluoroethyl, 2-cloroethyl, 2,2,2-trifluoroethyl, 1,2,2-trifluoroethyl, 2-cloropropyl, 3-fluoropropyl, 3-bromopropyl, 1,3-difluoropropyl, and 3,3,3-trifluoropropyl.

The term "halo$(C_1-C_6)$alkoxy", as employed herein as such or as part of another group, refers to at least one halogen appended to the parent molecular moiety through an $(C_1-C_6)$alkoxy group, as defined herein. When there are several halogens, the halogens can be attached to the same or different carbon atom and the halogens can be identical or different. Representative examples of halo$(C_1-C_6)$alkoxy include, but are not limited to, fluoromethoxy, chloromethoxy, difluoromethoxy, trifluoromethoxy, 2-bromoethoxy, 2,2,2-trifluoroethoxy, 3-fluoropropoxy, 2-cloropropoxy, 3,3,3-trifluoropropoxy, and 4-fluorobutoxy.

The term "halo$(C_1-C_6)$alkoxy$(C_1-C_6)$alkyl", as employed herein as such or as part of another group, refers to an halo$(C_1-C_6)$alkoxy group, as defined herein, appended to the parent molecular moiety through an $(C_1-C_6)$alkyl group, as defined herein.

The term "halo$(C_1-C_6)$alkoxy-halo$(C_1-C_6)$alkyl", as employed herein as such or as part of another group, refers to an halo$(C_1-C_6)$alkoxy group, as defined herein, appended to the parent molecular moiety through an halo$(C_1-C_6)$alkyl group, as defined herein.

The term "$(C_1-C_6)$alkoxy-halo$(C_1-C_6)$alkoxy", as employed herein as such or as part of another group, refers to an $(C_1-C_6)$alkoxy group, as defined herein, appended to the parent molecular moiety through an halo$(C_1-C_6)$alkoxy group, as defined herein.

The term "carboxy", as employed herein as part of another group, refers to a —COOH group.

The term "cyano", as employed herein as part of another group, refers to a —CN group.

The term "oxo", as employed herein as part of another group, refers to a =O group.

The term "hydroxy$(C_1-C_6)$alkyl", as employed herein as such or as part of another group, refers to at least one hydroxy group, as defined herein, appended to the parent molecular moiety through an $(C_1-C_6)$alkyl group, as defined herein. Representative examples of hydroxy$(C_1-C_6)$alkyl include, but are not limited to, hydroxymethyl, 1-hydroxyethyl, 2-hydroxyethyl, 2,2-dihydroxyethyl, 1-hydroxypropyl, 3-hydroxypropyl, 1-hydroxy-1-methylethyl, 1-hydroxy-1-methylpropyl, and 1-hydroxy-2,2-dimethyl-prop-1 I-yl.

The term "hydroxy$(C_2-C_6)$alkenyl", as employed herein, refers to at least one hydroxy group, as defined herein, appended to the parent molecular moiety through an $(C_2-C_6)$alkenyl group, as defined herein. Representative examples of hydroxy($C_2$-$C_6$)alkenyl include, but are not limited to, 1-hydroxyethenyl, 2-hydroxyethenyl, and 1-hydroxyprop-2-enyl.

The term "($C_1$-$C_6$)alkoxy($C_1$-$C_6$)alkyl", as employed herein as such or as part of another group, refers to at least one ($C_1$-$C_6$)alkoxy group, as defined herein, appended to the parent molecular moiety through an ($C_1$-$C_6$)alkyl group, as defined herein. When there are several ($C_1$-$C_6$)alkoxy groups, the ($C_1$-$C_6$)alkoxy groups can be identical or different. Representative examples of ($C_1$-$C_6$)alkoxy($C_1$-$C_6$)alkyl include, but are not limited to, methoxymethyl, ethoxymethyl, propoxymethyl, 2-methoxyethyl, 2-ethoxyethyl, 2,2-dimethoxyethyl, 1-methyl-2-propoxyethyl, 1-methoxy-1-methylethyl, and 4-methoxybutyl.

The term "hydroxy($C_1$-$C_6$)alkoxy", as employed herein as such or as part of another group, refers to at least one hydroxy group, as defined herein, appended to the parent molecular moiety through an ($C_1$-$C_6$)alkoxy group, as defined herein. Representative examples of hydroxy($C_1$-$C_6$)alkoxy include, but are not limited to, hydroxymethoxy, dihydroxymethoxy, 2-hydroxyethoxy, 2-hydroxypropoxy, 3-hydroxypropoxy, 2-hydroxybutoxy, and 2-hydroxy-1-methylethoxy.

The term "hydroxy($C_1$-$C_6$)alkoxy($C_1$-$C_6$)alkyl", as employed herein as such or as part of another group, refers to an hydroxy($C_1$-$C_6$)alkoxy group, as defined herein, appended to the parent molecular moiety through an ($C_1$-$C_6$)alkyl group, as defined herein.

The term "($C_1$-$C_6$)alkoxy($C_1$-$C_6$)alkoxy", as employed herein as such or as part of another group, refers to at least one ($C_1$-$C_6$)alkoxy group, as defined herein, appended to the parent molecular moiety through an ($C_1$-$C_6$)alkoxy group, as defined herein. The ($C_1$-$C_6$)alkoxy groups can be identical or different. Representative examples of ($C_1$-$C_6$)alkoxy($C_1$-$C_6$)alkoxy include, but are not limited to, methoxymethoxy, propoxymethoxy, 2-methoxyethoxy, 2-ethoxyethoxy, 2-butoxyethoxy, 2,2-dimethoxyethoxy, 1-methyl-2-propoxyethoxy, 2-methoxypropoxy, and 4-methoxybutoxy.

The term "($C_1$-$C_6$)alkoxy($C_1$-$C_6$)alkoxy($C_1$-$C_6$)alkyl", as employed herein as such or as part of another group, refers to an ($C_1$-$C_6$)alkoxy($C_1$-$C_6$)alkoxy group, as defined herein, appended to the parent molecular moiety through an ($C_1$-$C_6$) alkyl group, as defined herein.

The term "phenyl", as employed herein as such or as part of another group, refers to 6 membered aromatic carbocyclic ring which can be unsubstituted or substituted with 1 or 2 substituent(s) each independently being hydroxy, halogen, ($C_1$-$C_4$)alkyl, ($C_1$-$C_4$)alkoxy, or halo($C_1$-$C_4$)alkyl.

The term "heteroaryl", as employed herein as such or as part of another group, refers to 3 to 7 membered aromatic monocyclic ring system, containing one to three heteroatom(s) selected from oxygen, nitrogen and sulphur. Said heteroaryl can be unsubstituted or substituted with 1 or 2 substituent(s) each independently being hydroxy, halogen, oxo, ($C_1$-$C_4$)alkyl, ($C_1$-$C_4$)alkoxy, or halo($C_1$-$C_4$)alkyl. Representative examples of heteroaryl include, but are not limited to furanyl, thiophenyl, and pyrazolyl.

The term "heteroaryl($C_1$-$C_6$)alkyl", as employed herein as such or as part of another group, refers to an heteroaryl, as defined herein, appended to the parent molecular moiety through an ($C_1$-$C_6$)alkyl group, as defined herein.

The term "($C_2$-$C_6$)alkenyloxy", as employed herein as part of another group, refers to an ($C_2$-$C_6$)alkenyl group, as defined herein, appended to the parent molecular moiety through an oxygen atom. Representative examples of ($C_2$-$C_6$) alkenyloxy include, but are not limited to, ethenyloxy, prop-2-enyloxy, bute-2-nyloxy, and hex-3-enyloxy.

The term "($C_2$-$C_6$)alkenyloxy($C_1$-$C_6$)alkenyl", as employed herein, refers to at least one ($C_2$-$C_6$)alkenyloxy group, as defined herein, appended to the parent molecular moiety through an ($C_2$-$C_6$)alkenyl group, as defined herein. When there are several ($C_2$-$C_6$)alkenyloxy groups, the ($C_2$-$C_6$)alkenyloxy groups can be identical or different. Representative examples of ($C_2$-$C_6$)alkenyloxy($C_2$-$C_6$)alkenyl include, but are not limited to, ethenyloxyethenyl, and prop-2-enyloxyethenyl.

The expression "compounds of the invention" as employed herein refers to the compounds of formula I.

The "pharmaceutically acceptable salts" according to the invention include therapeutically active, non-toxic base and acid salt forms, which the compounds of formula I are able to form with both organic and inorganic bases and acids. Representative examples of pharmaceutically acceptable base addition salt forms, for example, metal or amine salts, include, but are not limited to, ammonium salts, lithium, sodium, potassium, calcium, magnesium, aluminum and zinc salts, salts with organic bases, such as N-methyl-D-glucamine, hydrabamine salts and salts with amino acids, such as arginine, lysine, and the like. Representative examples of pharmaceutically acceptable acid addition salts include, but are not limited to, chlorides, bromides, sulfates, nitrates, phosphates, sulfonates, methane sulfonates, formates, tartrates, maleates, citrates, benzoates, salicylates, ascorbates, acetates, oxalates, fumarates, hemifumarates, and succinates.

Pharmaceutically acceptable esters, when applicable, may be prepared by known methods using pharmaceutically acceptable acids that are conventional in the field of pharmaceuticals and that retain the pharmacological properties of the free form. Non-limiting examples of these esters include esters of aliphatic or aromatic alcohols. Representative examples of pharmaceutically acceptable esters include, but are not limited to, methyl, ethyl, n-propyl, iso-propyl, n-butyl, iso-butyl, sec-butyl, tert-butyl, and benzyl esters.

The invention includes within its scope all the possible geometric isomers, for example Z and E isomers (cis and trans isomers), of the compounds of the invention as well as all the possible optical isomers, such as diastereomers and enantiomers, of the compounds of the invention. Furthermore, the invention includes in its scope both the individual isomers and any mixtures thereof, such as a racemic mixture. The individual isomers may be obtained using the corresponding isomeric forms of the starting material or they may be separated after the preparation of the end compound according to conventional separation methods. For the separation of optical isomers, such as enantiomers, from the mixture thereof, conventional resolution methods, for example, fractional crystallization or preparative chiral chromatography, may be used.

The compounds of formula I can be prepared by a variety of synthetic routes analogously or according to methods known in the literature using suitable starting materials, for example by reacting 2-phenylethanol or 2-phenylethanethiol with aldehyde or acetal, or according to other known methods (Larghi et al, *Synthesis*, 2006, 2, 187-220; Ishibashi et al, *J. Heterocyclic Chem* 1985, 22, 1527-1529.). The imidazolenes can be prepared, for example, by reacting ethane-1,2-diamine with ester or aldehydes (Gentili et al, *J. Med. Chem.*, 2003, 46, 2169-2176; Ishihara et al, *Synthesis*, 2007, 1939-1942).

The starting materials depicted below are commercially available or can be prepared via synthetic routes known in the literature, for example, by reduction of carboxylic acid, carboxylic ester or ketones, by opening of corresponding epoxide with metalled aromatic species, by enzymatic hydrolysis or by chiral separation of racemic alcohol. (Bunnet et al, *J. Org. Chem.*, 1962, 27, 3836-3843.; Mangas-Sánchez et al, *Organic Lett.*, 2010, 12, 3498-3501; Knölker et al, *Tetrahedron Lett.*, 2000, 41, 1171-1174.).

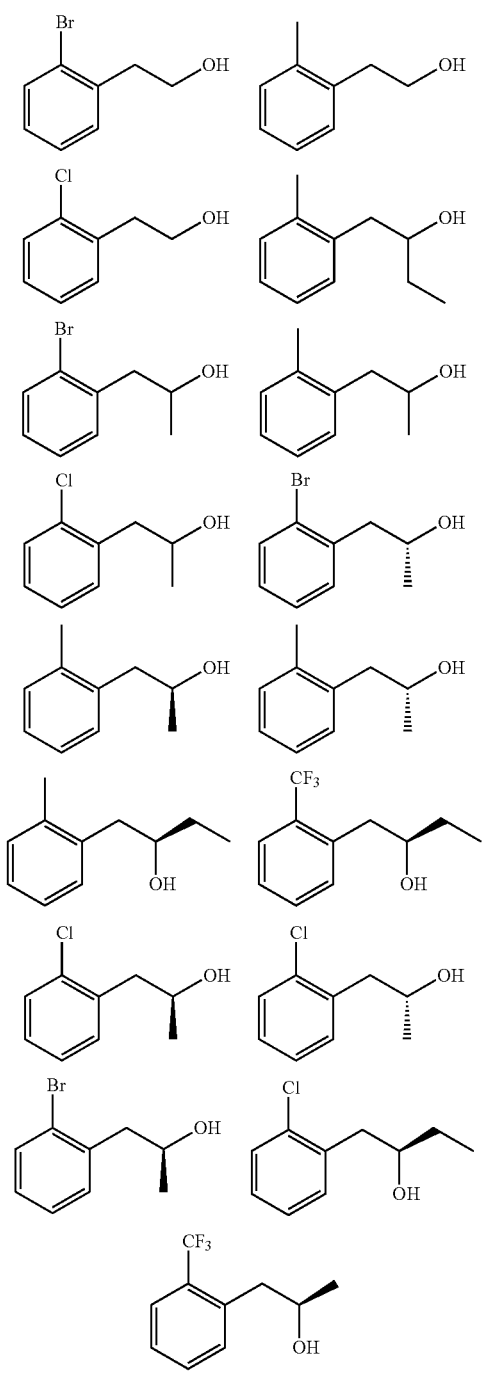

In general, compounds of formula I can be prepared analogously or according to the following scheme 1:

Scheme 1.

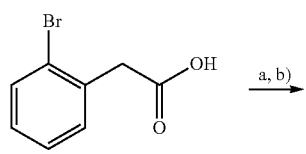

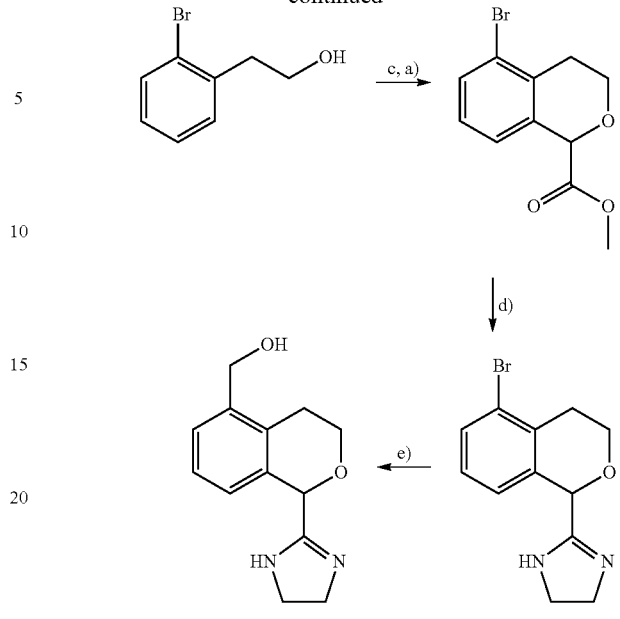

wherein a) SOCl$_2$, MeOH, b) NaBH$_4$, c) TFA, 2,2-dihydroxyacetic acid, d) ethylenediamine, Me$_3$Al, e) Pd(PPh$_3$)$_4$, HOCH$_2$SnBu$_3$.

A person skilled in the art realizes that any starting material or intermediate in the reactions described above can be protected, if necessary, in a manner known in the art. Any protected functionality can subsequently be deprotected in a manner known in the art.

The synthetic routes described above are meant to illustrate the preparation of the compounds of formula I and the preparation is by no means limited thereto, that is, there are also other possible synthetic methods which are within the general knowledge of a person skilled in the art.

The compounds of formula I may be converted, if desired, into their pharmaceutically acceptable salt or ester forms using methods known in the art.

The present invention will be explained in more detail by the following examples. The examples are meant for illustrating purposes only and do not limit the scope of the invention defined in the claims.

The following general abbreviations are used: EtOAc=acetic acid ethyl ester, DCM=dichloromethane, HCl=hydrochloric acid, MeOH=methanol, TFA=trifluoroacetic acid, THF=tetrahydrofurane, Et$_2$O=diethylether, SiO$_2$=commercial silicon dioxide for chromatographic purposes (CAS 112926-00-8 or similar), hrs=hours, RT=room temperature. Microwave heating was performed using microwave reactors from Biotage. The structures of the products were confirmed by $^1$H NMR. $^1$H NMR resonances were measured on a Bruker Avance II 400 MHz spectrometer and chemical shifts are quoted for selected compounds in parts-per-million (ppm) downfield relative to tetramethylsilane as internal standard.

Separation Method A

The reaction mixture was diluted with organic solvent (typically DCM or EtOAc) and washed with water or aqueous base (typically NH$_4$OH, NaHCO$_3$ or NaOH) and dried over the drying agent (typically Na$_2$SO$_4$ or K$_2$CO$_3$), filtrated and evaporated.

Separation Method B

The reaction mixture was diluted with organic solvent (typically DCM or EtOAc) and washed with water or aqueous acid (typically HCl or aqueus KHSO$_4$) and dried over the drying agent (typically Na$_2$SO$_4$ or K$_2$CO$_3$), filtrated and evaporated.

Separation Method C

The crude product was dissolved in organic solvent (typically DCM or EtOAc) and HCl solution in solvent (typically EtOAc or Et$_2$O) was added and the solvents were evaporated or the precipitated solid was filtered.

Separation Method D

The precipitated solid was filtered, washed or recrystalized in the defined solvent or mixture of solvets to give the title compound.

Separation Method E

The crude product was eluated through a column (commercial SiO$_2$ or CombiFlash instruments together with disposable Redisep columns from Teledyne ISCO) with mixture of solvent, typically EtOAc in heptan or MeOH in DCM eventually containing triethyl amine, ammonia or other basic modificator, from ratio 0/100/0 to 45/45/10, typically 5/94/1.

Separation Method F

The reaction mixture was applied to acidic ion-exchange column and the column was washed with MeOH. The compound was eluted with MeOH containing 10% aqueous NH$_3$, triethylamine or similar amine base, filtrated and evaporated.

Separation Method G

The crude product was eluated through a reversed phase column (typically combiFlash instrument together with disposable Redisep Rf 18 columns from Teledyne ISCO) with mixture of solvent. Typically, a gradient of water/acetonitrile or methanol with 0.1% ammonia or formic acid was used as eluent.

Separation Method H

Separation was performed with preparative HPLC with a Agilent HPLC/UV purification system equipped with a Chiracel IA column or OD-H column. Typically, an isocratic run of isopropanol/heptanes or hexanes from ratio 70/30 to 99/1 with 0.1% diethylamine or 0.1% TFA was used as eluent.

Separation Method I

Residue was taken in basic aqueous solution (typically NH$_4$OH, NaHCO$_3$ or NaOH) and the solution was washed with organic solvent (typically EtOAc, DCM or Et$_2$O). The aqueous phase was then made acidic by addition of acid (typically HCl) and extracted with organic solvent (typically Et$_2$O, EtOAc or DCM). The extract was dried (typically Na$_2$SO$_4$ or K$_2$CO$_3$), filtered and evaporated.

Separation Method J

Residue was taken in acidic aqueous solution (typically HCl) and the solution was washed with organic solvent (typically EtOAc, DCM or Et$_2$O). The aqueous phase was then made basic by addition of basic aqueous solution (typically NH$_4$OH, NaHCO$_3$ or NaOH) and extracted with organic solvent (typically Et$_2$O, EtOAc or DCM). The extract was dried (typically Na$_2$SO$_4$ or K$_2$CO$_3$), filtered and evaporated.

Separation Method K

The reaction mixture was evaporated to dryness and dissolved in MeOH. This was applied to pre-washed (MeOH) thiourea column. The compound was eluted with MeOH and evaporated.

Separation Method L

The enaniomers were separated with preparative HPLC/UV purification system equipped with a Phenomenex LUX amylase-2 column. Typically, an isocratic run of n-hexane/ethanol/formic acid 70/30/0.1 was used as eluent and fractions were acidified immediately after collection with aqueous HCl.

Separation Method M

Separation was performed with Thar SFC 80 preparative supercritical fluid HPLC system typically equipped with a Chiralpak AD-H column. Typically, an isocratic run of carbondioxane/methanol 93/7 or 90/10 was used as eluent.

PREPARATION OF THE COMPOUNDS OF INVENTION

Example 1

2-(5-Methylisochroman-1-yl)-4,5-dihydro-1H-imidazole

Synthesis Method A
Synthesis Method A1: 5-Methylisochroman-1-carboxylic acid

The mixture of 2-(2-methylphenyl)ethanol (2 g), TFA (10 ml) and 2,2-dihydroxyacetic acid (1.5 g) was refluxed for 23 hrs and volatiles were evaporated. Separation method I yielded the title compound (2.6 g) as an off-white solid. Alternatively, sulphuric acid can be used in cyclization.

Synthesis Method A2: Methyl 5-methylisochroman-1-carboxylate

The mixture of 5-methylisochroman-1-carboxylic acid (1 g), methanol (20 ml) and trimethylsilylchloride (2 ml) was stirred for 1.5 hrs and volatiles evaporated. Separation method E yielded the title compound (0.5 g) as yellowish oil. Alternatively sulphuric acid can be used instead of trimethylsilylchloride.

Synthesis Method A3: 2-(5-Methylisochroman-1-yl)-4,5-dihydro-1H-imidazole

To 10 minutes ice-bath cooled and stirred solution of ethylenediamine (0.29 ml), trimethylaluminum (2M heptane sol, 2.2 ml) and toluene (10 ml) was added the mixture of methyl 7-bromoisochroman-1-carboxylate (0.5 g) and toluene (10 ml) and the reaction mixture was refluxed for 6 hrs. Water (2 ml), methanol (5 ml) and DCM (5 ml) were added, mixture refluxed for 15 min and participate was filtered off. Organics were evaporated and the title compound (0.38 g) was isolated with the separation method D (2-methoxy-2-methylpropane/MeOH).

$^1$H NMR (CDCl$_3$) δ ppm 7.16 (s, 1H), 7.02 (s, 2H), 5.42 (s, 1H), 4.20 (ddd, 1H), 3.94 (br s, 1H), 3.84 (td, 2H), 3.39 (br s, 2H), 3.03 (ddd, 1H), 2.68 (d, 1H), 2.30 (s, 3H).

Example 2

2-(5-Bromoisochroman-1-yl)-4,5-dihydro-1H-imidazole

The title compound was prepared from 2-(2-bromophenyl)ethanol (200 mg) using the procedure of synthesis method A and separation methods A and E. (Yield 80 mg).

$^1$H NMR (CDCl$_3$) δ ppm 7.45 (d, 1H), 7.30 (d, 1H), 6.99-7.10 (m, 1H), 5.72 (s, 1H), 4.19 (ddd, 1H), 3.67-3.84 (m, 5H), 2.69-2.93 (m, 2H).

Example 3

2-(1,5-Dimethylisochroman-1-yl)-4,5-dihydro-1H-imidazole

The mixture of NaH (0.77 g), methyl-5-methylisochroman-1-carboxylate (3 g, synthesis method A) and THF (40 ml) was stirred 75 min in ice-bath temperature, iodomethane (2.3 ml) was added and the mixture was stirred at ambient temperature for 3 hrs. The intermediate methyl 1,5-dimethylisochroman-1-carboxylate (2.5 g) was purified with separation method A and the title compound was synthesized using the procedure of synthesis method A step 3 and separation method D (2-propanol/heptanes). (Yield 1.0 g).

$^1$H NMR (CD$_3$OD) δ ppm 7.00-7.18 (m, 3H), 3.99 (t, 2H), 3.54 (br s, 4H), 2.62-2.87 (m, 2H), 2.24 (s, 3H), 1.70 (s, 3H).

Example 4

2-(5-Chloroisochroman-1-yl)-4,5-dihydro-1H-imidazole

Synthesis Method B

The mixture of 2-(2-chlorophenyl)ethanol (1.0 g), ethyl 2,2-diethoxyacetate (1.7 g), titanium(IV)chloride (2.0 ml) and 1,2-dichloroethane (15 ml) was refluxed 1 hr. The intermediate ethyl 5-chloroisochroman-1-carboxylate was purified with separation methods B and E (0.41 g) and the title compound was synthesized using the procedure of synthesis method A3. Alternative boron trifluoride diethyletherate can be used instead of titanium(IV)chloride. (Yield 0.36 g).

$^1$H NMR (CDCl$_3$) δ ppm 7.20-7.40 (m, 2H, CHCl3), 7.09-7.20 (m, 1H), 5.41 (s, 1H), 4.23 (ddd, 1H), 3.77-4.00 (m, 3H), 3.28-3.51 (m, 2H), 2.77-3.01 (m, 2H).

Example 5

1-(4,5-Dihydro-1H-imidazol-2-yl)isochroman-5-carbonitrile

A mixture of 2-(5-chloroisochroman-1-yl)-4,5-dihydro-1H-imidazole (50 mg), dicyanozinc (25 mg), bis(tri-t-butylphosphine)palladium(0) (3 mg) and DMF (2 ml) was stirred in microwave reactor at 160° C. for 30 minutes. The title compound was purified with separation methods F and G. (Yield 22 mg).

$^1$H NMR (CD$_3$OD) δ ppm 7.63 (dd, 1H), 7.53 (d, 1H), 7.35 (t, 1H), 4.26 (ddd, 1H), 3.92 (ddd, 1H), 3.51-3.72 (m, 4H), 3.07-3.22 (m, 1H), 2.89-3.03 (m, 1H).

Example 6

2-(5-Allylisochroman-1-yl)-4,5-dihydro-1H-imidazole

Synthesis Method C

To a mixture of 2-(5-chloroisochroman-1-yl)-4,5-dihydro-1H-imidazole (50 mg), allyltributyltin (69.9 mg), CsF (70.6 mg) and bis(tri-t-butylphosphine)palladium (3.24 mg) were added dioxane (2 ml) and DMF (0.5 ml). The reaction mixture was degassed with N$_2$ and heated in a microwave oven for 30 min at 160° C. The title compound was purified by applying methods F and G. (Yield 5.8 mg).

$^1$H NMR (CD$_3$OD) δ ppm 6.96-7.21 (m, 3H), 5.94 (ddt, 1H), 4.92-5.08 (m, 2H), 4.22 (ddd, 1H), 3.81 (ddd, 1H), 3.52 (s, 4H), 3.34-3.35 (m, 2H), 2.93 (ddd, 1H), 2.72 (dt, 1H).

Example 7

2-(5-Vinylisochroman-1-yl)-4,5-dihydro-1H-imidazole

The title compound was prepared from 2-(5-bromoisochroman-1-yl)-4,5-dihydro-1H-imidazole (100 mg) using the procedure of synthesis method C and purified with separation methods F and G. (Yield 5 mg).

$^1$H NMR (CDCl$_3$) δ ppm 7.38-7.48 (m, 1H), 7.15-7.30 (m, 1H, CHCl$_3$), 6.80-7.05 (m, 2H), 5.74 (dd, 1H), 5.35 (dd, 1H), 4.25 (ddd, 1H), 3.50-3.85 (m, 5H), 2.80-3.10 (m, 1H), 2.72-2.85 (m, 1H).

Example 8

2-(5-Ethylisochroman-1-yl)-4,5-dihydro-1H-imidazole

Synthesis Method D

To a mixture of 2-(5-bromoisochroman-1-yl)-4,5-dihydro-1H-imidazole (100 mg), ethylboronic acid (56.2 mg), (1,1'-bis(diphenylphosphino)ferrocene)dichloropalladium(II), complex with CH$_2$Cl$_2$ (1:1) (13 mg) and CsF (108 mg) was added dioxane (4 ml) and DMF (1 ml). The mixture was degassed with N$_2$ and heated in a microwave oven for 30 min at 100° C. and 30 min at 150° C. The title compound was purified by separation methods J and G. (Yield 6.1 mg).

$^1$H NMR (CD$_3$OD) δ ppm 6.96-7.17 (m, 3H), 5.39 (s, 1H), 4.24 (ddd, 1H), 3.77-3.89 (m, 1H), 3.49-3.69 (m, 4H), 2.87-3.01 (m, 1H), 2.73 (dt, 1H), 2.63 (q, 2H), 1.20 (t, 3H).

Example 8 HCl Salt 2-(5-Ethylisochroman-1-yl)-4,5-dihydro-1H-imidazole hydrochloride Salt Formation Method A To the compound of example 8 (1 g) in ethanol (15 ml) was added 4M hydrogen chloride in dioxane (160 mg) and the mixture was heated to reflux, allowed to cool and evaporated yielding the title compound (1.1 g). Alternative other solvents, temperatures and hydrogen chloride sources could be used, or product filtrated from solution or washed with other organic solvents.

$^1$H NMR (DMSO-d$_6$) δ ppm 10.72 (s, 2H), 7.14-7.24 (m, 3H), 5.91 (s, 1H), 4.16-4.21 (m, 1H), 3.78-3.90 (m, 5H), 2.89-2.96 (m, 1H), 2.69-2.78 (m, 1H), 2.60 (q, 2H), 1.51 (tr, 3H).

Example 8 Sulfate Salt 2-(5-Ethylisochroman-1 yl)-4,5-dihydro-1H-imidazole sulfate Salt Formation Method B To the compound of example 8 (1.5 g) in ethanol (30 ml) was added sulfuric acid (440 mg) in ethanol (7.5 ml) and the mixture was heated to reflux, allowed to cool, evaporated and washed with acetone yielding the title compound (1.4 g). Alternative other solvents and temperatures could be used, or product filtrated from solution or washed with other organic solvents.

$^1$H NMR (DMSO-d$_6$) δ ppm 7.13-7.25 (m, 2H), 7.05 (dd, 1H), 5.61 (s, 1H), 4.08-4.19 (m, 1H), 3.71 (br. s, 4H), 3.78-3.93 (m, 1H), 2.78-2.90 (m, 1H), 2.68-2.78 (m, 1H), 2.59 (q, 2H), 1.07-1.21 (m, 3H).

Example 8 Fumarate Salt 2-(5-Ethylisochroman-1-yl)-4,5-dihydro-1H-imidazole fumarate Salt Formation Method C To the compound of example 8 (2.3 g) in ethanol (15 ml) was added fumaric acid (1.16 g) in ethanol (5 ml) and the mixture was heated to reflux, allowed to cool, evaporated and washed with TBME yielding the title compound (3.0 g). Alternative other solvents and temperatures could be used, or product filtrated from solution or washed with other organic solvents.

$^1$H NMR (DMSO-$d_6$) δ ppm 7.15-7.20 (m, 2H), 7.05-7.09 (m, 1H), 6.48 (s, 2H), 5.72 (s, 1H), 4.14-4.19 (m, 1H), 3.80-3.86 (m, 1H), 3.71 (s, 4H), 2.83-2.91 (m, 1H), 2.67-2.75 (m, 1H), 2.58 (q, 2H), 1.15 (tr, 3H).

Example 9

1-(4,5-Dihydro-1H-imidazol-2-yl)isochroman-5-ol

A mixture of 2-(5-bromoisochroman-1-yl)-4,5-dihydro-1H-imidazole (720 mg), bis(pinacolato)diboron (715 mg) bis(tri-t-butylphosphine)palladium(0) (39 mg), potassiumacetate (503 mg), dioxane (9 ml) and DMF (0.75 ml) was stirred under inert atmosphere in microwave reactor at 160° C. for 30 minutes. Additional bis(tri-t-butylphosphine)palladium(0) (21 mg) was added and heating continued for 15 minutes. The intermediate 2-(5-(4,4,5,5-tetramethyl-1,3,2-dioxaborolan-2-yl)isochroman-1-yl)-4,5-dihydro-1H-imidazole (680 mg) was purified with separation method A and stirred with EtOAc (2 ml), water (2 mil) and hydrogen peroxide (35%, 0.07 ml) at ice bath temperature for 2 hrs. The title compound was purified with separation methods A and E. (Yield 45 mg).

$^1$H NMR (DMSO-$d_6$) δ ppm 9.44 (s, 1H), 6.78-7.08 (m, 1H), 6.62 (d, 1H), 6.67 (d, 1H), 5.22 (s, 1H), 4.05-4.15 (m, 1H), 3.70-3.78 (m, 1H), 3.18-3.42 (m, 4H, $H_2O$), 2.53-2.69 (m, 2H).

Example 10

(1-(4,5-Dihydro-1H-imidazol-2-yl)isochroman-5-yl)methanol

The title compound was prepared from 2-(5-bromoisochroman-1-yl)-4,5-dihydro-1H-imidazole (50 mg) and (tributylstannyl)methanol (86 mg) by using tetrakis(triphenylphosphine)palladium (10.28 mg) as catalyst, and the procedure of synthesis method C and separation methods F and G. (Yield 6.2 mg).

$^1$H NMR ($CD_3OD$) δ ppm 7.31 (d, 1H), 7.11-7.22 (m, 2H), 5.42 (s, 1H), 4.62 (s, 2H), 4.22 (td, 1H), 3.86 (dd, 1H), 3.54-3.69 (m, 4H), 2.93-3.05 (m, 1H), 2.75-2.86 (m, 1H).

Example 11

2-(5-Bromo-1-methylisochroman-1-yl)-4,5-dihydro-1H-imidazole

The mixture of NaH (0.024 g), ethyl 5-bromoisochroman-1-carboxylate (0.2 g, synthesis method B) and THF (5 ml) was stirred 90 min in ice-bath temperature, iodomethane (0.06 ml) was added and the mixture stirred at ambient temperature for 16 hrs. The intermediate ethyl 5-bromo-1-methylisochroman-1-carboxylate (0.11 g) was purified with separation method A, and the title compound was synthesized using the procedure of synthesis method A3 and separation method E (DCM/EtOAc/$Et_3N$). (Yield 0.07 g).

$^1$H NMR ($CDCl_3$) δ ppm 7.45-7.47 (m, 1H), 7.39-7.41 (m, 1H), 7.07-7.11 (m, 1H), 4.70-5.20 (br s, 1H), 3.94-4.05 (m, 2H), 3.22-3.87 (m, 2H), 2.83-2.87 (m, 2H), 1.77 (s, 3H).

Example 12

2-((3R)-5-chloro-3-ethylisochroman-1-yl)-4,5-dihydro-1H-imidazole

The title compound was prepared from (R)-1-(2-chlorophenyl)butan-2-ol (400 mg) using the procedure of synthesis methods B and A3. Intermediate (3R)-ethyl 5-chloro-3-ethylisochroman-1-carboxylate was purified with separation methods B (EtOAc/Heptane) and E. (Yield 235 mg).

$^1$H NMR (DMSO-$d_6$) δ ppm 7.28-7.43 (m, 1H), 7.11-7.26 (m, 2H), 6.12 (br s, 1H), 5.35 (s, 1H), 3.53-3.80 (m, 3H), 3.12-3.29 (m, 2H), 2.73-2.92 (m, 1H), 1.67 (m, 2H), 0.99 (t, 3H).

Example 13

1-(1-(4,5-Dihydro-1H-imidazol-2-yl)-1-methylisochroman-5-yl)-2,2-dimethylpropan-1-ol, slower eluting isomer To a solution of 2-(5-bromo-1-methylisochroman-1-yl)-4,5-dihydro-1H-imidazole (Example 2, 0.075 g) in 2 ml of THF was added 0.33 ml of tert-butyl lithium solution in pentane (1.7M) at −78° C. followed by addition of 1.2 ml of 20.8M solution of trimethylacetaldehyde in THF. After stirring at −78° C. for 15 min, the reaction was quenched with ice. The title compound was isolated with separation methods A and G. (Yield 0.003 g).

$^1$H NMR ($CDCl_3$) δ ppm 7.43-7.45 (m, 1H), 7.34-7.36 (m, 1H), 7.22-7.24 (m, 1H), 4.73 (s, 1H), 3.88-4.05 (m, 2H), 3.61 (br s, 4H), 2.84-2.91 (m, 2H), 1.78 (s, 3H), 0.97 (s, 9H).

Example 14

1-(1-(4,5-Dihydro-1H-imidazol-2-yl)-1-methylisochroman-5-yl)-2,2-dimethylpropan-1-ol, faster eluting isomer The title compound was isolated in the synthesis of the example 13 with separation methods A and G. (Yield 0.007 g).

$^1$H NMR ($CDCl_3$) δ ppm 7.46 (d, 1H), 7.50 (d, 1H), 7.18-7.35 (m, 3H), 4.72 (s, 1H), 4.04 (s, 1H), 3.59-3.81 (m, 3H), 2.81-3.02 (m, 2H), 2.05 (d, 1H), 1.89 (s, 3H), 0.86-1.05 (m, 9H).

Example 15

2-(5-Ethynylisochroman-1-yl)-4,5-dihydro-1H-imidazole

To a degassed solution of 2-(5-bromoisochroman-1-yl)-4,5-dihydro-1H-imidazole (300 mg) in $Et_3N$ (10 ml) and ethynyltrimethylsilane (210 mg) was added tetrakis(triphenylphosphine)-palladium (37 mg). The mixture was degassed with $N_2$ and heated in a microwave oven for 60 min at 120° C. The reaction mixture was concentrated under vacuum and purified by separation method K. $K_2CO_3$ was added to the reaction crude (in MeOH) and the mixture was stirred 4 h at it. The title compound was isolated by a separation method G. (Yield 6.2 mg).

$^1$H NMR ($CDCl_3$) δ ppm 7.42-7.37 (m, 2H), 7.17 (t, 1H), 5.42 (s, 1H), 4.78 (s, 1H), 4.26-4.21 (m, 1H), 4.00-3.73 (m, 4H), 3.08-2.93 (m, 2H).

Example 16

2-((3R)-3-ethyl-5-(trifluoromethyl)isochroman-1-yl)-4,5-dihydro-1H-imidazole Step 1: (R)-1-(2-(trifluoromethyl)phenyl)butan-2-ol 2-Iodobenzotrifluoride (3 g) was dissolved in THF (18 ml) and was cooled to −78° C. n-BuLi (2.5 M in hexanes, 13.23 ml) was added dropwise to the reaction mixture. After 1 h, (R)-(+)-1,2-epoxybutane (1.4 ml) in THF (18 ml) was added. The reaction temperature was slowly increased to rt. The mixture was poured into ice-water (100 ml), and the product was extracted with heptane. The organic phase was washed with brine and water, dried ($Na_2SO_4$) ja evaporated under vacuum. The title compound was obtained by separation method E. (Yield 1.05 g).

Step 2: 2-((3R)-3-ethyl-5-(trifluoromethyl)isochroman-1-yl)-4,5-dihydro-1H-imidazole The title compound was prepared from (R)-1-(2-(trifluoromethyl)phenyl)butan-2-ol (570 mg) using the procedure of synthesis methods B and A3. Intermediate (3R)-ethyl 5-trifluoromethyl-3-ethylisochroman-1-carboxylate was purified with separation methods B (EtOAc/Heptane) and E. (Yield 360 mg).

$^1$H NMR ($CD_3OD$) δ ppm 7.59 (d, 1H), 7.50 (d, 1H), 7.25-7.42 (m, 1H), 5.49 (s, 1H), 3.46-3.72 (m, 5H), 2.98 (d, 1H), 2.82 (dd, 1H), 1.59-1.84 (m, 2H), 0.97-1.18 (m, 3H).

Example 17

2-(5-Methoxyisochroman-1-yl)-4,5-dihydro-1H-imidazole

Synthesis Method E

To a mixture of 2-(5-bromoisochroman-1-yl)-4,5-dihydro-1H-imidazole (200 mg), 2-(di-t-butylphosphino)biphenyl (5.31 mg), palladium(II)acetate (3.19 mg) and $Cs_2CO_3$ (348 mg) was added methanol (1 ml) and toluene (2 ml). The mixture was degassed with $N_2$ and then heated for 40 min at 120° C. and 30 min at 130° C. Alternatively, other Pd-ligand complexes and reaction conditions can be applied in the C—O formation. The title compound was purified by using separation methods E and G. (Yield 5 mg).

$^1$H NMR ($CD_3OD$) δ ppm 7.14 (t, 1H), 6.80 (d, 1H), 6.83 (d, 1H), 5.34 (s, 0.3H), 4.16-4.31 (m, 1H), 3.74-3.89 (m, 4H), 3.50-3.68 (m, 4H), 2.61-2.90 (m, 2H).

Example 17 HCl Salt 2-(5-Methoxyisochroman-1-yl)-4,5-dihydro-1H-imidazole hydrochloride The title compound was prepared from compound of example 17 (263 mg) as described in the example 8 ($Et_2O$, yield 148 mg).

$^1$H NMR ($CD_3OD$) δ ppm 7.28 (t, 1H), 6.97 (d, 1H), 6.80 (d, 1H), 5.72 (s, 1H), 4.12-4.19 (m, 1H), 3.99 (br.s, 4H), 3.87-3.95 (m, 1H), 3.86 (s, 3H), 2.78-2.84 (m, 2H).

Example 17 Sulfate Salt 2-(5-Methoxyisochroman-1-yl)-4,5-dihydro-1H-imidazole sulfate The title compound was prepared from compound of example 17 (50 mg) as described in the example 8 (EtOH, yield 41.5 mg).

$^1$H NMR (DMSO-$d_6$) δ ppm 9.37-10.57 (br, 2H), 7.27 (t, 1H), 6.99 (d, 1H), 6.79 (d, 1H), 5.75 (s, 1H), 4.03-4.20 (m, 1H), 3.85-3.94 (m, 5H), 3.82 (s, 3H), 2.65-2.79 (m, 2H).

Example 17 Hemifumarate Salt 2-(5-Methoxyisochroman-1-yl)-4,5-dihydro-1H-imidazole hemifumarate The title compound was prepared from compound of example 17 (50 mg) as described in the example 8 (EtOH, yield 38 mg).

$^1$H NMR (DMSO-$d_6$) δ ppm 7.16 (t, 1H), 6.88 (d, 1H), 6.79 (d, 1H), 6.43 (s, 1H), 5.47 (s, 1H), 4.07-4.16 (m, 1H), 3.73-3.82 (m, 4H), 3.40-4.75 (br.s, 4H), 2.58-2.75 (m, 2H).

Example 18

2-(5-Iodoisochroman-1-yl)-4,5-dihydro-1H-imidazole

The title compound was prepared from 2-(2-iodophenyl)ethanol (1.5 g) using the procedure of synthesis method B and separation method D. (Yield 510 mg).

$^1$H NMR ($CD_3OD$) δ ppm 7.72-7.84 (m, 1H), 7.24 (d, 1H), 6.94 (t, 1H), 4.21 (ddd, 1H), 3.83 (ddd, 1H), 3.46-3.68 (m, 4H), 2.80-2.95 (m, 1H), 2.56-2.74 (m, 1H).

Example 19

2-((3R)-3-methyl-5-(trifluoromethyl)isochroman-1-yl)-4,5-dihydro-1H-imidazole The title compound was prepared from (R)-1-(2-(trifluoromethyl)phenyl)propan-2-ol (570 mg) using the procedure of synthesis methods B and A3. Starting material (R)-1-(2-(trifluoromethyl)phenyl)propan-2-ol (1.0 g) was prepared from 2-iodobenzotrifuoride and (R)-(+)-propyleneoxide in a similar way that described in the example 16. Intermediate (3R)-ethyl 5-trifluoromethyl-3-ethylisochroman-1-carboxylate was purified with separation methods B (EtOAc/Heptane) and E. (Yield 340 mg).

$^1$H NMR ($CD_3OD$) δ ppm 7.59 (d, 1H), 7.50 (d, 1H), 7.29-7.43 (m, 1H), 5.51 (s, 1H), 3.83-3.97 (m, 1H), 3.49-3.72 (m, 4H), 2.99 (d, 1H), 2.82 (dd, 1H), 1.25-1.48 (m, 3H).

Example 20

2-(5-Bromo-4-methylisochroman-1-yl)-4,5-dihydro-1H-imidazole

The title compound was prepared from 2-(2-bromophenyl)propan-1-ol (1.55 g) using the procedure of synthesis method B and separation method E. (Yield 70 mg).

$^1$H NMR ($CD_3OD$) δ ppm 7.43-7.55 (m, 1H), 7.27 (d, 0.6H), 7.04-7.15 (m, 1.4H), 5.34 (s, 0.5H), 3.98-4.10 (m, 1H), 3.75-3.92 (m, 1H), 3.53-3.67 (m, 4H), 2.94-3.06 (m, 1H), 1.45 (d, 1.9H), 1.33 (d, 1.1H).

Example 21

2-(1,5-Dimethylisochroman-1-yl)-4,5-dihydro-1H-imidazole, faster eluting isomer The title compound was prepared from 2-(1,5-dimethylisochroman-1-yl)-4,5-dihydro-1H-imidazole (Example 3, 70 mg) using the procedure of separation method H. (Yield 22 mg).

¹H NMR (CDCl₃) δ ppm 7.19-7.40 (m, 1H, CHCl₃), 7.02-7.19 (m, 2H), 3.90-4.15 (m, 2H), 2.66-2.81 (m, 2H), 2.24 (m, 3H), 1.79 (s, 3H).

Example 22

2-(1,5-Dimethylisochroman-1-yl)-4,5-dihydro-1H-imidazole, slower eluting isomer The title compound was prepared from 2-(1,5-dimethylisochroman-1-yl)-4,5-dihydro-1H-imidazole (Example 3, 70 mg) using the procedure of separation method H. (Yield 9 mg).
¹H NMR (CDCl₃) δ ppm 7.21-7.36 (m, 1H, CHCl₃), 7.01-7.18 (m, 2H), 3.91-4.15 (m, 2H), 2.60-2.83 (m, 2H), 2.24 (s, 3H), 1.79 (s, 3H).

Example 23

2-((3R)-1,3,5-trimethylisochroman-1-yl)-4,5-dihydro-1H-imidazole

The title compound was prepared from (3R)-methyl 3,5-dimethylisochroman-1-carboxylate (454 mg, example 33 intermediate) using the procedure of example 11 and separation method E (DCM/EtOAc/Et3N). (Yield 232 mg).
¹H NMR (DMSO-d₆) δ ppm 7.12-7.23 (m, 1H), 6.93-7.12 (m, 2H), 6.15 (s, 0.5H), 5.83 (s, 0.5H), 3.87-4.02 (m, 0.5H), 3.61-3.86 (m, 1H), 3.40-3.61 (m, 1.5H), 3.04-3.29 (m, 2H), 2.53-2.71 (m, 1H), 2.27-2.48 (m, 1H), 2.18 (s, 1.5H), 2.16 (s, 1.5H), 1.64 (s, 1.5H), 1.56 (s, 1.5H), 1.23-1.38 (m, 3H).

Example 24

2-(5-Cyclopropylisochroman-1-yl)-4,5-dihydro-1H-imidazole

The mixture of 2-(5-bromo-1-methylisochroman-1-yl)-4,5-dihydro-1H-imidazole (Example 11, 0.15 g), sodium carbonate (0.27 g), bis(triphenylphosphine)palladium(II) chloride (0.02 g), cyclopropylboronic acid (0.09 g), water (1 ml), and acetonitrile (2 ml) was heated in a microwave oven at 120° C. for 15 min. The title compound was purified with separation methods A and G. (Yield 8 mg).
¹H NMR (CDCl₃) δ ppm 7.26-7.28 (d, 1H), 7.11-7.15 (tr, 1H), 6.92-6.94 (d, 1H), 4.03-4.06 (m, 2H), 3.62 (br s, 4H), 2.95-2.98 (m, 2H), 1.80 (s, 3H), 0.87-0.96 (br m, 2H), 0.58-0.69 (br m, 2H).

Example 25

2-(3,5-Dimethylisochroman-1-yl)-4,5-dihydro-1H-imidazole

The title compound was prepared from 1-o-tolylpropan-2-ol (800 mg) using the procedure of synthesis method B and separation methods E and D. (Yield 19.2 mg).
¹H NMR (CD₃OD) δ ppm 6.98-7.11 (m, 3H), 5.43 (s, 1H), 3.88 (dd, 1H), 3.49-3.67 (m, 4H), 2.64-2.76 (m, 1H), 2.57 (d, 1H), 2.23 (s, 3H), 1.39 (d, 3H).

Example 26

2-(5-Chloro-3-methylisochroman-1-yl)-4,5-dihydro-1H-imidazole

The title compound was prepared from 1-(2-chlorophenyl)propan-2-ol (1.0 g) using the procedure of synthesis method A and separation methods D (Et₂O, heptane). (Yield 0.077 g).

¹H NMR (DMSO-d₆) δ ppm 7.32-7.37 (m, 1H), 7.14-7.23 (m, 2H), 6.23 (br s, 1H), 5.36 (s, 1H), 3.83-3.91 (br m, 1H), 3.43 (br s, 4H), 2.82-2.89 (m, 1H), 2.46-2.53 (m, 1H), 1.29-1.34 (dd, 3H).

Example 27

2-(3-Ethyl-5-methylisochroman-1-yl)-4,5-dihydro-1H-imidazole

The title compound was prepared from 1-o-tolylbutan-2-ol (1 g) using the procedure of synthesis method B and separation methods E and D. (Yield 16.4 mg).
¹H NMR (CD₃OD) δ ppm 6.93-7.11 (m, 3H), 5.41 (s, 1H), 3.45-3.72 (m, 6H), 2.71 (dd, 1H), 2.55 (dd, 1H), 2.17-2.26 (m, 3H), 1.62-1.78 (m, 2H), 0.98-1.14 (m, 3H).

Example 28

2-(5-Chloro-1,3-dimethylisochroman-1-yl)-4,5-dihydro-1H-imidazole

The mixture of NaH (0.36 g), methyl 5-chloro-3-methyl-isochroman-1-carboxylate (1.1 g, synthesis method A) and THF (20 ml) was stirred 60 min in ice-bath temperature, iodomethane (0.9 ml) was added and the mixture stirred at ambient temperature for 16 hrs. The intermediate methyl 5-chloro-1,3-dimethylisochroman-1-carboxylate (0.95 g) was purified with separation method A and the title compound was synthesized using the procedure of synthesis method A and separation method A. (Yield 0.1 g).
¹H NMR (DMSO-d₆) δ ppm 7.16-7.33 (m, 3H), 6.14 (br s, 1H), 3.72-4.02 (br m, 1H), 3.40-3.47 (br s, 2H), 2.76-2.86 (br s, 1H), 2.35-2.54 (br m, 1H), 1.60-1.66 (d, 3H), 1.30-1.32 (dd, 3H).

Example 29

2-(5-Bromo-3-methylisochroman-1-yl)-4,5-dihydro-1H-imidazole

The title compound was prepared from 1-(2-bromophenyl)propan-2-ol (2.5 g) using the procedure of synthesis method A (43% of prepared methyl 5-bromo-3-methyl-isochroman-1-carboxylate was used in the last step) and separation method D. (Yield 447 mg).
¹H NMR (CD₃OD) δ ppm 7.42-7.55 (m, 1H), 7.24 (d, 0.8H), 7.02-7.17 (m, 1.2H), 5.41 (s, 0.7H), 4.08 (s, 0.2H), 3.81-3.95 (m, 0.8H), 3.50-3.70 (m, 4H), 2.82-2.93 (m, 1H), 2.40-2.64 (m, 1H), 1.38-1.44 (m, 2.3H), 1.34 (d, 0.7H).

Example 30

2-(1,3,5-Trimethylisochroman-1-yl)-4,5-dihydro-1H-imidazole

The title compound was prepared from 1-o-tolylpropan-2-ol (0.9 g) using the methodology as described in example 12 with the exception of using separation methods A and D (Et₂O and heptanes) in the final synthesis step. (Yield 0.012 g).
¹H NMR (DMSO-d6) δ ppm 7.27-7.29 (d, 1H), 7.13-7.17 (tr, 1H), 7.05-7.07 (d, 1H), 4.85 (br s, 1H), 3.82-3.90 (m, 1H), 3.64 (br s, 4H), 2.59-2.64 (m, 1H), 2.44-2.51 (m, 1H), 2.21-2.23 (m, 3H), 1.72 (s, 3H), 1.37-1.38 (d, 3H).

Example 31

2-(5-Bromo-1,3-dimethylisochroman-1-yl)-4,5-dihydro-1H-imidazole

The title compound was prepared from 1-(2-bromophenyl)propan-2-ol (2.5 g) using the procedure of synthesis method A. After the first two steps, 43% (500 mg) of the prepared methyl 5-bromo-3-methyl-isochroman-1-carboxylate was dissolved in THF (5 ml). NaH (140 mg) was added to the solution and then the mixture was stirred at ice-bath temperature. After 60 min iodomethane (0.325 ml) was added and the mixture stirred at ambient temperature for 48 hrs. The intermediate methyl 5-bromo-1,3-dimethylisochroman-1-carboxylate was purified with separation methods A and E (168 mg) and the title compound was synthesized using the procedure of synthesis method A (step 3) and separation method D. (Yield 24 mg).

$^1$H NMR (CD$_3$OD) δ ppm 7.41-7.54 (m, 1H), 7.25-7.37 (m, 1H), 7.03-7.17 (m, 1H), 4.04 (ddd, 0.2H), 3.76-3.90 (m, 0.8H), 3.44-3.64 (m, 4H), 2.78-2.95 (m, 1H), 2.37-2.62 (m, 1H), 1.74 (s, 0.6H), 1.68 (s, 2.4H), 1.32-1.41 (m, 3H).

Example 32

2-((3R)-5-bromo-3-methylisochroman-1-yl)-4,5-dihydro-1H-imidazole

The title compound was prepared from (R)-1-(2-bromophenyl)propan-2-ol (400 mg) using the procedure of synthesis method A and separation method D (heptane). (Yield 75 mg).

$^1$H NMR (CD$_3$OD) δ ppm 7.49 (d, 1H), 7.24 (d, 1H), 7.02-7.18 (m, 1H), 5.42 (s, 1H), 3.76-3.97 (m, 1H), 3.51-3.72 (m, 5H), 2.75-2.96 (m, 1H), 2.58 (dd, 1H), 1.22-1.51 (m, 3H).

Example 33

2-((3R)-5-chloro-3-methylisochroman-1-yl)-4,5-dihydro-1H-imidazole

The title compound was prepared from (R)-1-(2-chlorophenyl)propan-2-ol (0.3 g) using the procedure of synthesis method A and separation methods A and D (Et$_2$O and heptane). (Yield 0.03 g).

$^1$H NMR (DMSO-d$_6$) δ ppm 7.35-7.37 (d, 1H), 7.17-7.23 (m, 2H), 6.14 (br s, 1H), 5.36 (s, 1H), 3.83-3.91 (m, 1H), 3.6 (br m, 2H), 3.10-3.30 (br s, 2H), 2.82-2.86 (d, 1H), 2.46-2.53 (d, 1H), 1.33-1.34 (d, 3H).

Example 34

2-((3S)-5-chloro-3-methylisochroman-1-yl)-4,5-dihydro-1H-imidazole

The title compound was prepared from (S)-1-(2-chlorophenyl)propan-2-ol (0.3 g) using the procedure of synthesis method A and separation methods A and E (Et$_2$O and heptane). (Yield 0.03 g).

$^1$H NMR (CDCl$_3$) δ ppm 7.34-7.36 (d, 1H), 7.28-7.30 (d, 1H), 7.11-7.15 (tr, 1H), 5.54 (br s, 1H), 3.86-3.94 (m, 1H), 3.56-3.76 (br m, 4H), 2.89-2.94 (dd, 1H), 2.54-2.61 (m, 1H), 1.37-1.43 (m, 3H).

Example 35

2-((3S)-5-bromo-3-methylisochroman-1-yl)-4,5-dihydro-1H-imidazole

The title compound was prepared from (S)-1-(2-bromophenyl)propan-2-ol (200 mg) using the procedure of synthesis method A and separation methods D (Et$_2$O) and G. (Yield 23 mg).

$^1$H NMR (CD$_3$OD) δ ppm 7.38-7.60 (m, 1H), 7.23 (d, 1H), 7.03-7.18 (m, 1H), 5.42 (s, 1H), 4.03-4.13 (m, 0.3H), 3.79-3.98 (m, 0.7H), 3.43-3.71 (m, 4H), 2.81-2.97 (m, 1H), 2.58 (dd, 0.7H), 2.46 (dd, 0.3H), 1.34-1.40 (m, 3H).

Example 36

2-((3R)-3,5-dimethylisochroman-1-yl)-4,5-dihydro-1H-imidazole

The title compound was prepared from (R)-o-tolylpropan-2-ol (400 mg) using the procedure of synthesis method A and separation method E. (Yield 40 mg).

$^1$H NMR (CD$_3$OD) δ ppm 6.99-7.11 (m, 3H), 5.43 (s, 1H), 3.88 (ddd, 1H), 3.53-3.66 (m, 4H), 2.72 (dd, 1H), 2.47-2.61 (m, 1H), 1.39 (d, 3H).

Example 37

2-((3S)-3,5-dimethylisochroman-1-yl)-4,5-dihydro-1H-imidazole

The title compound was prepared from (S)-o-tolylpropan-2-ol (400 mg) using the procedure of synthesis method A and separation methods E and D. (Yield 40 mg).

$^1$H NMR (CD$_3$OD) δ ppm 6.99-7.13 (m, 3H), 5.43 (s, 1H), 3.82-3.93 (m, 1H), 3.53-3.66 (m, 4H), 2.66-2.79 (m, 1H), 2.48-2.62 (m, 1H), 1.39 (d, 3H).

Example 38

2-(5-Methoxy-3-methylisochroman-1-yl)-4,5-dihydro-1H-imidazole

The title compound was prepared from 2-(5-bromo-3-methylisochroman-1 yl)-4,5-dihydro-1H-imidazole (200 mg) using the procedure of synthesis method E and separation methods K and G. (Yield 5.8 mg).

$^1$H NMR (CD$_3$OD) δ ppm 7.07-7.18 (m, 1H), 6.76-6.87 (m, 2H), 5.41 (s, 1H), 3.76-3.87 (m, 4H), 3.55-3.67 (m, 4H), 2.83 (dd, 1H), 2.42 (dd, 1H), 1.31-1.41 (m, 3H).

Example 39

2-(5-Ethyl-3-methylisochroman-1-yl)-4,5-dihydro-1H-imidazole

The title compound was prepared from 2-(5-bromo-3-methylisochroman-1-yl)-4,5-dihydro-1H-imidazole (200 mg) using the procedure of synthesis method D and separation methods J and G. (Yield 18.4 mg).

$^1$H NMR (CD$_3$OD) δ ppm 7.04-7.14 (m, 2.6H), 6.96-7.01 (m, 0.4H), 5.45 (s, 0.7H), 4.11 (s, 0.2H), 3.87 (ddd, 0.8H), 3.51-3.66 (m, 4H), 2.75-2.89 (m, 1H), 2.54-2.70 (m, 3H), 1.37-1.43 (m, 2.3H), 1.33 (d, 0.7H), 1.20 (t, 3H).

Example 40

2-(5-Bromo-3-propylisochroman-1-yl)-4,5-dihydro-1H-imidazole

The title compound was prepared from 1(-2-bromophenyl) pentan-2-ol (only 50% of the prepared ester was used in the last step) using the procedure of synthesis method B (Lewis acid catalyst $BF_3*Et_2O$). (Yield 400 mg).
$^1$H NMR (CD$_3$OD) δ ppm 7.41-7.54 (m, 1H), 7.23 (d, 1H), 7.03-7.14 (m, 1H), 5.39 (s, 1H), 3.74 (td, 1H), 3.50-3.68 (m, 4H), 2.85 (d, 1H), 2.58 (dd, 1H), 1.45-1.75 (m, 4H), 0.92-1.04 (m, 3H).

Example 41

2-(5-Isopropylisochroman-1-yl)-4,5-dihydro-1H-imidazole

To a solution of 2-(5-bromoisochroman-1-yl)-4,5-dihydro-1H-imidazole (0.25 g, synthesis method A), palladium (II) acetate (0.01 g), tri-tert-butylphosphine (0.044 ml) and toluene (3 ml) in ice bath temperature was added 6.22 ml of 0.5M isopropyl zinc bromide in THF, and stirred at ambient temperature for 3 hrs. The reaction was quenched with dilute hydrochloric acid, and the organic phase was separated. The aqueous phase was made alkaline with 1M NaOH, and purified with separation methods A and G to yield the title compound. (Yield 2 mg).
$^1$H NMR (CDCl$_3$) δ ppm 7.20 (br s, 3H), 5.48 (s, 1H), 4.22-4.27 (m, 1H), 3.85-3.91 (m, 1H), 3.63 (br s, 4H), 3.05-3.12 (m, 1H), 2.91-2.99 (m, 1H), 2.75-2.80 (m, 1H), 1.21-1.23 (m, 6H).

Example 42

2-(5-Fluoroisochroman-1-yl)-4,5-dihydro-1H-imidazole

The title compound was prepared from 2-(2-fluorophenyl) ethanol (0.4 g) using the procedure of synthesis method B. The final product was purified by washing the evaporation residue with cold water. (Yield 0.09 g).
$^1$H NMR (DMSO-d$_6$) δ ppm 7.17-7.23 (m, 1H), 7.03-7.08 (m, 2H), 6.31 (br s, 1H), 5.32 (s, 1H), 4.10-4.15 (m, 1H), 3.79-3.85 (m, 1H), 3.43-3.75 (br s, 2H), 3.09-3.30 (br s, 2H), 2.67-2.83 (m, 2H).

Example 43

2-(5-Bromo-3-ethylisochroman-1-yl)-4,5-dihydro-1H-imidazole

The title compound was prepared from 1-(2-bromophenyl) butan-2-ol (600 mg) using the procedure of synthesis method B (boron trifluoride diethyletherate was used instead of titanium(IV)chloride) and separation method D. (Yield 480 mg).
$^1$H NMR (CD$_3$OD) δ ppm 7.40-7.53 (m, 1H), 7.24 (d, 1H), 7.09 (q, 1H), 5.39 (s, 1H), 3.52-3.70 (m, 5H), 2.80-2.92 (m, 1H), 2.58 (dd, 1H), 1.56-1.80 (m, 2H), 0.99-1.10 (m, 3H).

Example 44

2-((3R)-5-methoxy-3-methylisochroman-1-yl)-4,5-dihydro-1H-imidazole

The title compound was prepared from 2-((3R)-5-bromo-3-methylisochroman-1-yl)-4,5-dihydro-1H-imidazole (200 mg) using the procedure of synthesis method E (with 2-di-tert-butylphosphino-3,4,5,6-tetramethyl-2',4',6'-triisopropyl-1,1'-biphenyl) and separation methods J and G. (Yield 31.4 mg).
$^1$H NMR (CD$_3$OD) δ ppm 7.08-7.20 (m, 1H), 6.79-6.85 (m, 1.7H), 6.73-6.75 (d, 0.3H), 5.40 (s, 0.7H), 4.07-4.10 (m, 0.2H), 3.80-3.92 (m, 3.8H), 3.46-3.68 (m, 4H), 2.74-2.90 (m, 1H), 2.28-2.47 (m, 1H), 1.35-1.41 (m, 2.3H), 1.31 (d, 0.7H).

Example 45

2-((3R)-5-ethyl-3-methylisochroman-1-yl)-4,5-dihydro-1H-imidazole

The title compound was prepared from (R)-1-(2-ethylphenyl)propan-2-ol (2.2 g) using the procedure of synthesis method A. The intermediate (3R)-methyl 5-ethyl-3-methylisochroman-1-carboxylate was purified with the separation method E. (Yield 146 mg).
$^1$H NMR (CD$_3$OD) δ ppm 7.01-7.21 (m, 3H), 5.44 (s, 1H), 4.06-4.17 (m, 0.15H), 3.77-3.96 (m, 0.85H), 3.49-3.69 (m, 4H), 2.75-2.91 (m, 1H), 2.54-2.69 (m, 3H), 1.26-1.46 (m, 3H), 1.19 (t, 3H).

Example 45 HCl Salt 2-((3R)-5-ethyl-3-methylisochroman-1-yl)-4,5-dihydro-1H-imidazole hydrochloride The title compound was prepared from compound of example 45 (100 mg) as described in the example 8 (IPA, yield 71 mg).
$^1$H NMR (DMSO-d6) δ ppm 10.63 (br. s., 2H), 7.13-7.38 (m, 2H), 6.94-7.13 (m, 1H), 5.87 (br. s., 1H), 3.88 (br. s., 4H), 3.61-3.74 (m, 1H), 2.66-2.82 (m, 1H), 2.42-2.65 (m, 1H), 2.14-2.32 (m, 3H), 1.60-1.83 (m, 2H), 0.79-1.07 (m, 3H).

Example 45 Hemifumarate Salt 2-((3R)-5-ethyl-3-methylisochroman-1-yl)-4,5-dihydro-1H-imidazole hemifumarate The title compound was prepared from compound of example 45 (940 mg) as described in the example 8 (ethanol, yield 1.16 g).
$^1$H NMR (DMSO-d$_6$) δ ppm 6.97-7.20 (m, 3H), 6.43 (s, 1H), 5.59 (s, 0.7H), 5.49 (s, 0.3H), 4.04-4.08 (m, 0.3H), 3.80-3.92 (m, 0.7H), 3.59 (br. s., 4H), 3.55 (s, 1H), 2.77 (m, 2H), 2.56-2.63 (m, 1H), 1.26-1.37 (m, 3H), 1.15 (t, 3H).

Example 46

2-(3-Ethyl-5-methoxyisochroman-1-yl)-4,5-dihydro-1H-imidazole

The title compound was prepared from 1-(2-bromophenyl) butan-2-ol (1.1 g) using the procedure of synthesis methods B (boron trifluoride diethyletherate was used instead of titanium(IV)chloride) and E (with 2-di-tert-butylphosphino-3,4,5,6-tetramethyl-2',4',6'-triisopropyl-1,1'-biphenyl) (C—O coupling reaction was performed to intermediate ethyl 5-bromo-3-ethylisochroman-1-carboxylate, only 60% of the prepared amount was used in this step). The C—O coupling reaction yielded free acid which was further methylated (synthesis method A) before the final reaction step. The title compound was obtained by concentration of the reaction mixture. (Yield 186 mg).

$^1$H NMR (CD$_3$OD) δ ppm 7.12 (t, 1H), 6.82 (d, 2H), 5.38 (s, 1H), 3.82 (s, 3H), 3.48-3.69 (m, 5H), 2.73-2.90 (m, 1H), 2.41 (dd, 1H), 1.70 (dt, 2H), 0.96-1.10 (m, 3H).

Example 47

2-((3R)-3,5-diethylisochroman-1-yl)-4,5-dihydro-1H-imidazole

Step 1: (R)-1-(2-ethylphenyl)butan-1-ol

The 1-bromo-2-ethylbenzene (2.0 g) was dissolved in dry THF and the mixture was cooled to −78° C. 1.6 M n-BuLi (20.26 ml) was slowly added to the reaction mixture and then the mixture was stirred at −78° C. After 1 h (R)-(+)-1,2-epoxybutane (1.1 g) was added in 10 ml of THF. The reaction mixture was allowed to warm to ambient temperature and then stirred over night. The reaction was quenched with ice-water and product extracted in heptanes, and finally purified by using the separation method E yielding the title compound (1.1 g).

Step 2: 2-((3R)-3,5-diethylisochroman-1-yl)-4,5-dihydro-1H-imidazole

The title compound was prepared from (R)-1-(2-ethylphenyl)butan-1-ol (1.1 g) using the procedure of synthesis method A and separation method D. (Yield 660 mg).

$^1$H NMR (CD$_3$OD) δ ppm 6.99-7.19 (m, 3H), 5.43 (s, 1H), 3.49-3.68 (m, 5H), 2.74-2.86 (m, 1H), 2.55-2.66 (m, 3H), 1.54-1.79 (m, 2H), 1.19 (t, 3H), 0.95-1.11 (m, 3H).

Example 48

2-((3R)-3-ethyl-5-methylisochroman-1-yl)-4,5-dihydro-1H-imidazole

The title compound was prepared from (R)-1-(o-tolyl)butan-2-ol (463 mg) using the procedure of synthesis method B. Boron trifluoride diethyletherate was used instead of titanium (IV)chloride and the intermediate (3R)-ethyl 3-ethyl-5-methylisochroman-1-carboxylate was purified using separation method E. The title compound was isolated using the separation method D with MTBE-Heptane as solvent. (Yield 287 mg).

$^1$H NMR (DMSO-d$_6$) δ ppm 6.95-7.12 (m, 3H), 5.98 (br s, 1H), 5.32 (s, 1H), 3.49-3.81 (m, 3H), 3.20 (br s, 2H), 2.66 (d, 1H), 2.40-2.47 (m, 1H), 2.19 (s, 3H), 1.54-1.76 (m, 2H), 0.99 (t, 3H).

Example 48 HCl Salt 2-((3R)-3-ethyl-5-methylisochroman-1-yl)-4,5-dihydro-1H-imidazole hydrochloride The title compound was prepared from compound of example 48 (100 mg) as described in the example 8 (IPA, yield 72 mg).

$^1$H NMR (DMSO-d$_6$) δ ppm 10.60 (br. s., 2H), 7.15-7.28 (m, 2H), 7.03-7.14 (m, 1H), 5.89 (s, 1H), 3.90 (br. s., 4H), 3.08 (s, 1H), 2.82 (d, 1H), 2.55-2.70 (m, 3H), 1.36 (d, 3H), 1.15 (t, 3H).

Example 48 Sulfate Salt 2-((3R)-3-ethyl-5-methylisochroman-1-yl)-4,5-dihydro-1H-imidazole sulfate The title compound was prepared from compound of example 48 (1.5 g) as described in the example 8 (ethanol, yield 2.0 g).

$^1$H NMR (DMSO-d$_6$) δ ppm 10.32 (s, 2H), 7.16-7.22 (m, 2H), 7.00-7.02 (m, 1H), 5.78 (s, 1H), 3.87-3.93 (m, 5H), 2.74 (dd, 1H), 2.50-2.59 (m, 1H), 1.66-1.74 (m, 2H), 1.10 (t, 3H), 1.01 (t, 3H).

Example 48 Hemifumarate Salt 2-((3R)-3-ethyl-5-methylisochroman-1-yl)-4,5-dihydro-1H-imidazole hemifumarate The title compound was prepared from compound of example 48 (100 mg) as described in the example 8 (ethanol, yield 102.3 mg).

$^1$H NMR (DMSO-d$_6$) δ ppm 7.09-7.19 (m, 2H), 6.99-7.07 (m, 1H), 6.43 (s, 1H), 5.60 (s, 0.7H), 5.50 (s, 0.3H), 4.05-4.08 (m, 0.3H), 3.81-3.92 (m, 0.7H), 3.60 (s, 4H), 2.77 (dd, 1H), 2.56-2.64 (m, 1H), 2.44-2.53 (m, 2H), 1.25-1.37 (m, 3H), 1.15 (t, 3H).

Example 49

2-((3R)-3-methyl-5-(trifluoromethoxy)isochroman-1-yl)-4,5-dihydro-1H-imidazole

Step 1: (R)-1-(2-(trifluoromethoxy)phenyl)propan-2-ol

To a solution of trifluoromethoxybenzene (5.29 mL) and N,N,N',N'-tetramethylethylene-diamine (5.96 mL) in tetrahydrofuran (80 mL) at −78° C. was added sec-butyllithium (32 mL, 1.4 M solution) over 50 minutes. After 2 hours a cooled (−78° C.) solution (R)-(+)-propylene oxide (4.20 mL) in tetrahydrofuran (20 mL) was added over 15 minutes, followed by boron trifluoride diethyl etherate (1.89 mL) over 20 minutes. The reaction mixture was stirred at −78° C. for 2 hours after which aqueous solution of H$_2$SO$_4$ (0.3 M, 50 mL) and water (10 mL) was added. The mixture let to warm up to room temperature after which it was extracted with diethyl ether (2×100 mL). The combined organic phases were washed with brine, dried with Na$_2$SO$_4$ and concentrated. Evaporation residue was purified by separation method E (ethyl acetate-heptane). (Yield 1.40 g).

$^1$H NMR (DMSO-d$_6$) δ ppm 7.24-7.44 (m, 4H), 4.67 (d, 1H), 3.80-3.92 (m, 1H), 2.74 (dd, 1H), 2.65 (dd, 1H), 1.04 (d, 3H).

Step 2: 2-((3R)-3-methyl-5-(trifluoromethoxy)isochroman-1-yl)-4,5-dihydro-1H-imidazole The title compound was prepared from (R)-1-(2-(trifluoromethoxy)phenyl)propan-2-ol (110 mg) using the procedure of synthesis method B. Boron trifluoride diethyletherate was used instead of titanium(IV)chloride. (Yield 36 mg).

¹H NMR (CD₃OD) δ ppm 7.31-7.16 (m, 3H), 5.45 (s, 1H), 4.12-4.02 (m, 0.25H), 4.94-4.83 (m, 0.75H), 3.70-3.54 (m, 4H), 2.95-2.85 (m, 1H), 2.59 (dd, 0.8H), 2.48 (dd, 0.3H), 1.40 (d, 2.4H), 1.34 (d, 0.9H).

Example 50

2-((3R)-5-fluoro-3-methylisochroman-1-yl)-4,5-dihydro-1H-imidazole

The title compound was prepared from (R)-1-(2-fluorophenyl)propan-2-ol (170 mg) using the procedure of synthesis method B. Boron trifluoride diethyletherate was used instead of titanium(IV)chloride. The title compound was purified by trituration of the crude product with heptanes. (Yield 67 mg).
¹H NMR (CD₃OD) δ ppm 7.22-7.14 (m, 1H), 7.05 (d, 1H), 7.01-6.93 (m, 1H), 5.43 (s, 1H), 4.14-4.04 (m, 0.1H), 3.93-3.83 (m, 0.9H), 3.70-3.52 (m, 4H), 2.93-2.83 (m, 1H), 2.56 (dd, 0.9H), 2.46 (dd, 0.1H), 1.40 (d, 2.6H), 1.33 (d, 0.5H).

Example 51

2-(5-Ethoxyisochroman-1-yl)-4,5-dihydro-1H-imidazole

Step 1: 5-Ethoxyisochroman-1-carboxylic acid

The mixture of ethyl 5-bromoisochroman-1-carboxylate (1.0 g, synthesis methods A1 and A2), cesium carbonate (4.57 g), 3,4,7,8-tetramethyl-1,10-phenanthroline (332 mg), copper (I) iodide (134 mg) and ethanol (10 ml) was heated in microwave reactor at 160° C. Methanol was evaporated and the title compound was isolated and purified with separation method B. (Yield 400 mg).

Step 2: 2-(5-Ethoxyisochroman-1-yl)-4,5-dihydro-1H-imidazole

The title compound was prepared from using the procedure of synthesis methods A2 and A3 and purified with separation method D (heptane). (Yield 150 mg).
¹H NMR (CD₃OD) δ ppm 7.11 (t, 1H), 6.80 (t, 2H), 4.11-4.26 (m, 1H), 4.05 (qd, 2H), 3.79 (td, 1H), 3.51-3.66 (m, 4H), 2.62-2.91 (m, 2H), 1.40 (t, 3H).

Example 52

2-(5-Methyl-3-(2,2,2-trifluoroethyl)isochroman-1-yl)-4,5-dihydro-1H-imidazole

Step 1: 4,4,4-Trifluoro-1-(o-tolyl)butan-2-ol

To a mixture of 2,2,2-trifluoroethylamine hydrochloride (0.271 g) in dichloromethane/water (15/0.5 mL) at 0° C. was added sodium nitrite (0.166 g) and the resulting yellow solution was stirred for 1 hour at 0° C. The reaction mixture was then cooled to −78° C. and 2-o-tolylacetaldehyde (0.134 g) was added, followed by zirconium(IV)tetrachloride. After stirring for 2 hrs at −78° C. cooling was stopped and methanol (3 mL) and saturated solution of NaHCO₃ (10 mL) were added. The mixture was extracted with dichloromethane and the extracts were dried and concentrated. Evaporation residue (194 mg) was dissolved in methanol (3 ml) and solution was cooled to 0° C. Sodium borohydride (44 mg) was added and the reaction mixture was stirred for 25 minutes. K₂CO₃-solution (2M, 5 mL) was added to the reaction mixture, followed by water (5 mL) after 5 min and the resulting solution was extracted with EtOAc. Extracts were dried and concentrated and the residue was purified by separation method E (EtOAc/heptane). (Yield 121 mg).
¹H NMR (CDCl₃) δ ppm 7.23-7.12 (m, 4H), 4.26-4.17 (m, 1H), 2.90 (dd, 1H), 2.80 (dd, 1H), 2.45-2.27 (m, 2H), 2.34 (s, 3H), 1.86 (d, 1H).

Step 2: 2-(5-Methyl-3-(2,2,2-trifluoroethyl)isochroman-1-yl)-4,5-dihydro-1H-imidazole The title compound was prepared from 4,4,4-trifluoro-1-(o-tolyl)butan-2-ol (121 mg) using the procedure of synthesis method B. Boron trifluoride diethyletherate was used instead of titanium(IV)chloride. The title compound was purified by separation method E (dichloromethane-MeOH—NH₄OH). (Yield 11 mg).
¹H NMR (CD₃OD) δ ppm 7.13-7.04 (m, 2.6H), 6.99-6.93 (m, 0.3H), 5.47 (s, 1H), 4.41-4.33 (m, 0.3H), 4.15-4.07 (m, 0.7H), 3.63-3.51 (m, 4H), 2.87-2.46 (m, 4H), 2.25 (s, 3H).

Example 53

2-((3S)-5-methoxy-3-methylisochroman-1-yl)-4,5-dihydro-1H-imidazole

The title compound was prepared from 2-((3S)-5-bromo-3-methylisochroman-1-yl)-4,5-dihydro-1H-imidazole (200 mg) using the procedure of synthesis method E (with 2-di-tert-butylphosphino-3,4,5,6-tetramethyl-2',4',6'-triisopropyl-1,1'-phenyl) and separation method G. (Yield 16.3 mg).
¹H NMR (CD₃OD) δ ppm 7.10-7.24 (m, 1H), 6.82-6.90 (m, 1.6H), 6.78 (d, 0.4H), 5.44 (s, 0.7H), 4.05-4.15 (m, 0.3H), 3.80-3.93 (m, 3.7H), 3.53-3.70 (m, 4H), 2.80-2.92 (m, 1H), 2.31-2.50 (m, 1H), 1.41 (d, 2.1H), 1.34 (d, 0.9H).

Example 54

2-(5-(Furan-3-yl)isochroman-1-yl)-4,5-dihydro-1H-imidazole

To a mixture of 2-(2-bromoisochroman-1-yl)-4,5-dihydro-1H-imidazole (100 mg), bis(tri-t-butylphosphine)palladium (9 mg), furan-3-boronic acid (80 mg) and cesium carbonate (202 mg) was added ethylene glycol dimethyl ether (4 ml), ethanol (2 ml) and water (1 ml). The reaction mixture was degassed with N₂ and heated in a microwave oven for 30 min at 100° C. The title compound was purified by applying methods J and G. (Yield 19 mg).
¹H NMR (CD₃OD) δ ppm 7.60-7.67 (m, 1H), 7.52-7.60 (m, 1H), 7.10-7.33 (m, 3H), 6.49-6.70 (m, 1H), 4.18 (ddd, 1H), 3.71-3.84 (m, 1H), 3.55-3.67 (m, 4H), 2.97-3.19 (m, 1H), 2.64-2.81 (m, 1H).

Example 55

2-(5-(Prop-1-yn-1-yl)isochroman-1-yl)-4,5-dihydro-1H-imidazole

The title compound was prepared from 2-(2-bromoisochroman-1-yl)-4,5-dihydro-1H-imidazole (100 mg) using the procedure of synthesis method C and separation methods F and G. (Yield 3.7 mg).
¹H NMR (CD₃OD) δ ppm 7.27 (dd, 1H), 7.12 (m, 2H), 5.34 (s, 0.2H), 4.22 (ddd, 1H), 3.83 (ddd, 1H), 3.59 (m, 4H), 2.94 (m, 2H), 2.07 (s, 3H).

Example 56

1-(4,5-Dihydro-1H-imidazol-2-yl)isochroman-5-carboxamide

The mixture of 1-(4,5-dihydro-1H-imidazol-2-yl)isochroman-5-carbonitrile (example 5, 75 mg), acetamide (39 mg), zink chloride (45 mg), THF (0.5 ml) and water (0.5 ml) was heated in a microwave reactor for 50 seconds at 320 W. The title compound was purified by applying method A. (Yield 15 mg).
$^1$H NMR (CDCl$_3$) δ ppm 8.06 (d, 1H), 7.57 (d, 1H), 7.32 (t, 1H), 5.17 (s, 1H), 4.16-4.41 (m, 1H), 3.75-4.03 (m, 1H), 2.93-3.44 (m, 4H), 2.77-2.93 (m, 2H).

Example 57

2-(3,7,8,9,10,10a-Hexahydro-1H-cyclohepta[de]isochromen-3-yl)-4,5-dihydro-1H-imidazole The title compound was prepared from (6,7,8,9-tetrahydro-5H-benzo[7]annulen-5-yl)methanol (300 mg) using the procedure of synthesis method A and separation methods F and G. (Yield 3 mg).
$^1$H NMR (CDCl$_3$) δ ppm 6.96-7.24 (m, 3H), 5.32-5.48 (m, 1H), 3.74-4.03 (m, 3H), 3.39-3.60 (m, 4H), 2.65-2.98 (m, 2H), 1.84-2.11 (m, 2H), 1.52-1.82 (m, 2H), 1.19-1.42 (m, 2H).

Example 58

1-(1-(4,5-Dihydro-1H-imidazol-2-yl)isochroman-5-yl)ethanol, slow eluting isomer

The title compound was prepared from 2-(2-bromoisochroman-1-yl)-4,5-dihydro-1H-imidazole (300 mg) using the procedure of Example 13 and purified by applying separation method G. (Yield 2 mg).
$^1$H NMR (CD$_3$OD) δ ppm 7.48 (d, 1H), 7.26 (m, 2H), 5.06 (q, 1H), 3.99 (m, 2H), 3.74 (s, 4H), 2.96 (dt, 1H), 2.84 (dt, 1H), 1.78 (d, 3H).

Example 59

2-(5,7-Dimethylisochroman-1-yl)-4,5-dihydro-1H-imidazole

The title compound was prepared from 2-(2,4-dimethylphenyl)ethanol (0.5 g) using the procedure of synthesis method A. The intermediate 5,7-dimethylisochroman-1-carboxylic acid was isolated using the separation method I and the intermediate methyl 5,7-dimethylisochroman-1-carboxylate was purified by separation method E. The title compound was isolated using separation method G. (Yield 27 mg).
$^1$H NMR (CD$_3$OD) δ ppm 8.45 (br. s., 1H), 7.04 (s, 1H), 6.85 (s, 1H), 5.68 (s, 1H), 4.11-4.19 (m, 1H), 3.87-4.02 (m, 5H), 2.76-2.88 (m, 1H), 2.64-2.76 (m, 1H), 2.20-2.35 (m, 6H).

Example 60

2-(7-Bromo-5-methylisochroman-1-yl)-4,5-dihydro-1H-imidazole

The title compound was prepared from 2-(4-bromo-2-methylphenyl)ethanol (4.5 g) using the procedure of synthesis method A (4-methylbenzenesulfonic in methanol was used in the step A2), and isolated using separation method D with MTBE-heptane as solvent. (Yield 242 mg).
$^1$H NMR (DMSO-d$_6$) δ ppm 7.29 (s, 1H), 7.20 (s, 1H), 6.32 (br. s., 1H), 5.28 (s, 1H), 4.09 (dt, 1H), 3.82 (ddd, 1H), 3.63 (dt, 2H), 3.18-3.27 (m, 2H), 2.57-2.72 (m, 2H), 2.20 (s, 3H).

Example 61

2-(7-Methoxy-5-methylisochroman-1-yl)-4,5-dihydro-1H-imidazole

The title compound was prepared from methyl 7-methoxy-5-methylisochroman-1-carboxylate (0.25 g) using the procedure of synthesis method A3 and isolated using separation method G. (Yield 113 mg).
$^1$H NMR (DMSO-d$_6$) δ ppm 6.65-6.75 (m, 1H), 6.54-6.65 (m, 1H), 6.18 (br. s., 1H), 5.23 (s, 1H), 3.98-4.25 (m, 1H), 3.71-3.86 (m, 1H), 3.66 (s, 3H), 3.20-3.30 (m, 4H, H$_2$O), 2.52-2.72 (m, 2H), 2.17 (s, 3H).

Example 62

2-(3,5-Dimethylisothiochroman-1-yl)-4,5-dihydro-1H-imidazole

The title compound was prepared from methyl 3,5-dimethylisothiochroman-1-carboxylate (0.44 g) using the procedure of synthesis method A3 and isolated using separation method G. (Yield 10 mg).
$^1$H NMR (CD$_3$OD) δ ppm 6.93-7.23 (m, 3H), 3.38-3.68 (m, 5H), 2.98-3.19 (m, 1H), 2.48 (dd, 1H), 2.19-2.37 (m, 3H).

Example 63

2-(5-Bromo-3-methylisothiochroman-1-yl)-4,5-dihydro-1H-imidazole

The title compound was prepared from methyl 5-bromo-3-methylisothiochroman-1-carboxylate (0.5 g, synthesis methods A1 and A2) using the procedure of synthesis method A3 and isolated using separation method E. (Yield 72 mg).
$^1$H NMR (CD$_3$OD) δ ppm 7.53 (d, 1H), 7.03-7.25 (m, 2H), 3.47-3.69 (m, 5H), 3.37-3.46 (m, 1H), 2.57 (dd, 1H), 1.17-1.46 (m, 3H).

Example 64

2-(5-Methylisothiochroman-1-yl)-4,5-dihydro-1H-imidazole

The title compound was prepared from methyl 5-methylisothiochroman-1-carboxylate (1.3 g, synthesis method F) using the procedure of synthesis method A3 and isolated using separation method D with EtOAc/EtOH as solvents. (Yield 110 mg).
$^1$H NMR (CDCl$_3$) δ ppm 6.90-7.17 (m, 3H), 4.63 (s, 1H), 3.52-3.75 (m, 4H), 3.08-3.25 (m, 1H), 2.80-3.02 (m, 3H).

Example 65

2-(5-Bromoisothiochroman-1-yl)-4,5-dihydro-1H-imidazole

Synthesis Method F
Synthesis Method F1: Methyl-2-((2-bromophenethyl)thio)acetate
A mixture of methyl 2-mercaptoacetate (2.2 g), 2-bromophenethyl methanesulfonate (5.7 g), 2,3,4,6,7,8,9,10-octahydropyrimido[1,2-a]azepine (3.7 g) and THF (30 ml) was stirred at ambient temperature for 1.5 hrs and separation method A and E yielded the title compound (4.4 g).

Synthesis Method F2: Methyl-2-((2-bromophenethyl)thio)-2-chloroacetate

A mixture of methyl 2-((2-bromophenethyl)thio)acetate (4.4 g), 1-chloropyrrolidine-2,5-dione (2 g) and carbon tetrachloride (2.4 g) was stirred on ice-bath for 2.5 hrs, filtrated and evaporated to yield the title compound (4.7 g).

Synthesis Method F3: Methyl-5-bromoisothiochroman-1-carboxylate

A mixture of methyl 2-((2-bromophenethyl)thio)-2-chloroacetate (4.7 g), aluminum trichloride (2 g) and DCM (15 ml) was stirred in ice bath and allowed to warm up to ambient temperature and stirred 3.5 hrs. Separation method B and E yielded the title compound (2.9 g).

Synthesis Method F4: 2-(5-Bromoisothiochroman-1-yl)-4,5-dihydro-1H-imidazole

The title compound was prepared from methyl-5-bromo-isothiochroman-1-carboxylate (0.5 g) using the procedure of synthesis method A3 and isolated using separation methods E and D (2-propanol, Yield 21 mg).

$^1$H NMR (DMSO-$d_6$) δ ppm 7.52 (dd, 1H), 7.02-7.19 (m, 2H), 4.65 (s, 1H), 3.77 (td, 1H), 3.17-3.60 (br. s., 4H), 2.96-3.09 (m, 1H), 2.75-2.95 (m, 2H).

Example 66

2-(5-Bromo-1-methylisothiochroman-1-yl)-4,5-dihydro-1H-imidazole

The title compound was prepared from methyl-5-bromoisothiochroman-1-carboxylate (1.6 g) using the procedures of the synthesis method of example 11 and A3 and isolated with the separation method E. (Yield 30 mg).

$^1$H NMR (CDCl$_3$) δ ppm 7.46-7.56 (m, 1H), 7.21-7.39 (m, 1H, CHCl$_3$), 7.02-7.16 (m, 1H), 3.17-4.0 (m, 4H), 2.70-3.10 (m, 3H), 1.48-2.01 (m, 4H).

Example 67

2-(5,7-Dibromo-3-ethylisochroman-1-yl)-4,5-dihydro-1H-imidazole, hydrochloride

Step 1: Ethyl 5,7-dibromo-3-ethylisochroman-1-carboxylate

A dry microwave vial was charged with di-μ-methoxobis(1,5-cyclooctadiene)diiridium (I) (5.0 mg), 4,4'-dimethoxy-2,2'-dipyridyl (3.2 mg), bis(pinacolato)diboron (93 mg) and 2-(5-bromo-3-ethylisochroman-1-yl)-4,5-dihydro-1H-imidazole (157 mg, example 43) and the vial was flushed using vacuum/N$_2$ cycle for several times. Tetrahydrofuran (1 mL) was added and solution was heated to 80° C. in a sealed vessel. After 4 hours heating was stopped and the reaction mixture was concentrated. Evaporation residue was dissolved in methanol (6 mL) and solution of CuBr$_2$ in water (6 mL) wad added. The resulting heterogeneous mixture was heated to 80° C. in sealed vessel. After 8 hours the reaction mixture was cooled to room temperature and extracted with diethyl ether. Combined organic phases were washed with brine, dried with Na$_2$SO$_4$ and concentrated. Evaporation residue was purified by separation method E (ethyl acetate-heptane). (Yield 94 mg).

$^1$H NMR (CDCl$_3$) δ ppm 7.63-7.67 (m, 1H), 7.55-7.58 (m, 0.33H), 7.38-7.44 (m, 0.63H), 5.31-5.36 (m, 0.11H) 5.28-5.31 (d, 0.89H), 4.19-4.38 (m, 2H), 4.00-4.09 (m, 0.37H), 3.50-3.60 (m, 0.63H), 2.72-2.83 (m, 1H), 2.56 (ddd, 0.64H), 2.39 (dd, 0.36H), 1.66-1.90 (m, 2H), 1.30-1.36 (m, 3H), 1.02-1.13 (m, 3H).

Step 2: 2-(5,7-Dibromo-3-ethylisochroman-1-yl)-4,5-dihydro-1H-imidazole, hydrochloride Title compound was synthesized using synthesis method A3 and converted to HCl-salt using salt formation method A. (Yield 60 mg).

$^1$H NMR (DMSO-$d_6$) δ ppm 10.59 (s, 1.57H), 10.08 (s, 0.36H), 7.93-7.96 (m, 1H), 7.59 (d, 0.19H), 7.48-7.51 (m, 0.77H), 5.92 (br s, 0.19H), 5.90 (br s, 0.78H), 3.84-4.00 (m, 4H), 3.63-3.78 (m, 1H), 2.74-2.84 (m, 1H), 2.50-2.57 (m, 1H), 1.61-1.77 (m, 2H), 0.94-1.02 (m, 3H).

Example 68

Enantiomer of 2-5-bromo-3-(2,2,2-trifluoroethyl)isochroman-1-yl)-4,5-dihydro-1H-imidazole, HCl salt Step 1: 1-(2-Bromophenyl)-4,4,4-trifluorobutan-2-one To a solution of 2,2,2-trifluoroethanamine hydrochloride (27.1 g, 200 mmol) in DCM (400 ml) and water (50 ml) was added NaNO$_2$ (15.43 g, 241 mmol) at 0° C. and stirred for 1 h. Then cooled to 78° C. then added 2-(2-bromophenyl)acetaldehyde (20 g, 100 mmol) and ZrCl$_4$ (30.4 g, 130 mmol) and stirred for 2 h. The reaction mixture was quenched with MeOH (30 ml). The title compound was purified by separation methods A and E. (Yield 13.0 g).

Step 2: Enantiomer of (1-(2-bromophenyl)-4,4,4-trifluorobutan-2-ol

To a solution of 1-(2-bromophenyl)-4,4,4-trifluorobutan-2-one (7.0 g, 24.9 mmol) in MeOH (150 ml) was added NaBH$_4$ (1.23 g, 32.3 mmol) at 0° C. and stirred for 1 h at RT. Then the reaction mixture was quenched with MeOH and concentrated under reduced pressure to afford crude compound. The title compound was purified by separation methods A, E and H. (Yield 1.6 g of Enantiomer-1 and 1.4 g-Enantiomer-2). The enantiomer-1 showed up at $t_r$=5.67 min and enantiomer-2 showed up at $t_r$=9.57 min with Chiralcel OD-H (4.6×250 mm) 5μ, hexane:2-PrOH:TFA (90:10:0.1), 1 ml/min.

Step 3: Enantiomer of 2-5-Bromo-3-(2,2,2-trifluoroethyl)isochroman-1-yl)-4,5-dihydro-1H-imidazole, HCl salt The title compound was prepared from enantiomer-1 of ethyl 1-(2-bromophenyl)-4,4,4-trifluorobutan-2-ol (500 mg) by the synthesis method B and isolated with the separation method E. The obtained base was converted to HCl salt using salt formation method A (HCl in Et$_2$O and DCM as solvent) (Yield 192 mg).

$^1$H NMR (DMSO-$d_6$) δ ppm 10.73 (br. s., 1.95H), 10.26 (br. s., 2.05H), 7.70 (overlapping dd, 2H), 7.20-7.42 (overlapping m, 4H), 5.99 (br. s, 1.02H), 5.98 (br. s, 0.98H), 4.16-4.33 (overlapping m, 2H), 3.81-3.96 (m, 8H), 2.59-3.09 (m, 8H).

Example 69

2-(5-Methoxy-1-methylisochroman-1-yl)-4,5-dihydro-1H-imidazole

The solution of ethyl glyoxate (50% toluene sol, 11.66 ml) and 2-methoxybenzeneethano (12.73 ml) were stirred for 1 hr to yield ethyl 2-hydroxy-2-(2-methoxyphenethoxy)acetate. The formation of ethyl 2-hydroxy-2-(2-methoxyphenethoxy)acetate was detected by $^1$H NMR and the reaction mixture was cooled with ice-bath and treated with pyridine (48.4 ml), 4-dimethylaminopyridine (0.44 g), and acetyl chloride (12.85 ml). After stirring under +7° C. for 1 hr, heptane (50 ml) was added, and the ice-bath cooling was removed to let the reaction mixture reach ambient temperature followed by filtration. The filtare was washed with MTBE (3×50 ml), and the combined solvents were washed with NaHCO$_3$ (sat aq sol), water and NaCl (sat aq sol), dried over Na$_2$SO$_4$, and filtered. Organics were evaporated, toluene added and evaporated. By-products and residual solvents were distilled of (0 mbar-1 mbar/72°-105° C.), and the residual was dissolved in ethyl acetate. Silica gel and active carbon were added, the solution stirred for 10 min, and filtered. Organics were evaporated to yield ethyl 2-acetoxy-2-(2-methoxyphenethoxy)acetate (12.3 g) which was used in the next step.

The solution of ethyl 2-acetoxy-2-(2-methoxyphenethoxy) acetate (12.3 g) in dichloromethane (415 ml) at −20° C. was treated with AlCl$_3$ (5.5 g), and stirred for 1 hr. AlCl$_3$ (5.5 g) was added to the solution and stirred for 3.5 hrs, pours into ice-water (400 ml). Separation method A was applied, followed by distillation (1-2 mbar/120-130° C.) of the crude product to yield ethyl 5-methoxyisochroman-1-carboxylate (5.1 g).

The mixture of NaH (0.68 g), ethyl 5-methoxyisochroman-1-carboxylate (1 g) and DMF (10 ml) was stirred for 2 hrs in ice-bath temperature. Iodomethane (2.6 ml) was added and the mixture was stirred at ambient temperature for 16 hrs. The intermediate ethyl 5-methoxy-1-methylisochroman-1-carboxylate (0.7 g) was purified with separation method A and the title compound was synthesized using the procedure of synthesis method A step 3 and separation method D (diethyl ether). (Yield 0.1 g).

$^1$H NMR (DMSO-d$_6$) δ ppm 7.10 (tr, 1H), 6.83 (dd, 2H), 6.08 (s, 1H), 3.85 (m, 2H), 3.77 (s, 3H), 3.44-3.70 (br m, 2H), 3.07-3.28 (br s, 2H), 2.62 (tr, 2H), 1.60 (s, 3H).

Example 70

2-(5-Methoxyisothiochroman-1-yl)-4,5-dihydro-1H-imidazole

The title compound was prepared from 2-methoxyphenethyl methanesulfonate (3.58 g) using the procedure of synthesis method F. The title compound was purified by using the separation method E. (Yield 60 mg).

$^1$H NMR (CD$_3$OD) ppm 7.11 (t, 1H), 6.84 (d, 1H), 6.73 (d, 1H), 3.82 (s, 3H), 3.46-3.66 (m, 4H), 3.03-3.17 (m, 2H), 2.75-2.87 (m, 2H).

Example 71

2-((3R)-5-methoxy-1,3-dimethylisochroman-1-yl)-4,5-dihydro-1H-imidazole

The mixture of NaH (0.17 g), (3R)-ethyl 5-methoxy-3-methylisochroman-1-carboxylate (0.3 g) and DMF (7 ml) was stirred for 2 hrs in ice-bath temperature. Iodomethane (0.7 ml) was added and the mixture was stirred at ambient temperature for 16 hrs. The intermediate (3R)-ethyl 5-methoxy-1,3-dimethylisochroman-1-carboxylate (0.4 g) was purified with separation method A and the title compound was synthesized using the procedure of synthesis method A step 3 and separation method E (EtOAc/DCM/triethyl amine 10/20/1). (Yield 0.3 g).

$^1$H NMR (CDCl$_3$) δ ppm 7.01-7.24 (m, 2H), 6.71-6.76 (m, 1H), 3.97-4.24 (m, 1H), 3.80-3.84 (m, 3H), 3.37-3.77 (br, 3H), 2.77-2.90 (m, 1H), 2.32-2.42 (m, 1H), 1.77 (d, 3H), 1.35-1.41 (m, 3H), 1.24-1.29 (m, 1H).

Example 72

2-(5-(2,2,2-Trifluoroethyl)isochroman-1-yl)-4,5-dihydro-1H-imidazole

Step 1: 2-(2-(2,2,2-Trifluoroethyl)phenyl)oxirane

Bromo-2-(2,2,2-trifluoroethyl)benzene (0.5 g) was dissolved in degassed toluene and tributyl(vinyl)tin (0.67 mL), Pd$_2$(dba)$_3$ (0.096 g) and tri-tert-butylphosphine (0.25 mL, 1M solution) were added. Reaction mixture was heated to 40° C. After 4 hours heating was stopped and 1:1 solution of diethyl ether and pentane (10 ml) was added, followed by potassium fluoride (1.0 g). Mixture was stirred for 30 minutes after which it was filtered through a pad of silicagel and the filtrate was concentrated gently at 500 mbar vacuum. The evaporation residue was purified by column chromatography (diethyl ether-pentane) and fractions containing the product were concentrated by house vacuum distillation. The evaporation residue (0.389 g) containing toluene and the desired styrene product was dissolved in dichloromethane (12 mL) and 3-chloroperoxybenzoic acid (0.70 g) was added.

After stirring the reaction mixture overnight at room temperature it was diluted with dichloromethane (20 mL) and solution of Na$_2$SO$_3$ (10 mL, 1M) was added. The biphasic mixture was stirred for 30 minutes and phases were separated. The aqueous phase was extracted with dichloromethane (3×10 mL). All organic phases were combined, washed with saturated NaHCO$_3$-solution, dried with Na$_2$SO$_4$ and concentrated (300 mbar pressure). Evaporation residue was purified by separation method E (diethyl ether-pentane). (Yield 220 mg).

$^1$H NMR (CDCl$_3$) δ ppm 7.26-7.38 (m, 4H), 4.01-4.07 (m, 1H), 3.42-3.69 (m, 2H), 3.17 (dd, 1H), 2.69 (dd, 1H).

Step 2: 2-(2-(2,2,2-Trifluoroethyl)phenyl)ethanol

Flask was charged with Pd(0) EnCat 30 NP (0.136 g, washed with ethanol and ethyl acetate prior to use) and solution of 2-(2-(2,2,2-trifluoroethyl)phenyl)oxirane (0.110 g) in ethyl acetate (1.5 mL) was added followed by triethylamine (0.33 mL) and formic acid (90 μL). Mixture was stirred at room temperature for 26 hours after which it was filtered. Precipitate was washed with ethyl acetate and filtrate was concentrated. Evaporation residue was purified by separation method E (ethyl acetate-heptane). (Yield 70 mg).

$^1$H NMR (CDCl$_3$) δ ppm 7.19-7.34 (m, 4H), 3.87 (td, 2H), 3.50 (q, 2H), 2.96 (t, 2H).

Step 3: 2-(5-(2,2,2-Trifluoroethyl)isochroman-1-yl)-4,5-dihydro-1H-imidazole Title compound was synthesized from 2-(2-(2,2,2-trifluoroethyl)phenyl)ethanol (70 mg) using the procedure of synthesis method B. Boron trifluoride diethyletherate was used instead of titanium(IV)chloride. (Yield 53 mg).

$^1$H NMR (CD$_3$OD) δ ppm 7.16-7.28 (m, 3H), 5.40 (s, 0.1H, exchangeable proton), 4.23 (ddd, 1H), 3.84 (ddd, 1H), 3.46-3.66 (m, 5H), 3.46-3.53 (m, 1H), 2.99 (ddd, 1H), 2.80 (dt, 1H).

Example 73

2-((3R)-5-ethyl-1,3-dimethylisochroman-1-yl)-4,5-dihydro-1H-imidazole

Synthesis Method G

The mixture of NaH (0.39 g), (3R)-ethyl 5-ethyl-3-methylisochroman-1-carboxylate (0.6 g) and DMF (7 ml) was stirred for 2 hrs in ice-bath temperature. Iodomethane (1.5 ml) was added and the mixture was stirred at ambient temperature for 16 hrs. The intermediate (3R)-ethyl 5-ethyl-1,3-dimethylisochroman-1-carboxylate (0.5 g) was purified with separation method A and the title compound was synthesized using the procedure of synthesis method A step 3 and separation method E (EtOAc/DCM/triethyl amine 10/20/1). (Yield 0.06 g).

$^1$H NMR (CDCl$_3$) δ ppm 7.30-7.07 (m, 3H), 4.89 (br, 1H), 3.81-4.10 (M, 1H), 2.47-2.77 (m, 4H), 1.73-1.83 (d, 3H), 1.38 (tr, 3H), 1.21 (td 3H).

Example 74

2-(5-Methyl-3-(methoxymethyl)isochroman-1-yl)-4,5-dihydro-1H-imidazole

The title compound was prepared from ethyl 3-(methoxymethyl)-5-methylisochroman-1-carboxylate (200 mg) by the synthesis method A and isolated with the separation method D. (Yield 134 mg).

$^1$H NMR (CD3OD) δ ppm 7.00-7.14 (m, 3H), 5.45 (s, 1H), 3.96 (dd, 1H), 3.50-3.67 (m, 6H), 3.40-3.46 (m, 3H), 2.63-2.74 (m, 2H), 2.24 (s, 3H).

Example 75

1-(4,5-Dihydro-1H-imidazol-2-yl)-5-methylisochroman-7-ol, hydrobromide 2-(7-Methoxy-5-methylisochroman-1-yl)-4,5-dihydro-1H-imidazole (example 61, 100 mg) was dissolved in hydrobromic acid (1.5 mL, 47 w-% in water) and mixture was heated to reflux. After 5.5 hours mixture was cooled down to room temperature. Solvents were evaporated and the evaporation residue was triturated with ethanol to afford the title compound. (Yield 27 mg).

$^1$H NMR (D$_2$O) δ ppm 6.84 (d, 1H), 6.57 (d, 1H), 5.76 (s, 1H), 4.06 (t, 2H), 4.00 (s, 4H), 2.74 (t, 2H), 2.23 (s, 3H).

Example 76

1-(4,5-Dihydro-1H-imidazol-2-yl)-3-ethylisochroman-5-ol, hydrochloride

Step 1: Methyl 3-ethyl-5-hydroxyisochroman-1-carboxylate

To a mixture of ethyl 5-bromo-3-ethylisochroman-1-carboxylate (500 mg) and KOH (358 mg) was added dioxane (4.5 ml) and water (1.5 ml). 2-Di-tert-butyl-butylphosphino-3,4,5,6-tetramethyl-2',4',6'.triisopropyl-1',1'-biphenyl (38 mg), tris(dibenzylideneacetone)dipalladium(0) and Pd2(dba)3 (73 mg) was added, and then the mixture was heated for 2.5 h at 100° C. After the reaction the reaction mixture was evaporated to dryness and the used directly in the next step.

Reaction crude was dissolved in MeOH (15 ml). Chlorotrimethylsilane (5.9 ml) was added, and the reaction mixture was stirred overnight at rt. The mixture was evaporated to dryness. The title compound was purified by separation method E. (Yield 90 mg).

Step 2: 1-(4,5-Dihydro-1H-imidazol-2-yl)-3-ethyl-isochroman-5-ol, hydrochloride

Methyl 3-ethyl-5-hydroxyisochroman-1-carboxylate (90 mg) was dissolved dichloromethane (1 mL) and 3,4-dihydro-2H-pyran (52 μL) and pyridinium p-toluenesulfonate (9.6 mg) were added. After 28 hours more 3,4-dihydro-2H-pyran (102 μL) and pyridinium p-toluenesulfonate (10 mg) were added and mixture was stirred for another 24 hours. 3,4-Dihydro-2H-pyran (200 μL) was then added and mixture was stirred overnight after which it was diluted with diethyl ether (5 ml) and washed with saturated NaHCO$_3$-solution. Organic phase was dried with Na$_2$SO$_4$ and concentrated. Purification of the evaporation residue by column chromatography (ethyl acetate-heptane) afforded 37 mg of oil that was converted to 2-(3-ethyl-5-((tetrahydro-2H-pyran-2-yl)oxy)isochroman-1-yl)-4,5-dihydro-1H-imidazole (13 mg) using the synthesis method A3. The crude product of this procedure was dissolved in methanol (1 ml) and HCl solution in diethyl ether (2M, 39 μL) was added. After 2.5 hours reaction mixture was concentrated and the residue was taken in water (10 mL). The solution was washed with ethyl acetate and the water layer was concentrated in freeze dryer to afford the title compound. (Yield 6 mg).

$^1$H NMR (DMSO-d$_6$) δ ppm 10.43 (s, 1.3H), 9.92 (s, 0.45H) 9.80 (s, 0.9H), 7.03-7.14 (m, 1H), 6.78-6.88 (m, 1H), 6.58-6.70 (m, 1H), 5.78 (s, 0.11H), 5.75 (s, 0.61H), 3.84-3.93 (m, 4H), 3.61-3.74 (m, 1H), 2.77 (d, 1H), 2.28-2.44 (m, 1H), 1.53-1.76 (m, 2H), 0.92-1.03 (m, 3H).

Example 77

Enantiomer-2 of 2-(5-methoxy-3-(2,2,2-trifluoroethyl)methyl-isochroman-1-yl)-4,5-dihydro-1H-imidazole Step 1: (R)-4,4,4-trifluoro-1-(2-methoxyphenyl)butan-2-ol To a solution of 4,4,4-trifluoro-1-(2-methoxyphenyl)butan-2-one (6 g, 25.8 mmol, synthesized as in example 52, step 1) in MeOH (100 ml) was added NaBH$_4$ (1.47 g, 38.7 mmol) at 0° C. and stirred for 1 h at RT. Then the reaction mixture was quenched with MeOH and concentrated under reduced pressure to afford crude compound. The title compound was purified by separation methods A, E and H. Yield (1.7 g). The enantiomer showed up at t$_r$=12.8 min with Chiralpak 1A (4.6×250 mm) 5μ, hexane:2-PrOH:TFA (90:10:0.1), 1 ml/min.

Step 2: Enantiomer-2 of 2-(5-methoxy-3-(2,2,2-trifluoroethyl)methylisochroman-1-yl)-4,5-dihydro-1H-imidazole The title compound was prepared from enantiomer-2 of 4,4,4-trifluoro-1-(2-methoxyphenyl)butan-2-ol (900 mg) by the synthesis method G and isolated with the separation method E. (Yield 30 mg).

¹H NMR (CD₃OD) δ ppm 7.14-7.26 (m, 2H), 6.85 (t, 1H), 5.46 (s, 1H), 4.06 (dd, 1H), 3.81-3.88 (m, 3H), 3.48-3.69 (m, 4H), 2.93 (dd, 1H), 2.45-2.70 (m, 2H).

Example 78

2-(1,5-Dimethylisothiochroman-1-yl)-4,5-dihydro-1H-imidazole

The title compound was synthesized using ethyl 1,5-dimethylisothiochroman-1-carboxylate and the procedure of synthesis method A step 3 and separation methods D (diethyl ether), E (EtOAc/DCM/triethyl amine 10/18/1) and D (diethyl ether/heptanes), respectively. (Yield 0.06 g).
¹H NMR (DMSO-d₆) δ ppm 7.04 (m, 3H), 5.91 (s, 1H), 3.45-3.70 (br, 2H), 3.18-3.30 (br, 2H), 3.03-3.12 (m, 1H), 2.92-2.81 (m, 3H), 2.20 (s, 3H), 1.77 (s, 3H).

Example 79

2-(5-(Trifluoromethoxy)isochroman-1-yl)-4,5-dihydro-1H-imidazole, HCl salt

The title compound was prepared from 1-(2-(2-(trifluoromethoxy)phenyl)ethanol (2.2 g) using the procedure of synthesis method B (boron trifluoride diethyletherate was used instead of titanium(IV)chloride and only ⅓ of the intermediate ethyl 5-(trifluoromethoxy)isochroman-1-carboxylate was used in last step). The obtained base was converted to HCl salt using salt formation method A (HCl in Et₂O and DCM as solvent) (Yield 192 mg).
¹H NMR (DMSO-d₆) δ ppm 10.64 (s, 2H), 7.27-7.56 (m, 3H), 5.94 (s, 1H), 4.17 (dt, 1H), 3.83-3.96 (m, 1H), 3.90 (br. s, 4H), 2.75-2.99 (m, 2H).

Example 80

Enantiomer-1 of 2-(3-ethylisochroman-1-yl)-4,5-dihydro-1H-imidazole, HCl salt

The title compound, faster eluating enantiomer, (138 mg) was prepared from compound of example 8 (500 mg) with separation method L.
¹H NMR (CD₃OD) δ ppm 7.26 (d, 2H), 7.06 (t, 1H), 5.76 (s, 1H), 4.14-4.25 (m, 1H), 3.89-4.02 (m, 5H), 2.79-3.02 (m, 2H), 2.68 (q, 2H), 1.22 (t, 3H).

Example 81

2-(3-(2-Fluoroethyl)-5-methylisochroman-1-yl)-4,5-dihydro-1H-imidazole, HCl salt Step 1:
1-(2-(Benzyloxy)pent-4-enyl)-2-methylbenzene To a suspension of NaH (4.9 g, 127.8 mmol) in THF (150 ml) was added 1-o-tolylpent-4-en-2-ol (15 g in THF, 85.22 mmol) at 0° C. stirred for 30 min. Then added benzylbromide (17.85 g, 102.2 mmol) at 0° C. then reaction mixture was stirred for room temperature for 16 h. Then quenched with ice cold H₂O and concentrated under reduced pressure to afford crude compound. The title compound was separated by separation method-A and E. (Yield 13.0 g).

Step 2: 3-(Benzyloxy)-4-o-tolylbutanal

To a solution of 1-(2-(benzyloxy)pent-4-enyl)-2-methylbenzene (5.0 g, 18.72 mmol) in DCM (100 ml) was passed O₃ gas at −78° C. for 3 h. The reaction mixture was quenched with TEA (5 ml) at −78° C., and stirred for room temperature for 5 h. The title compound was purified by separation methods A and E. (Yield 2.0 g).

Step 3: 3-(Benzyloxy)-4-o-tolylbutan-1-ol

To a solution of 3-(benzyloxy)-4-o-tolylbutanal (4.0 g, 14.81 mmol) in MeOH (50 ml) was added NaBH₄ (1.13 g, 29.62 mmol) at 0° C. and stirred at room temperature for 2 h. The reaction mixture was quenched with water and concentrated under reduced pressure to afford crude compound. The title compound was purified by separation methods A and E. (Yield 3.0 g).

Step 4:
1-(2-(Benzyloxy)-4-fluorobutyl)-2-methylbenzene

To a solution of 3-(benzyloxy)-4-o-tolylbutan-1-ol (3.0 g, 11.11 mmol) in DCM (50 ml) was added DAST (2.9 ml, 22.22 mmol) at 0° C. and stirred at room temperature for 5 h. Then cooled to 0° C. and quenched with NH₄Cl (10 ml). The title compound was purified by separation methods A and E. (Yield 1.5 g).

Step 5: 4-Fluoro-1-o-tolylbutan-2-ol

To a solution of 1-(2-(benzyloxy)-4-fluorobutyl)-2-methylbenzene (3.0 g, 11.03 mmol) in MeOH (50 ml) was added 10% Pd/C (0.3 g) under nitrogen and stirred at 40 psi for 5 h. The reaction mixture was filtered through Celite and concentrated under reduced pressure to afford crude compound. The title compound was purified by separation method E. (Yield 1.5 g).

Step 6: Ethyl 3-(2-fluoroethyl)-5-methylisochroman-1-carboxylate

The title compound was prepared by synthesis method A from 4-fluoro-1-o-tolylbutan-2-ol (3.0 g, 16.48 mmol) and purified by separation methods A and E (Yield 1.0 g).

Step 7: 2-(3-(2-Fluoroethyl)-5-methylisochroman-1-yl)-4,5-dihydro-1H-imidazole, HCl salt The title compound was prepared from 3-(2-fluoroethyl)-5-methylisochroman-1-carboxylate (200 mg) by the synthesis method A and salt formation method A and isolated with the separation method D. (Yield 50 mg).
¹H NMR (CD₃OD) δ ppm 7.15-7.34 (m, 2H), 7.01-7.12 (m, 1H), 5.83 (s, 1H), 4.53-4.81 (m, 2H), 3.94-4.10 (m, 5H), 2.30 (s, 3H), 2.79-2.94 (m, 1H), 2.59-2.79 (m, 1H), 1.98-2.27 (m, 2H).

Example 82

Enantiomer of 2-(5-methoxyisochroman-1-yl)-4,5-dihydro-1H-imidazole

The title compound, faster eluating enantiomer, (77 mg) was prepared from compound of example 17 (160 mg) with separation method L.
¹H NMR (DMSO-d₆) δ ppm 10.54 (br. s, 2H), 7.27 (t, 1H), 6.99 (d, 1H), 6.85 (d, 1H), 5.83 (br. s., 1H), 4.10-4.17 (m, 1H), 3.87 (br. s, 4H) 3.82-3.86 (m, 1H), 3.81 (s, 3H), 2.65-2.81 (m, 2H).

Example 83

Enantiomer-2 of 2-5-Bromo-3-(2,2,2-trifluoroethyl)isochroman-1-yl)-4,5-dihydro-1H-imidazole, HCl-salt The title compound was prepared from enantiomer-2 of ethyl 1-(2-bromophenyl)-4,4,4-trifluorobutan-2-ol (500 mg, example 68, step 2) by the synthesis method B and isolated with the separation method E. The obtained base was converted to HCl salt using salt formation method A (HCl in Et$_2$O and DCM as solvent) (Yield 290 mg).

$^1$H NMR (DMSO-d$_6$) δ ppm 10.61 (br. s., 1.24H), 10.50 (br. s, 0.76H), 7.61-7.79 (overlapping m, 1H), 7.21-7.39 (overlapping m, 2H), 5.98 (br.s, 0.62H), 5.97 (bs.s, 0.38H), 4.24 (dd, 1H), 3.83-3.95 (m, 4H), 2.60-3.08 (m, 4H).

Example 84

2-(3-(2,2-Difluoroethyl)-5-methylisochroman-1-yl)-4,5-dihydro-1H-imidazole, HCl salt

Step 1: 1-(2-(Benzyloxy)-4,4-difluorobutyl)-2-methylbenzene

To a solution of 3-(benzyloxy)-4-o-tolylbutan-1-ol (10 g, 37.04 mmol, Example 81, Step 3) in DCM (100 ml) was added DAST (10 ml, Wt/V) at 0° C. and stirred at room temperature for 5 h. Then cooled to 0° C. and quenched with NH$_4$Cl (50 ml). The title compound was purified by separation methods A and E. (Yield 7.0 g).

Step 2: 4,4-Difluoro-1-o-tolylbutan-2-ol

To a solution of 1-(2-(benzyloxy)-4,4-difluorobutyl)-2-methylbenzene (10 g, 34.48 mmol) in MeOH (150 ml) was added 10% Pd/C (1.0 g) under nitrogen and stirred at 40 psi for 5 h. The reaction mixture was filtered through Celite and concentrated under reduced pressure to afford crude compound. The title compound was purified by separation method E. (Yield 6.0 g).

Step 3: Ethyl 3-(2,2-Difluoroethyl)-5-methylisochroman-1-carboxylate

The title compound was prepared by synthesis method A from 4,4-difluoro-1-o-tolylbutan-2-ol (5.0 g, 25.0 mmol) and purified by separation methods A and E. (Yield 1.5 g).

Step 4: 2-(3-(2,2-Difluoroethyl)-5-methylisochroman-1-yl)-4,5-dihydro-1H-imidazole, HCl salt The title compound was prepared from ethyl 3-(2,2-difluoroethyl)-5-methylisochroman-1-carboxylate (200 mg) by the synthesis method A and salt formation method A, and isolated with the separation method D. (Yield 130 mg).

$^1$H NMR (CD$_3$OD) δ ppm 7.15-7.31 (m, 2H), 7.05 (d, 1H), 6.03-6.30 (m, 1H), 5.83 (s, 1H), 4.09 (ddd, 1H), 3.96-4.04 (m, 4H), 2.86 (dd, 1H), 2.73 (dd, 1H), 2.19-2.40 (m, 5H).

Example 85

2-(7-Methoxy-3,5-dimethylisochroman-1-yl)-4,5-dihydro-1H-imidazole

The mixture of 2-bromo-5-methoxytoluene (2 g) and THF (10 ml) at −78° C. was treated with n-butyl lithium (2.5M heptane sol 8.8 ml), and stirred for 15 min followed by the addition of propylene oxide (0.9 ml) in THF (5 ml). After stirring for 30 min at −78° C., the reaction mixture was allowed to reach ambient temperature, and the intermediate 1-(4-methoxy-2-methylphenyl)propan-2-ol was purified with separation methods A and E (EtOAc/heptanes), respectively. The mixture of ethyl 2,2-diethoxyacetate (0.6 ml), 1-(4-methoxy-2-methylphenyl)propan-2-ol (0.5 g) and DCE (4 ml) was stirred in ice-bath temperature, and boron trifluoride diethyl etherate was added (0.7 ml) followed by refluxing for 4 hrs. The intermediate ethyl 7-methoxy-3,5-dimethylisochroman-1-carboxylate (0.05 g) was purified with separation methods B and E (ethyl acetate/heptanes), respectively. The title compound was synthesized using the procedure of synthesis method A step 3 and separation method D (diethyl ether/heptanes). (Yield 0.01 g).

$^1$H NMR (CDCl$_3$) δ ppm 6.74 (dd, 2H), 5.45 (d, 1 h), 3.83-3.92 (m, 1H), 3.75 (d, 3H), 3.40-3.71 (br, 3H), 2.368-2.68 (m, 2H), 2.2 (s, 3H), 1.37 (dd, 3H).

Example 86

Enantiomer-2 of 2-((3)-5-methyl-3-(2,2,2-trifluoroethyl)isochroman-1-yl)-4,5-dihydro-1H-imidazole, hydrochloride

Step 1: Enantiomer of (4,4,4-Trifluoro-1-o-tolylbutan-2-ol

To a solution of 4,4,4-trifluoro-1-o-tolylbutan-2-one (7.0 g, 32.4 mmol, Example 52 step 1) in MeOH (150 ml) was added NaBH (1.84 g, 48.6 mmol) at 0° C. and stirred at RT for 1 h. Then the reaction mixture was quenched with MeOH and concentrated under reduced pressure to afford crude compound. The title compound was purified by separation methods A, E and H. Yield (1.4 g). The enantiomer showed up at t$_r$=7.0 min with Chiralcel OD-H (4.6×250 mm) 5μ, hexane:2-PrOH:TFA (90:10:0.1), 1 ml/min.

Step 2: Enantiomer-2 of 2-((3)-5-methyl-3-(2,2,2-trifluoroethyl)isochroman-1-yl)-4,5-dihydro-1H-imidazole, hydrochloride Title compound was synthesized as in the example 52 from enantiomer-2 of 4,4,4-trifluoro-1-o-tolylbutan-2-ol (1.19 g) and converted to HCl salt according to the salt formation method A. (Yield 74 mg).

$^1$H NMR (DMSO-d$_6$) δ ppm 10.52 (br s, 1.5H), 10.13 (br. s, 2H), 7.16-7.29 (m, 2H), 7.05-7.13 (m, 1H), 5.93 (s, 0.75H), 5.89 (s, 0.22H), 4.14-4.28 (m, 1H), 3.83-3.93 (m, 4H), 2.61-2.91 (m, 4H), 2.23 (s, 3H).

Example 87

2-(5-(Methylthio)isochroman-1-yl)-4,5-dihydro-1H-imidazole

Step 1: Ethyl 3,4-dihydro-5-(methylthio)-1H-isochromene-1-carboxylate

To a solution of ethyl 5-bromo isocroman-1-carboxylate (Synthesis method A1 and A2, 0.5 g, 1.75 mmol), NaSMe (0.18, 3.3 mmol) and CuBr (0.435 g, 1.8 mmol) in DMF (10 ml) was heated to 90° C. under microwave irradiation for 15 min. The title compound was purified by separation methods D and E. (Yield 100 mg).

Step 2: 2-(5-(Methylthio)isochroman-1-yl)-4,5-dihydro-1H-imidazole

The title compound was prepared from ethyl 5-(methylthio)isochroman-1-carboxylate (490 mg) by the synthesis method A and isolated with the separation method G. (Yield 380 mg).

$^1$H NMR (CDCl3) δ ppm 7.17-7.22 (m, 2H), 7.08-7.13 (m, 1H), 5.44 (s, 1H), 4.24 (ddd, 1H), 3.89 (ddd, 1H), 3.45-3.82 (m, 4H), 2.70-2.93 (m, 2H), 2.46 (s, 3H).

Example 88

Enantiomer-2 of 2-((3)-5-bromo-3-propylisochroman-1-yl)-4,5-dihydro-1H-imidazole, hydrochloride Step 1: Enantiomer-2 of 1-(2-bromophenyl)pentan-2-ol To a solution of 2-(2-bromophenyl)acetaldehyde (16 g, 80.8 mmol) in THF (100 ml) was added propyl magnesium bromide (48 ml (2.0 M) in THF), 97 mmol) at 0° C. then stirred at room temperature for 5 h. The reaction mixture was quenched with ammonium chloride then the title compound was purified by separation methods A, E and H. (Yield 740 mg). The enantiomer-2 showed up at $t_r$=5.70 min with Chiralcel OD-H (4.6×250 mm) 5μ, hexane:2-PrOH:TFA (90:5:0.1), 1 ml/min.

Step 2: Enantiomer of 2-((3)-5-bromo-3-propylisochroman-1-yl)-4,5-dihydro-1H-imidazole, hydrochloride The title compound was synthesized from enantiomer-2 of 1-(2-bromophenyl)pentan-2-ol (1.0 g) using the procedure of synthesis method B and salt formation method A. (Yield 510 mg). Boron trifluoride diethyletherate was used instead of titanium(IV)chloride.

$^1$H NMR (DMSO-d$_6$) δ ppm 10.73 (br s, 1.8H), 10.16 (br s, 0.1H), 7.70-7.63 (m, 1H), 7.21-7.34 (m, 2H), 5.92 (br s, 1H), 3.78-3.94 (m, 5H), 2.78-2.88 (m, 1H), 2.61 (dd, 1H), 1.59-1.72 (m, 2H), 1.35-1.57 (m, 2H), 0.93 (m, 3H).

Example 89

Enantiomer-2 of 2-((3-(2,2-difluoroethyl)-5-methylisochroman-1-yl)-4,5-dihydro-1H-imidazole hydrochloride Step 1: Enantiomer of 1-(2-(benzyloxy)-4,4-difluorobutyl)-2-methylbenzene The racemic 1-(2-(benzyloxy)-4,4-difluorobutyl)-2-methylbenzene (Example 84, Step 2) was separated to enantiomers with separation method H (retention time 8.6 min, 1 ml/min, Chiralcel OJ-H, 4.6×250 min, 90:10:0.1 Hexane:iPrOH:TFA) (Yield 4.0 g).

Step 2: Enantiomer-2 of 2-(-3-(2,2-difluoroethyl)-5-methylisochroman-1-yl)-4,5-dihydro-1H-imidazole, hydrochloride The title compound was synthesized from enantiomer-2 of (3)-ethyl 3-(2,2-difluoroethyl)-5-methylisochroman-1-carboxylate (250 mg) using the procedure of synthesis method A3 and salt formation method A. (Yield 100 mg).

$^1$H NMR (DMSO-d$_6$) δ ppm 10.67 (s, 2H), 7.09-7.23 (m, 3H), 6.14-6-45 (tt, 1H), 5.93 (s, 1H), 3.97-4.08 (m, 1H), 3.85-3.92 (m, 4H), 2.81 (dd, 1H), 2.63-2.74 (m, 1H), 2.24-2.37 (m, 2H), 2.23 (s, 3H).

Example 90

2-(5-(Difluoromethoxy)isochroman-1-yl)-4,5-dihydro-1H-imidazole, hydrochloride

The title compound was synthesized from ethyl 5-(difluoromethoxy)isochroman-1-carboxylate (220 mg) using the procedure of synthesis method A3 and salt formation method A. (Yield 180 mg).

$^1$H NMR (DMSO-d$_6$) δ ppm 10.41 (s, 2H), 7.38 (t, 1H), 7.27 (t, 1H), 7.22 (d, 1H), 7.15 (d, 1H), 5.85 (s, 1H), 4.14 (td, 1H), 3.83-3.95 (m, 5H), 2.72-2.90 (m, 2H).

Example 91

2-((3R)-3-ethyl-5-methoxyisochroman-1-yl)-4,5-dihydro-1H-imidazole

The title compound was prepared from (R)-ethyl 5-bromo-3-ethylisochroman-1-carboxylate (700 mg) by the synthesis methods E (with 2-di-tert-butylphosphino-3,4,5,6-tetramethyl-2',4',6'-triisopropyl-1,1'-biphenyl, reflux) and A. C—O coupling reaction (E) yielded free acid which was further methylated before the final reaction step (synthesis method A). The title compound was obtained by concentration of the reaction mixture. (Yield 169 mg).

$^1$H NMR (CD$_3$OD) δ ppm 7.00-7.22 (m, 1H), 6.76-6.85 (m, 2H), 5.38 (s, 1H), 3.82 (s, 3H), 3.45-3.71 (m, 4H), 2.82 (dd, 1H), 2.41 (dd, 1H), 1.53-1.81 (m, 2H), 0.95-1.12 (m, 3H).

Example 92

Enantiomer-1 of 2-(5-chloroisochroman-1-yl)-4,5-dihydro-1H-imidazole, HCl salt

The title compound, faster eluating enantiomer, (43 mg) was prepared from compound of example 8 (500 mg) with separation method L.

$^1$H NMR (DMSO-d$_6$) δ ppm 10.50 (br. s, 2H), 7.51 (d, 1H), 7.35 (t, 1H), 7.25 (d, 1H), 5.86 (br. s., 1H), 4.13-4.22 (m, 1H), 3.83-3.99 (m, 5H), 2.78-2.96 (m, 2H).

Example 93

2-((3R)-5-(difluoromethoxy)-3-methylisochroman-1-yl)-4,5-dihydro-1H-imidazole, hydrochloride Step 1: (R)-1-(2-bromophenyl)propan-2-ol To a solution of 1-(2-bromophenyl) propane-2-one (30 g, 140 mmol) in MeOH (100 ml) was added NaBH$_4$ (6.09 g, 210 mmol) at 0° C. and stirred at room temperature for 2 h. The reaction mixture was quenched with water and concentrated under reduced pressure to afford crude compound. The title compound was purified by separation methods A, E and M (Yield 28.0 g). The enantiomer-1 showed up at $t_r$=7.86 min with Chiralcel OD-H (4.6×250 mm) 5μ, hexane:2-PrOH:TFA (90:5:0.1), 1 ml/min.

Step 2: (3R)-ethyl 5-bromo-3-methylisochroman-1-carboxylate

The title compound was prepared by synthesis method A1 and A2 from R-2-(2-bromophenyl) and purified by separation methods A and E. (Yield 2.0 g)

Step 3: (3R)-ethyl 5-hydroxy-3-methylisochroman-1-carboxylate

To a solution of (3R)-ethyl 5bromo-3-methylisochroman-1-carboxylate (2.0 g, 5.95 mmol) in dioxane (50 ml) and water (10 ml) was added KOH (1.37 g, 35.7 mmol), tetramethyl dit-butyl XPhos (0.28 g, 0.06 mmol) and $Pd_2(dba)_3$ (0.06 g, 0.06 mmol) at room temperature. Then, reaction mixture was degassed three times with $N_2$ and stirred at 100° C. for 16 h. The reaction mixture was quenched with MeOH and concentrated under reduced pressure to afford crude compound. The crude was dissolved in EtOH (80 ml) added $H_2SO_4$ (1.0 ml) then stirred at 80° C. for 5 h. The solvent was removed by evaporation to get the crude compound. The title compound was purified by separation methods A and E. (Yield 100 mg).

Step 4: (3R)-ethyl 5-(difluoromethoxy)-3-methylisochroman-1-carboxylate

To a solution of (3R)-ethyl 5bromo-3-methylisochroman-1-carboxylate (0.25 g, 1.05 mmol) in DMF (5.0 ml) was added $K_2CO_3$ (0.184 g, 1.35 mmol). Then difluoromonochloro-methane gas was purged for at room temperature for 2 h and stirred at 50° C. for 4 h. The reaction mixture was quenched with water. The title compound was purified by separation methods A and E. (Yield 40 mg). The enantiomer-1 (i.e., (R) showed up at $t_r$=4.71 min with Chiralcel OD-H (4.6×250 mm) 5μ, hexane:2-PrOH:TFA (90:5:0.1), 1 ml/min.

Step 5: 2-((3R)-5-(difluoromethoxy)-3-methylisochroman-1-yl)-4,5-dihydro-1H-imidazole, hydrochloride The title compound was synthesized from (3R)-ethyl 5-(difluoromethoxy)-3-methylisochroman-1-carboxylate (250 mg) using the procedure of synthesis method A3 and salt formation method A. (Yield 200 mg).
$^1$H NMR (DMSO-$d_6$) δ ppm 10.81 (s, 1.75H), 10.22 (s, 0.14H), 7.36 (t, 1H), 7.29 (t, 1H), 7.17-7.23 (m, 2H), 5.98 (s, 0.07 H), 5.96 (s, 0.88 H), 3.84-4.00 (m, 5H, overlaps with $H_2O$ signal), 2.81-2.92 (m, 1H), 2.57 (dd, 0.89H), 2.45 (dd, 0.09H), 1.36 (d, 2.65H), 1.33 (d, 0.29H).

Example 94

Enantiomer of 2-(5-bromo-3-ethylisochroman-1-yl)-4,5-dihydro-1H-imidazole

Step 1: Enantiomer of 1-(2-bromophenyl)butan-2-ol

To a solution of 2-(2-bromophenyl) acetaldehyde (15 g, 75.37 mmol) in THF (100 ml) was added propyl magnesium bromide (1.0 M in THF) (15.13 g, 113.6 mmol) at 0° C. then stirred at RT for 3 h. The reaction mixture was quenched with ammonium chloride then the title compound was purified by separation methods A, E and M. (Yield 7.0 g). The enantiomer showed up at $t_r$=13.6 min with Chiralcel OJH (4.6×250 mm) 5μ, hexane:ethanol (98:02), 1 ml/min.

Step 2: Enantiomer of 2-(-5-bromo-3-ethylisochroman-1-yl)-4,5-dihydro-1H-imidazole The title compound was prepared from enantiomer of ethyl 3-(2,2-difluoroethyl)-5-methylisochroman-1-carboxylate (500 mg) by the synthesis method A and isolated with the separation method E. (Yield 470 mg).
$^1$H NMR (CD$_3$OD) δ ppm 7.44-7.58 (m, 1H), 7.24 (d, 1H), 7.00-7.16 (m, 1H), 5.39 (s, 1H), 3.49-3.73 (m, 5H), 2.82-2.90 (m, 1H), 2.42-2.64 (m, 1H), 1.54-1.82 (m, 2H), 0.92-1.12 (m, 3H).

Example 95

Enantiomer-1 of 2-(5-chloroisochroman-1-yl)-4,5-dihydro-1H-imidazole, HCl salt

The title compound, faster eluating enantiomer, (28 mg) was prepared from Example 2 (130 mg) with separation method L.
$^1$H NMR (DMSO-$d_6$) δ ppm 10.44 (br. s., 2H), 7.61-7.77 (m, 1H), 7.17-7.34 (m, 2H), 5.85 (br. s., 1H), 4.08-4.22 (m, 1H), 3.81-4.03 (m, 5H), 2.70-2.93 (m, 2H).

Example 96

Enantiomer-2 of 2-(3-ethylisochroman-1-yl)-4,5-dihydro-1H-imidazole

The title compound, slower eluating enantiomer, (110 mg) was prepared from compound of example 8 (500 mg) with separation method L.
$^1$H NMR (CD$_3$OD) δ ppm 7.26 (d, 2H), 7.06 (t, 1H), 5.76 (s, 1H), 4.14-4.25 (m, 1H), 3.89-4.02 (m, 5H), 2.79-3.02 (m, 2H), 2.68 (q, 2H), 1.22 (t, 3H).

Example 97

Enantiomer-2 of 2-(5-methoxyisochroman-1-yl)-4,5-dihydro-1H-Imidazole, HCl salt

The title compound, slower eluating enantiomer, (77 mg) was prepared from compound of example 17 (160 mg) with separation method L.
$^1$H NMR (DMSO-$d_6$) δ ppm 10.45 (br. s, 2H), 7.27 (t, 1H), 6.99 (d, 1H), 6.83 (d, 1H), 5.81 (br. s., 1H), 4.10-4.17 (m, 1H), 3.87 (br. s, 4H) 3.82-3.86 (m, 1H), 3.81 (s, 3H), 2.65-2.80 (m, 2H).

Example 98

2-(1-Methyl-1,3-dihydrobenzo[de]isochromen-1-yl)-4,5-dihydro-1H-imidazole

The mixture of NaH (0.18 g), methyl 1,3-dihydrobenzo[de]isochromene-1-carboxylate (0.5 g) and DMF (2 ml), toluene (2 ml) and THF (6 ml) was stirred in ice-bath temperature. Iodomethane (0.7 ml) was added and the mixture was stirred at ambient temperature for 3 hrs. The intermediate methyl 1-methyl-1,3-dihydrobenzo[de]isochromene-1-carboxylate (0.3 g) was purified with separation method A and E (EtOAc/heptanes), and the title compound was synthesized using the procedure of synthesis method A step 3 and separation method E (EtOAc/DCM/triethyl amine 10/20/1). (Yield 0.1 g).

$^1$H NMR (CDCl$_3$) δ ppm 7.77 (td, 2H), 7.41-7.53 (m, 3H), 7.21 (dd, 1H), 5.14 (q, 2H), 4.92 (br, 1H), 3.14-4.19 (br, 4H), 1.90 (s, 3H).

Example 99

2-(5-(Difluoromethyl)isochroman-1-yl)-4,5-dihydro-1H-imidazole, hydrochloride

Step 1: Ethyl 5-(difluoromethyl)isochroman-1-carboxylate

To a solution of ethyl 5-formylisochroman-1-carboxylate (200 mg) in dichloromethane (1 mL) was added diethylaminosulfur trifluoride (275 mg) and the solution was stirred at room temperature for 22 hours. Solvents were evaporated and the crude product was purified by separation method E (EtOAc-heptane). (Yield 153 mg).

$^1$H NMR (CDCl$_3$) δ ppm 7.53 (d, 1H), 7.46 (d, 1H), 7.24-7.33 (m, 1H), 6.72 (t, 1H), 5.36 (s, 1H), 4.21-4.38 (m, 3H), 4.01-4.11 (m, 1H), 2.90-3.06 (m, 2H), 1.32 (t, 3H).

Step 2: 2-(5-(Difluoromethyl)isochroman-1-yl)-4,5-dihydro-1H-imidazole, hydrochloride The title compound was synthesized from ethyl 5-(difluoromethyl)isochroman-1-carboxylate (153 mg) using the procedure of synthesis method A3 and salt formation method A (Yield 87 mg).

$^1$H NMR (DMSO-d$_6$) δ ppm 10.51 (br. s, 2H), 7.58 (t, 1H), 7.42-7.48 (m, 2H), 7.21 (t, 1H), 5.93 (s, 1H), 4.11-4.20 (m, 1H), 3.82-3.94 (m, 5H), 2.87-3.11 (m, 2H).

Example 100

Enantiomer-2 of 2-(5-chloroisochroman-1-yl)-4,5-dihydro-1H-imidazole, HCl salt

The title compound, slower eluting enantiomer, (40 mg) was prepared from compound of example 8 (500 mg) with separation method L.

$^1$H NMR (DMSO-d$_6$) δ ppm 10.50 (br. s, 2H), 7.51 (d, 1H), 7.35 (t, 1H), 7.25 (d, 1H), 5.86 (br. s., 1H), 4.13-4.22 (m, 1H), 3.83-3.99 (m, 5H), 2.78-2.96 (m, 2H).

Example 101

Enantiomer-2 of 2-(5-bromoisochroman-1-yl)-4,5-dihydro-1H-imidazole, HCl salt

The title compound, slower eluting enantiomer, (22 mg) was prepared from compound of example 2 (130 mg) with separation method L.

$^1$H NMR (DMSO-d$_6$) δ ppm 10.44 (br. s., 2H), 7.61-7.77 (m, 1H), 7.17-7.34 (m, 2H), 5.85 (br. s., 1H), 4.08-4.22 (m, 1H), 3.81-4.03 (m, 5H), 2.70-2.93 (m, 2H).

Example 102

2-(1,3-Dihydrobenzo[de]isochromen-1-yl)-4,5-dihydro-1H-imidazole, hydrochloride

To a solution of 1,3-Dihydrobenzo[de]isochromen-1-ol (100 mg) in acetonitrile (3 mL) at 0° C. was added Zn(II) iodide (86 mg) and suspension was stirred at 0° C. for 10 minutes. Trimethylsilyl cyanide (672 µL) was added and the reaction mixture was stirred at room temperature overnight. Solution of saturated NaHCO$_3$ (10 mL) was added and the mixture was extracted with ethyl acetate (2×15 mL). Combined organic phases were washed with brine and dried with Na$_2$SO$_4$. Evaporation of solvents afforded 110 mg 1,3-dihydrobenzo[de]isochromene-1-carbonitrile that was mixed with ethylene diamine mono-p-toluenesulfonic acid salt (157 mg) and the mixture was heated to 200° C. After 3 hours the reaction mixture was cooled to room temperature and taken to mixture of dichloromethane (10 ml) and aqueous NaHCO$_3$ (1:1 saturated solution/water). Phases were separated and aqueous phase was extracted with dichloromethane (5 mL). Combined organic phases were dried with Na$_2$SO$_4$ and concentrated. The evaporation residue was purified by separation method E (aq.NH$_3$-MeOH-dichloromethane). The obtained 2-(1,3-dihydrobenzo[de]isochromen-1-yl)-4,5-dihydro-1H-imidazole was converted to the title compound using salt formation method A.

$^1$H NMR (DMSO-d$_6$) δ ppm 10.56 (s, 2H), 7.99 (d, 1H), 7.91 (d, 1H), 7.53-7.62 (m, 2H), 7.41 (d, 2H), 6.25 (s, 1H), 5.22 (AB q, 2H), 3.90-4.05 (m, 4H).

Example 103

Enantiomer of 2-(1-methyl-1,3-dihydrobenzo[de]isochromen-1-yl)-4,5-dihydro-1H-imidazole The title compound, slower eluating enantiomer, (10 mg) was prepared from compound of example 98 (1.2 g) with separation method H.

$^1$H NMR (CDOD$_3$) δ ppm 7.81 (dd, 1H), 7.77 (d, 1H), 7.41-7.53 (m, 3H), 7.24 (dd, 1H), 5.14 (s, 2H), 4.76-4.84 (m, 4H, methanol), 1.85 (s, 3H).

Example 104

2-(3-Methyl-1,3-dihydrobenzo[de]isochromen-1-yl)-4,5-dihydro-1H-imidazole, hydrochloride To a solution of 3-methylbenzo[de]isochromen-1(3H)-one (1.38 g) in dichloromethane (34 mL) at −78° C. was added diisobutylaluminum hydride (10.5 mL, 20% solution in toluene) over 25 minutes. After 2 hours 10% solution aqueous solution of citric acid (20 mL) was added and the mixture was stirred for 25 minutes at room temperature. To the resulting suspension was added water (20 mL) and dichloromethane (20 mL) and the layers were separated. The aqueous phase was extracted with ethyl acetate (2×20 mL) and the combined organic phases were washed with brine, dried with Na$_2$SO$_4$ and concentrated. The evaporation residue that solidified in refrigerator was purified by trituration with heptane. The obtained 3-methyl-1,3-dihydrobenzo[de]isochromen-1-ol (0.92 g, mixture of diastereomers) was dissolved in dichloromethane (16 mL) and cooled to 0° C. Trimethylsilyl cyanide (1.71 mL) was added, followed by boron trifluoride triethyl etherate (1.14 mL). After 1.5 hours saturated solution of NaHCO$_3$ (10 mL) was added and the mixture was extracted with dichloromethane. Combined organic phases were washed with brine, dried (Na$_2$SO$_4$) and concentrated. Purification of the evaporation residue by trituration with heptane afforded 0.68 g of 3-methyl-1,3-dihydrobenzo[de]isochromene-1-carbonitrile (mixture of diastereomers).

3-Methyl-1,3-dihydrobenzo[de]isochromene-1-carbonitrile (100 mg) was mixed with ethylene diamine mono-p-toluenesulfonic acid salt (111 mg) and the mixture was heated to 200° C. After 3 hours reaction was cooled to room temperature. Purification of the mixture by column chromatography with neutral alumina (ethyl acetate-heptane) afforded 11 mg of 2-(3-methyl-1,3-dihydrobenzo[de]isochromen-1-yl)-4,5-dihydro-1H-imidazole that was converted to the title compound using salt formation method A. (Yield 10 mg).

$^1$H NMR (DMSO-d$_6$) ppm 10.76 (s, 1H), 10.25 (s, 0.5H), 7.88-8.05 (m, 2H), 7.52-7.66 (m, 2H), 7.30-7.52 (m, 2H), 6.30 (s, 0.3H), 6.27 (s, 0.6H), 5.35 (q, 0.6H), 3.92 (q, 0.3H), 3.86-4.08 (m, 4H), 1.74 (d; 2H), 1.66 (d, 1H).

Example 105

2-(3-Ethyl-1,3-dihydrobenzo[de]isochromen-1-yl)-4,5-dihydro-1H-imidazole, hydrochloride To a solution of 3-ethylbenzo[de]isochromen-1 (3H)-one (0.55 g) in dichloromethane (7 mL) at −78° C. was added diisobutylaluminum hydride (2.19 mL, 20% solution in toluene). After 3 hours 10% solution aqeuous solution of citric acid (10 mL) was added and the mixture was stirred for 15 minutes at room temperature. Phases were separated and the aqueous phase was extracted with ethyl acetate (2×10 mL). The combined organic phases were washed with brine, dried with Na$_2$SO$_4$ and concentrated. The purification of evaporation residue by column chromatography (ethyl acetate-heptanes) afforded 3-ethyl-1,3-dihydrobenzo[de]isochromen-1-ol (0.22 g, mixture of diastereomers) that was dissolved in dichloromethane (5 mL). Solution was cooled to 0° C. and trimethylsilyl cyanide (0.39 mL) was added, followed by boron trifluoride triethyl etherate (0.26 mL). After 2.5 hours saturated solution of NaHCO$_3$ (10 mL) was added and the mixture was extracted with dichloromethane. Combined organic phases were washed with brine, dried (Na$_2$SO$_4$) and concentrated. The evaporation residue containing the mixture of diastereomers of 3-ethyl-1,3-dihydrobenzo[de]isochromene-1-carbonitrile (170 mg) was mixed with dioxane (2 mL) and 10% aqueous solution of NaOH (1.6 mL) was added and the mixture was heated to reflux. After 13 hours, reaction mixture was cooled to room temperature and water (10 mL) and dichloromethane (10 ml) were added. Aqueous phase was acidified with 4M HCl and extracted with EtOAc (3×10 mL). Combined organic phases were washed with brine, dried with Na$_2$SO$_4$ and concentrated. The evaporation residue containing the 3-ethyl-1,3-dihydrobenzo[de]isochromene-1-carboxylic acid (80 mg) was turned to the title compound using synthesis methods A2 and A3 along with the separation method E in A3. The obtained 2-(3-ethyl-1,3-dihydrobenzo[de]isochromen-1-yl)-4,5-dihydro-1H-imidazole was converted to the title compound using salt formation method A. (Yield 5.7 mg).

$^1$H NMR (DMSO-d$_6$) δ ppm 10.73 (br s, 0.9H), 10.42 (br s, 0.7H), 7.99 (dd, 1H), 7.92 (dd, 1H), 7.53-7.63 (m, 2H), 7.31-7.50 (m, 2H), 6.28 (s, 0.4H), 6.24 (s, 0.5H), 5.18-5.23 (m, 0.5H), 5.12 (t, 0.4H), 3.90-4.08 (m, 4H), 2.31-2.43 (m, 0.5H), 1.92-2.24 (m, 1.4H), 1.01-1.12 (m, 3H).

Example 106

Enantiomer of 2-(5-bromo-1-methylisochroman-1-yl)-4,5-dihydro-1H-imidazole

The title compound, faster eluating enantiomer, (160 mg) was prepared from compound of example 11 (400 mg) with separation method H.

$^1$H NMR (DMSO-d$_6$) δ ppm 7.49 (dd, 1H), 7.31 (dd, 1H), 7.11 (dd, 1H), 6.24 (s, H), 3.79-3.98 (m, 2H), 3.41-3.71 (br.s., 2H), 3.10-3.73 (br.s., 2H), 1.62 (s, 3H).

As already mentioned hereinbefore, the compounds of formula I show interesting pharmacological properties, namely they exhibit agonistic activities in adenenergic alpha2 receptors, especially on alpha2A receptor. The said activity is demonstrated with the pharmacological test presented below. The illustrative examples of the present invention were screened for adenenergic alpha2 receptors activities based on procedures described in the literature (Lehtimäki et al, *Eur. J. Pharmacol.* 2008, 599, 65-71). The results are shown in Table 1. Metabolic stability was measured with cryopreserved hepatocytes according to literature method (Di Et al, *Int. J. Pharmaceutics,* 2006, 317, 54-60).

TABLE 1

| Alpha2A agonistic activity in vitro. | | |
|---|---|---|
| Compound of Example | Alpha2A Agonism pEC$_{50}$ | Alpha2A Intrinsic Activity |
| 1 | 8.4 | 0.89 |
| 2 | 7.8 | 0.85 |
| 3 | 7.2 | 0.95 |
| 4 | 8.1 | 0.85 |
| 5 | 5.9 | 0.59 |
| 6 | 7.4 | 0.53 |
| 7 | 7.4 | 0.81 |
| 8 | 7.4 | 0.77 |
| 9 | 6.7 | 0.73 |
| 10 | 7.7 | 0.90 |
| 11 | 7.0 | 0.83 |
| 12 | 5.8 | 0.94 |
| 13 | 5.9 | 0.66 |
| 14 | 5.5 | 0.43 |
| 15 | 7.8 | 0.88 |
| 16 | 7.3 | 0.51 |
| 17 | 7.6 | 0.81 |
| 18 | 8.7 | 0.81 |
| 19 | 8.3 | 0.81 |
| 20 | 7.2 | 0.87 |
| 21 | 7.3 | 0.73 |
| 22 | 6.0 | 0.33 |
| 23 | 6.5 | 0.68 |
| 24 | 6.1 | 0.20 |
| 25 | 8.5 | 0.82 |
| 26 | 8.4 | 0.82 |
| 27 | 7.6 | 0.69 |
| 28 | 6.0 | 0.64 |
| 29 | 8.7 | 0.99 |
| 30 | 6.1 | 0.60 |
| 31 | 5.9 | 0.43 |
| 32 | 9.0 | 0.92 |
| 33 | 8.8 | 0.93 |
| 34 | 7.2 | 0.78 |
| 35 | 7.8 | 0.80 |
| 36 | 8.8 | 0.90 |
| 37 | 6.5 | 0.63 |
| 38 | 7.9 | 0.92 |
| 39 | 7.8 | 0.67 |
| 40 | 6.5 | 0.31 |
| 41 | 6.6 | 0.27 |
| 42 | 7.4 | 0.62 |
| 43 | 7.3 | 0.58 |
| 44 | 8.1 | 0.83 |
| 45 | 8.2 | 0.73 |
| 46 | 7.1 | 0.45 |
| 47 | 5.7 | 0.22 |
| 48 | 7.6 | 0.58 |
| 49 | 6.9 | 0.35 |
| 50 | 7.6 | 0.90 |
| 51 | 6.2 | 0.26 |
| 52 | 7.0 | 0.41 |
| 53 | 6.5 | 0.72 |
| 54 | 6.0 | 0.16 |

TABLE 1-continued

Alpha2A agonistic activity in vitro.

| Compound of Example | Alpha2A Agonism $pEC_{50}$ | Alpha2A Intrinsic Activity |
|---|---|---|
| 55 | 6.9 | 0.80 |
| 56 | 5.5 | 0.11 |
| 57 | 5.7 | 0.11 |
| 58 | 5.4 | 0.47 |
| 59 | 7.4 | 0.81 |
| 60 | 6.9 | 0.66 |
| 61 | 5.4 | 0.81 |
| 62 | 5.4 | 0.77 |
| 63 | 5.5 | 0.85 |
| 64 | 7.1 | 0.59 |
| 65 | 7.1 | 0.56 |
| 66 | 5.8 | 0.43 |
| 67 | 6.0 | 0.42 |
| 68 | 5.4 | 0.25 |
| 69 | 5.4 | 0.19 |
| 70 | 5.7 | 0.07 |
| 71 | 5.7 | 0.33 |
| 72 | 5.8 | 0.09 |
| 73 | 5.8 | 0.19 |
| 74 | 6.1 | 0.35 |
| 75 | 6.2 | 0.64 |
| 76 | 6.2 | 0.15 |
| 77 | 6.3 | 0.16 |
| 78 | 6.3 | 0.62 |
| 79 | 6.4 | 0.30 |
| 80 | 6.6 | 0.58 |
| 81 | 6.8 | 0.54 |
| 82 | 6.8 | 0.52 |
| 83 | 6.9 | 0.41 |
| 84 | 7.0 | 0.45 |
| 85 | 6.0 | 0.22 |
| 86 | 7.0 | 0.28 |
| 87 | 7.2 | 0.75 |
| 88 | 7.3 | 0.50 |
| 89 | 7.4 | 0.33 |
| 90 | 7.4 | 0.66 |
| 91 | 7.4 | 0.51 |
| 92 | 7.5 | 0.78 |
| 93 | 7.5 | 0.64 |
| 94 | 7.6 | 0.55 |
| 95 | 7.7 | 0.80 |
| 96 | 7.7 | 0.66 |
| 97 | 7.8 | 0.69 |
| 98 | 7.9 | 0.58 |
| 99 | 7.9 | 0.73 |
| 100 | 8.4 | 0.91 |
| 101 | 8.5 | 0.89 |
| 102 | 8.6 | 0.82 |
| 103 | 8.2 | 0.74 |
| 104 | 8.5 | 0.95 |
| 105 | 7.4 | 0.66 |
| 106 | 6.8 | 0.64 |

The compounds of formula I exhibit agonistic activities in adenenergic alpha2 receptors, especially on alpha2A receptor. The present invention thus provides compounds for use as a medicament. Compounds for use in the treatment of disorder, condition or disease where an alpha2 agonist, for example alpha2A agonist is indicated to be useful are also provided. Furthermore, a method for the treatment of disorder, condition or disease where an alpha2 agonist, for example alpha2A agonist is indicated to be useful is provided. In said method an effective amount of at least one compound of formula I is administered to a mammal, such as a human, in need of such treatment. The use of the compounds of formula I for the manufacture of a medicament for the treatment of disorder, condition or disease where an alpha2 agonist, for example alpha2A agonist is indicated to be useful is also provided.

In one embodiment of the invention the aforementioned disorder, condition or disease where an alpha2 agonist, for example alpha2A agonist is indicated to be useful is delirium, hyperactive delirium, insomnia, ADHD, benzodiazepine or alcohol or opioid or tobacco withdrawal, premature ejaculation, hypertension, tachycardia, restless leg syndrome, muscular spasticity, hot flashes, anxiety, post traumatic stress disorder, pain, chronic pelvic pain syndrome, breakthrough cancer pain, or condition wherein sedation or analgesia is needed; for example hyperactive delirium or insomnia.

The invention also provides the compounds of formula I for use as a sedative or analgesic agent.

The compounds of the invention can be administered, for example, enterally, topically or parenterally by means of any pharmaceutical formulation useful for said administration and comprising at least one active compound of formula I in pharmaceutically acceptable and effective amounts together with pharmaceutically acceptable diluents, carriers and/or excipients known in the art. The manufacture of such pharmaceutical formulations is known in the art.

The therapeutic dose to be given to a subject in need of the treatment will vary depending on the compound being administered, the species, the age and the sex of the subject being treated, the particular condition being treated, as well as the route and method of administration, and is easily determined by a person skilled in the art. Accordingly, the typical dosage for oral administration is from 10 ng/kg to 10 mg/kg per day and for parenteral administration from 1 ng/kg to 10 mg/kg for an adult mammal.

The compounds of the invention are given to the subject as such or in combination with one or more other active ingredients, each in its own composition or some or all of the active ingredients combined in a single composition, and/or suitable pharmaceutical excipients. Suitable pharmaceutical excipients include conventionally used excipients and formulation aids, such as fillers, binders, disintegrating agents, lubricants, solvents, gel forming agents, emulsifiers, stabilizers, colorants, and/or preservatives.

The compounds of the invention are formulated into dosage forms using commonly known pharmaceutical manufacturing methods. The dosage forms can be, for example, tablets, capsules, granules, suppositories, emulsions, suspensions, or solutions. Depending on the route of administration and the galenic form, the amount of the active ingredient in a formulation can typically vary between 0.01% and 100% by weight.

A person skilled in the art will appreciate that the embodiments described herein can be modified without departing from the inventive concept. A person skilled in the art also understands that the invention is not limited to the particular embodiments disclosed but is intended to also cover modifications of the embodiments that are within the scope of the invention.

The invention claimed is:

1. A compound of Formula I,

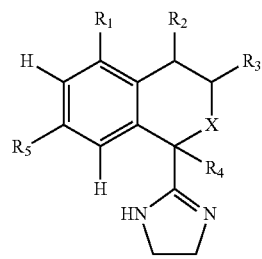

wherein

X is O or S;

$R_1$ is hydroxy, halogen, $(C_1-C_6)$alkyl, halo$(C_1-C_6)$alkyl, $(C_2-C_6)$alkenyl, $(C_2-C_6)$alkynyl, cyclo$(C_3-C_6)$alkyl, $(C_1-C_6)$alkoxy, halo$(C_1-C_6)$alkoxy, hydroxy$(C_1-C_6)$alkyl, cyano, $(C_1-C_6)$alkoxy$(C_1-C_6)$alkyl, $(C_1-C_6)$alkoxy$(C_1-C_6)$alkoxy$(C_1-C_6)$alkyl, hydroxy$(C_1-C_6)$alkoxy, hydroxy$(C_1-C_6)$alkoxy$(C_1-C_6)$alkyl, hydroxy$(C_2-C_6)$alkenyl, $(C_2-C_6)$alkenyloxy$(C_2-C_6)$alkenyl, halo$(C_1-C_6)$alkoxy$(C_1-C_6)$alkyl, halo$(C_1-C_6)$alkoxy-halo$(C_1-C_6)$alkyl, $(C_1-C_6)$alkoxy-halo$(C_1-C_6)$alkoxy, carboxy, $(C_1-C_6)$alkyl-(C=O)—, $(C_1-C_6)$alkoxy-(C=O)—, $(C_1-C_6)$alkyl-(C=O)—O—, halo$(C_1-C_6)$alkyl-(C=O)—, halo$(C_1-C_6)$alkoxy-(C=O)—, $(R_6)_2$N—, $(R_6)_2$N—$(C_1-C_6)$alkyl, $(R_6)_2$N—(C=O)—, $R_6$—(C=O)—N($R_6$)—(C=O)—, $R_6$—(O=S=O)—N($R_6$)—(C=O)—, $R_6$—(C=O)—N($R_6$)—(O=S=O)—, $R_6$—(O=S=O)—N($R_6$)—(O=S=O)—, $(R_6)_2$N—N—, $(R_6)$N=N—, $(R_6)_2$N—O—, $(R_6)$O—N($R_6$)—, $(C_1-C_6)$alkyl-S—, $(C_2-C_6)$alkeny-S—$(C_2-C_6)$alkenyl, hydroxy$(C_1-C_6)$alkyl-S—, hydroxy$(C_1-C_6)$alkyl-S—$(C_1-C_6)$alkyl, $(C_1-C_6)$alkoxy$(C_1-C_6)$alkyl-S—$(C_1-C_6)$alkyl, halo$(C_1-C_6)$alkyl-S—, halo$(C_1-C_6)$alkyl-S—$(C_1-C_6)$alkyl, halo$(C_1-C_6)$alkyl-S-halo$(C_1-C_6)$alkyl, $R_6$—(O=S)—, $(R_6)_2$N—(O=S)—, $R_6$—(O=S=O)—, $(R_6)_2$N—(O=S=O)—, phenyl, phenyl-O—, heteroaryl, heteroaryl-O—, phenyl-N($R_6$)—, heteroaryl-N($R_6$)—, or heteroaryl$(C_1-C_6)$alkyl;

$R_2$ is H, hydroxy, oxo, fluoro, $(C_1-C_6)$alkyl, halo$(C_1-C_6)$alkyl, $(C_2-C_6)$alkenyl, $(C_2-C_6)$alkynyl, cyclo$(C_3-C_6)$alkyl, $(C_1-C_6)$alkoxy, halo$(C_1-C_6)$alkoxy, hydroxy$(C_1-C_6)$alkyl, cyano, $(C_1-C_6)$alkoxy$(C_1-C_6)$alkyl, $(C_1-C_6)$alkoxy$(C_1-C_6)$alkoxy$(C_1-C_6)$alkyl, hydroxy$(C_1-C_6)$alkoxy, hydroxy$(C_1-C_6)$alkoxy$(C_1-C_6)$alkyl, hydroxy$(C_2-C_6)$alkenyl, $(C_2-C_6)$alkenyloxy$(C_2-C_6)$alkenyl, halo$(C_1-C_6)$alkoxy$(C_1-C_6)$alkyl, halo$(C_1-C_6)$alkoxy-halo$(C_1-C_6)$alkyl, $(C_1-C_6)$alkoxy-halo$(C_1-C_6)$alkoxy, carboxy, $(C_1-C_6)$alkyl-(C=O)—, $(C_1-C_6)$alkoxy-(C=O)—, $(C_1-C_6)$alkyl-(C=O)—O—, halo$(C_1-C_6)$alkyl-(C=O)—, halo$(C_1-C_6)$alkoxy-(C=O)—, $(R_6)_2$N—, $(R_6)_2$N—$(C_1-C_6)$alkyl, $(R_6)_2$N—(C=O)—, $R_6$—(C=O)—N($R_6$)—(C=O)—, $R_6$—(O=S=O)—N($R_6$)—(C=O)—, $R_6$—(C=O)—N($R_6$)—(O=S=O)—, $R_6$—(O=S=O)—N($R_6$)—(O=S=O)—, $(R_6)_2$N—N—, $(R_6)$N=N—, $(R_6)_2$N—O—, $(R_6)$O—N—, $(C_1-C_6)$alkyl-S—, $(C_2-C_6)$alkeny-S—$(C_2-C_6)$alkenyl, hydroxy$(C_1-C_6)$alkyl-S—, hydroxy$(C_1-C_6)$alkyl-S—$(C_1-C_6)$alkyl, $(C_1-C_6)$alkoxy$(C_1-C_6)$alkyl-S—$(C_1-C_6)$alkyl, halo$(C_1-C_6)$alkyl-S—, halo$(C_1-C_6)$alkyl-S—$(C_1-C_6)$alkyl, halo$(C_1-C_6)$alkyl-S-halo$(C_1-C_6)$alkyl, $R_6$—(O=S)—, $(R_6)_2$N—(O=S)—, $R_6$—(O=S=O)—, $(R_6)_2$N—(O=S=O)—, phenyl, phenyl-O—, heteroaryl, heteroaryl-O—, phenyl-N($R_6$)—, heteroaryl-N($R_6$)—, or heteroaryl$(C_1-C_6)$alkyl;

$R_3$ is H, $(C_1-C_6)$alkyl, halo$(C_1-C_6)$alkyl, $(C_1-C_6)$alkoxy, halo$(C_1-C_6)$alkoxy, hydroxy$(C_1-C_6)$alkyl, $(C_1-C_6)$alkoxy$(C_1-C_6)$alkyl, or cyclo$(C_3-C_6)$alkyl;

$R_4$ is H, hydroxy, halogen, $(C_1-C_2)$alkyl, or halo$(C_1-C_2)$alkyl;

$R_5$ is H, hydroxy, halogen, $(C_1-C_6)$alkyl, halo$(C_1-C_2)$alkyl, cyclo$(C_3-C_6)$alkyl, $(C_1-C_6)$alkoxy, halo$(C_1-C_6)$alkoxy, hydroxy$(C_1-C_6)$alkyl, phenyl, or heteroaryl; and $R_6$ is, independently at each occurrence, H, $(C_1-C_6)$alkyl, $(C_1-C_6)$alkoxy$(C_1-C_6)$alkyl hydroxy$(C_1-C_6)$alkyl, halo$(C_1-C_6)$alkyl, or $R_6$ and $R_6$ form, together with the atoms they are attached to, a condensed 4, 5, 6, or 7 membered saturated or unsaturated carbocyclic ring or a condensed 4, 5, 6, or 7 membered saturated or unsaturated heterocyclic ring containing 1 or 2 heteroatom(s) selected from N, O or S, wherein said carbocyclic or heterocyclic ring is unsubstituted or substituted with 1 or 2 substituent(s) each independently being hydroxy, oxo, halogen, $(C_1-C_6)$alkyl, hydroxy$(C_1-C_6)$alkyl, or halo$(C_1-C_6)$alkyl-;

or $R_1$ and $R_2$ form, together with the carbon ring atoms to which they are attached, a condensed 4, 5, 6, or 7 membered saturated or unsaturated carbocyclic ring or a condensed 4, 5, 6, or 7 membered saturated or unsaturated heterocyclic ring containing 1 or 2 heteroatom(s) selected from N, O and S, wherein said carbocyclic or heterocyclic ring is unsubstituted or substituted with 1 or 2 substituent(s) each independently being hydroxy, oxo, halogen, $(C_1-C_6)$alkyl, $(C_1-C_6)$alkoxy$(C_1-C_6)$alkyl, hydroxy$(C_1-C_6)$alkyl, or halo$(C_1-C_6)$alkyl;

or $R_2$ and $R_3$ form, together with the carbon ring atoms to which they are attached, a condensed 4, 5, 6, or 7 membered saturated or unsaturated carbocyclic ring or a condensed 4, 5, 6, or 7 membered saturated or unsaturated heterocyclic ring containing 1 or 2 heteroatom(s) selected from N, O and S, wherein said carbocyclic or heterocyclic ring is unsubstituted or substituted with 1 or 2 substituent(s) each independently being hydroxy, oxo, halogen, $(C_1-C_6)$alkyl, $(C_1-C_6)$alkoxy$(C_1-C_6)$alkyl, hydroxy$(C_1-C_6)$alkyl, or halo$(C_1-C_6)$alkyl;

or a pharmaceutically acceptable salt or ester thereof.

2. The compound according to claim 1, wherein $R_1$ is hydroxy, halogen, $(C_1-C_6)$alkyl, halo$(C_1-C_6)$alkyl, $(C_2-C_6)$alkenyl, $(C_2-C_6)$alkynyl, cyclo$(C_3-C_6)$alkyl, $(C_1-C_6)$alkoxy, halo$(C_1-C_6)$alkoxy, hydroxy$(C_1-C_6)$alkyl, cyano, $(C_1-C_2)$alkoxy$(C_1-C_2)$alkyl, hydroxy$(C_1-C_2)$alkoxy, halo$(C_1-C_2)$alkoxy$(C_1-C_2)$alkyl, halo$(C_1-C_2)$alkoxy-halo$(C_1-C_2)$alkyl, $(C_1-C_2)$alkoxy-halo$(C_1-C_2)$alkoxy, carboxy, $(C_1-C_3)$alkyl-(C=O)—, $(C_1-C_3)$alkoxy-(C=O)—, halo$(C_1-C_3)$alkyl-(C=O)—, halo$(C_1-C_3)$alkoxy-(C=O)—, $(R_6)_2$N—$(C_1-C_2)$alkyl, $(R_6)_2$N—(C=O)—, $(C_1-C_6)$alkyl-S—, $R_6$—(O=S)—, $R_6$—(O=S=O)—, $(R_6)_2$N—(O=S=O)—, phenyl, phenyl-O—, heteroaryl, heteroaryl-O—, or heteroaryl$(C_1-C_2)$alkyl;

$R_2$ is H, hydroxy, oxo, fluoro, $(C_1-C_6)$alkyl, halo$(C_1-C_6)$alkyl, cyclo$(C_3-C_6)$alkyl, $(C_1-C_6)$alkoxy, halo$(C_1-C_6)$alkoxy, or cyano;

$R_3$ is H, $(C_1-C_6)$alkyl, halo$(C_1-C_6)$alkyl, $(C_1-C_6)$alkoxy, hydroxy$(C_1-C_6)$alkyl, $(C_1-C_6)$alkoxy$(C_1-C_6)$alkyl, or cyclo$(C_3-C_6)$alkyl;

$R_4$ is H, fluoro, $(C_1-C_2)$alkyl, or halo$(C_1-C_2)$alkyl;

$R_5$ is H, hydroxy, halogen, $(C_1-C_6)$alkyl, halo$(C_1-C_2)$alkyl, cyclo$(C_3-C_6)$alkyl, $(C_1-C_6)$alkoxy, halo$(C_1-C_6)$alkoxy, phenyl, or heteroaryl; and $R_6$ is, independently at each occurrence, H, $(C_1-C_3)$alkyl, or $R_6$ and $R_6$ form, together with the atoms they are attached to, a condensed 5, 6 or 7 membered saturated or unsaturated carbocyclic ring or a condensed 5, 6 or 7 membered saturated or unsaturated heterocyclic ring containing 1 or 2 heteroatom(s) selected from N, O and S, wherein said carbocyclic or heterocyclic ring is unsubstituted or substituted with 1 or 2 substituent(s) each independently being hydroxy, oxo, halogen, $(C_1-C_2)$alkyl, or halo$(C_1-C_2)$alkyl-;

or $R_1$ and $R_2$ form, together with the carbon ring atoms to which they are attached, a condensed 5, 6 or 7 membered saturated or unsaturated carbocyclic ring or a condensed 5, 6 or 7 membered saturated or unsaturated heterocyclic ring containing 1 or 2 heteroatom(s) selected from N, O and S, wherein said carbocyclic or heterocyclic ring is unsubstituted or substituted with 1 or 2 substituent(s) each independently being hydroxy, oxo, halogen, $(C_1-C_2)$alkyl, $(C_1-C_2)$alkoxy, hydroxy$(C_1-C_2)$alkyl, or halo $(C_1-C_2)$alkyl.

3. The compound according to claim 1, wherein $R_1$ is hydroxy, halogen, $(C_1-C_6)$alkyl, halo$(C_1-C_6)$alkyl, $(C_2-C_6)$alkenyl, $(C_2-C_6)$alkynyl, cyclo$(C_3-C_6)$alkyl, $(C_1-C_6)$alkoxy, halo$(C_1-C_6)$alkoxy, hydroxy$(C_1-C_6)$alkyl, cyano, $(R_6)_2$N—(C=O)—, $(C_1-C_6)$alkyl-S—, or heteroaryl; and/or $R_2$ is H or $(C_1-C_6)$alkyl; and/or $R_3$ is H, $(C_1-C_6)$alkyl, halo$(C_1-C_6)$alkyl, or $(C_1-C_6)$alkoxy $(C_1-C_6)$alkyl; and/or $R_4$ is H or $(C_1-C_2)$alkyl; and/or $R_5$ is H, hydroxy, halogen, $(C_1-C_6)$alkyl, or $(C_1-C_6)$alkoxy; and/or $R_6$ is H; and/or $R_1$ and $R_2$ form, together with the carbon ring atoms to which they are attached, a condensed 6 or 7 membered saturated or unsaturated carbocyclic ring.

4. The compound according to claim 1, wherein $R_1$ is hydroxy, halogen, $(C_1-C_3)$alkyl, halo$(C_1-C_3)$alkyl, $(C_1-C_3)$alkoxy, halo$(C_1-C_3)$alkoxy, or hydroxy$(C_1-C_3)$alkyl; and/or $R_2$ is H or $(C_1-C_2)$alkyl; and/or $R_3$ is H, $(C_1-C_3)$alkyl or halo$(C_1-C_3)$alkyl; and/or $R_4$ is H or methyl; and/or $R_5$ is H, halogen or $(C_1-C_2)$alkyl; and/or $R_1$ and $R_2$ form, together with the carbon ring atoms to which they are attached, a condensed 6 or 7 membered saturated or unsaturated carbocyclic ring.

5. The compound according to claim 1, wherein $R_1$ is halogen, $(C_1-C_2)$alkyl, halo$(C_1-C_2)$alkyl, $(C_1-C_2)$alkoxy, or halo$(C_1-C_2)$alkoxy; and/or $R_2$ is H; and/or $R_3$ is H or $(C_1-C_2)$alkyl; and/or $R_4$ is H; and/or $R_5$ is H.

6. The compound according to claim 1, wherein X is O.

7. The compound according to claim 1, wherein the compound is 2-(5-methylisochroman-1-yl)-4,5-dihydro-1H-imidazole, 2-(5-bromoisochroman-1-yl)-4,5-dihydro-1H-imidazole, 2-(1,5-dimethylisochroman-1-yl)-4,5-dihydro-1H-imidazole, 2-(5-chloroisochroman-1-yl)-4,5-dihydro-1H-imidazole, 1-(4,5-dihydro-1H-imidazol-2-yl)isochroman-5-carbonitrile, 2-(5-allylisochroman-1-yl)-4,5-dihydro-1H-imidazole, 2-(5-vinylisochroman-1-yl)-4,5-dihydro-1H-imidazole, 2-(5-ethynylisochroman-1-yl)-4,5-dihydro-1H-imidazole, 2-(5-ethylisochroman-1-yl)-4,5-dihydro-1H-imidazole hydrochloride, 2-(5-ethylisochroman-1-yl)-4,5-dihydro-1H-imidazole sulfate, 2-(5-ethylisochroman-1-yl)-4,5-dihydro-1H-imidazole fumarate, 1-(4,5-dihydro-1H-imidazol-2-yl)isochroman-5-ol, (1-(4,5-dihydro-1H-imidazol-2-yl)isochroman-5-yl)methanol, 2-(5-bromo-1-methylisochroman-1-yl)-4,5-dihydro-1H-imidazole, 2-((3R)-5-chloro-3-ethylisochroman-1-yl)-4,5-dihydro-1H-imidazole, slower eluting isomer of 1-(1-(4,5-dihydro-1H-imidazol-2-yl)-1-methylisochroman-5-yl)-2,2-dimethylpropan-1-ol, faster eluting isomer of 1-(1-(4,5-dihydro-1H-imidazol-2-yl)-1-methylisochroman-5-yl)-2,2-dimethylpropan-1-ol, 2-(5-ethynylisochroman-1-yl)-4,5-dihydro-1H-imidazole, 2-((3R)-3-ethyl-5-(trifluoromethyl)isochroman-1-yl)-4,5-dihydro-1H-imidazole, 2-(5-methoxyisochroman-1-yl)-4,5-dihydro-1H-imidazole, 2-(5-methoxyisochroman-1-yl)-4,5-dihydro-1H-imidazole hydrochloride, 2-(5-methoxyisochroman-1-yl)-4,5-dihydro-1H-imidazole sulfate, 2-(5-methoxyisochroman-1-yl)-4,5-dihydro-1H-imidazole hemifumarate, 2-(5-iodoisochroman-1-yl)-4,5-dihydro-1H-imidazole, 2-((3R)-3-methyl-5-(trifluoromethyl)isochroman-1-yl)-4,5-dihydro-1H-imidazole, 2-(5-bromo-4-methylisochroman-1-yl)-4,5-dihydro-1H-imidazole, faster eluting isomer of 2-(1,5-dimethylisochroman-1-yl)-4,5-dihydro-1H-imidazole, slower eluting isomer of 2-(1,5-dimethylisochroman-1-yl)-4,5-dihydro-1H-imidazole, 2-((3R)-1,3,5-trimethylisochroman-1-yl)-4,5-dihydro-1H-imidazole, 2-(5-cyclopropylisochroman-1-yl)-4,5-dihydro-1H-imidazole, 2-(3,5-dimethylisochroman-1-yl)-4,5-dihydro-1H-imidazole, 2-(5-chloro-3-methylisochroman-1-yl)-4,5-dihydro-1H-imidazole, 2-(3-ethyl-5-methylisochroman-1-yl)-4,5-dihydro-1H-imidazole, 2-(5-chloro-1,3-dimethylisochroman-1-yl)-4,5-dihydro-1H-imidazole, 2-(5-bromo-3-methylisochroman-1-yl)-4,5-dihydro-1H-imidazole, 2-(1,3,5-trimethylisochroman-1-yl)-4,5-dihydro-1H-imidazole, 2-(5-bromo-1,3-dimethylisochroman-1-yl)-4,5-dihydro-1H-imidazole, 2-((3R)-5-bromo-3-methylisochroman-1-yl)-4,5-dihydro-1H-imidazole, 2-((3R)-5-chloro-3-methylisochroman-1-yl)-4,5-dihydro-1H-imidazole, 2-((3S)-5-chloro-3-methylisochroman-1-yl)-4,5-dihydro-1H-imidazole, 2-((3S)-5-bromo-3-methylisochroman-1-yl)-4,5-dihydro-1H-imidazole, 2-((3R)-3,5-dimethylisochroman-1-yl)-4,5-dihydro-1H-imidazole, 2-((3S)-3,5-dimethylisochroman-1-yl)-4,5-dihydro-1H-imidazole, 2-(5-methoxy-3-methylisochroman-1-yl)-4,5-dihydro-1H-imidazole, 2-(5-ethyl-3-methylisochroman-1-yl)-4,5-dihydro-1H-imidazole, 2-(5-bromo-3-propylisochroman-1-yl)-4,5-dihydro-1H-imidazole, 2-(5-isopropylisochroman-1-yl)-4,5-dihydro-1H-imidazole, 2-(5-fluoroisochroman-1-yl)-4,5-dihydro-1H-imidazole, 2-(5-bromo-3-ethylisochroman-1-yl)-4,5-dihydro-1H-imidazole, 2-((3R)-5-methoxy-3-methylisochroman-1-yl)-4,5-dihydro-1H-imidazole, 2-((3R)-5-ethyl-3-methylisochroman-1-yl)-4,5-dihydro-1H-imidazole, 2-((3R)-5-ethyl-3-methylisochroman-1-yl)-4,5-dihydro-1H-imidazole hydrochloride, 2-((3R)-5-ethyl-3-methylisochroman-1-yl)-4,5-dihydro-1H-imidazole hemifumarate, 2-(3-ethyl-5-methoxyisochroman-1-yl)-4,5-dihydro-1H-imidazole, 2-((3R)-3,5-diethylisochroman-1-yl)-4,5-dihydro-1H-imidazole, 2-((3R)-3-ethyl-5-methylisochroman-1-yl)-4,5-dihydro-1H-imidazole, 2-((3R)-3-ethyl-5-methylisochroman-1-yl)-4,5-dihydro-1H-imidazole hydrochloride, 2-((3R)-3-ethyl-5-methylisochroman-1-yl)-4,5-dihydro-1H-imidazole sulfate, 2-((3R)-3-ethyl-5-methylisochroman-1-yl)-4,5-dihydro-1H-imidazole hemifumarate, 2-((3R)-3-methyl-5-(trifluoromethoxy)isochroman-1-yl)-4,5-dihydro-1H-imidazole, 2-((3R)-5-fluoro-3-methylisochroman-1-yl)-4,5-dihydro-1H-imidazole, 2-(5-ethoxyisochroman-1-yl)-4,5-dihydro-1H-imidazole, 2-(5-methyl-3-(2,2,2-trifluoroethyl)isochroman-1-yl)-4,5-dihydro-1H-imidazole, 2-((3S)-5-methoxy-3-methylisochroman-1-yl)-4,5-dihydro-1H-imidazole, 2-(5-(furan-3-yl)isochroman-1-yl)-4,5-dihydro-1H-imidazole, 2-(5-(prop-1-yn-1-yl)isochroman-1-yl)-4,5-dihydro-1H-imidazole, 1-(4,5-dihydro-1H-imidazol-2-yl)isochroman-5-carboxamide, 2-(3,7,8,9,10,10a-hexahydro-1H-cyclohepta[de]isochromen-3-yl)-4,5-dihydro-1H-imidazole, slower eluting isomer of 1-(1-(4,5-dihydro-1H-imidazol-2-yl)isochroman-5-yl)ethanol, 2-(5,7-dimethylisochroman-1-yl)-4,5-dihydro-1H-imidazole, 2-(7-bromo-5-methylisochroman-1-yl)-4,5-dihydro-1H-imidazole, 2-(7-methoxy-5-methylisochroman-1-yl)-4,5-dihydro-1H-imidazole, 2-(3,5-dimethylisothiochroman-1-yl)-4,5-dihydro-1H-imidazole, 2-(5-bromo-3-methylisothiochroman-1-yl)-4,5-dihydro-1H-imidazole, 2-(5-methylisothiochroman-1-yl)-4,5-dihydro-1H-imidazole, 2-(5-bromoisothiochroman-1-yl)-4,5-dihydro-1H-imidazole, 2-(5-bromo-1-methylisothiochroman-1-yl)-4,5-dihydro-1H-imidazole, 2-(5,7-dibromo-3-ethylisochroman-1-yl)-4,5-dihydro-1H-imidazole hydrochloride, enantiomer of 2-5-bromo-3-(2,2,2-trifluoroethyl)isochroman-1-yl)-4,5-dihydro-1H-imidazole hydrochloride, 2-(5-methoxy-1-methylisochroman-1-yl)-4,5-dihydro-1H-imidazole, 2-(5-methoxyisothiochroman-1-yl)-4,5-dihydro-1H-imidazole, 2-((3R)-5-methoxy-1,3-dimethylisochroman-1-yl)-4,5-dihydro-1H-imidazole, 2-(5-(2,2,2-trifluoroethyl)isochroman-1-yl)-4,5-dihydro-1H-imidazole, 2-((3R)-5-ethyl-1,3-dimethylisochroman-1-yl)-4,5-dihydro-1H-imidazole, 2-(5-methyl-3-(methoxymethyl)isochroman-1-yl)-4,5-dihydro-1H-imidazole, 1-(4,5-dihydro-1H-imidazol-2-yl)-5-methylisochroman-7-ol hydrobromide, 1-(4,5-dihydro-1H-imidazol-2-yl)-3-ethylisochroman-5-ol hydrochloride, enantiomer-2 of 2-(5-methoxy-3-(2,2,2-trifluoroethyl)methylisochroman-1-yl)-4,5-dihydro-1H-imidazole, 2-(1,5-dimethylisothiochroman-1-yl)-4,5-dihydro-1H-imidazole, 2-(5-(trifluoromethoxy)isochroman-1-yl)-4,5-dihydro-1H-imidazole hydrochloride, enantiomer-1 of 2-(3-ethylisochroman-1-yl)-4,5-dihydro-1H-imidazole hydrochloride, 2-(3-(2-fluoroethyl)-5-methylisochroman-1-yl)-4,5-dihydro-1H-imidazole hydrochloride, enantiomer of 2-(5-methoxyisochroman-1-yl)-4,5-dihydro-1H-imidazole, enantiomer-2 of 2-5-bromo-3-(2,2,2-trifluoroethyl)isochroman-1-yl)-4,5-dihydro-1H-imidazole hydrochloride, 2-(3-(2,2-difluoroethyl)-5-methylisochroman-1-yl)-4,5-dihydro-1H-imidazole hydrochloride, 2-(7-methoxy-3,5-dimethylisochroman-1-yl)-4,5-dihydro-1H-imidazole, enantiomer-2 of 2-((3)-5-methyl-3-(2,2,2-trifluoroethyl)isochroman-1-yl)-4,5-dihydro-1H-imidazole hydrochloride, 2-(5-(methylthio)isochroman-1-yl)-4,5-dihydro-1H-imidazole, enantiomer-2 of 2-((3)-5-bromo-3-propylisochroman-1-yl)-4,5-dihydro-1H-imidazole hydrochloride, enantiomer-2 of 2-((3R)-3-(2,2-difluoroethyl)-5-methylisochroman-1-yl)-4,5-dihydro-1H-imidazole hydrochloride, 2-(5-(difluoromethoxy)isochroman-1-yl)-4,5-dihydro-1H-imidazole hydrochloride, 2-((3R)-3-ethyl-5-methoxyisochroman-1-yl)-4,5-dihydro-1H-imidazole, enantiomer-1 of 2-(5-chloroisochroman-1-yl)-4,5-dihydro-1H-imidazole hydrochloride, 2-((3R)-5-(difluoromethoxy)-3-methylisochroman-1-yl)-4,5-dihydro-1H-imidazole hydrochloride, enantiomer of 2-(5-bromo-3-ethylisochroman-1-yl)-4,5-dihydro-1H-imidazole, enantiomer-1 of 2-(5-chloroisochroman-1-yl)-4,5-dihydro-1H-imidazole hydrochloride, enantiomer-2 of 2-(3-ethylisochroman-1-yl)-4,5-dihydro-1H-imidazole, enantiomer-2 of 2-(5-methoxyisochroman-1-yl)-4,5-dihydro-1H-imidazole hydrochloride, 2-(1-methyl-1,3-dihydrobenzo[de]isochromen-1-yl)-4,5-dihydro-1H-imidazole, 2-(5-(difluoromethyl)isochroman-1-yl)-4,5-dihydro-1H-imidazole hydrochloride, enantiomer-2 of 2-(5-chloroisochroman-1-yl)-4,5-dihydro-1H-imidazole hydrochloride, enantiomer-2 of 2-(5-bromoisochroman-1-yl)-4,5-dihydro-1H-imidazole hydrochloride, 2-(1,3-dihydrobenzo[de]isochromen-1-yl)-4,5-dihydro-1H-imidazole hydrochloride, enantiomer of 2-(1-methyl-1,3-dihydrobenzo[de]isochromen-1-yl)-4,5-dihydro-1H-imidazole, 2-(3-methyl-1,3-dihydrobenzo[de]isochromen-1-yl)-4,5-dihydro-1H-imidazole hydrochloride, 2-(3-ethyl-1,3-dihydrobenzo[de]isochromen-1-yl)-4,5-dihydro-1H-imidazole hydrochloride, or enantiomer of 2-(5-bromo-1-methylisochroman-1-yl)-4,5-dihydro-1H-imidazole.

8. A method for the treatment of a disorder, condition or disease where an alpha2 agonist is indicated to be useful, which method comprises administering to a mammal in need of such treatment an effective amount of at least one compound according to claim 1.

9. A method for the treatment of a disorder, condition or disease where an alpha2A agonist is indicated to be useful, which method comprises administering to a mammal in need of such treatment an effective amount of at least one compound according to claim 1.

10. The method according to claim 9, wherein the disorder, condition or disease is delirium, hyperactive delirium, insomnia, ADHD, benzodiazepine or alcohol or opioid or tobacco withdrawal, premature ejaculation, hypertension, tachycardia, restless leg syndrome, muscular spasticity, hot flashes, anxiety, post traumatic stress disorder, pain, chronic pelvic pain syndrome, breakthrough cancer pain, or condition wherein sedation or analgesia is needed.

11. A pharmaceutical composition comprising at least one compound according to claim 1 and a pharmaceutically acceptable carrier, diluent and/or excipient.

12. The pharmaceutical composition according to claim 11, wherein the composition further comprises at least one other active ingredient.

\* \* \* \* \*